US010113189B2

(12) United States Patent
Bauer et al.

(10) Patent No.: US 10,113,189 B2
(45) Date of Patent: Oct. 30, 2018

(54) ISOLATION AND CHARACTERIZATION OF A NOVEL PYTHIUM OMEGA 3 DESATURASE WITH SPECIFICITY TO ALL OMEGA 6 FATTY ACIDS LONGER THAN 18 CARBON CHAINS

(71) Applicants: BASF Plant Science GmbH, Ludwigshafen (DE); Bioriginal Food & Science Corp., Saskatoon (CA)

(72) Inventors: Jörg Bauer, Limburgerhof (DE); Guohai Wu, Saskatoon (CA); Xiao Qiu, Saskatoon (CA)

(73) Assignees: BASF Plant Science GmbH, Ludwigshafen (DE); Bioriginal Food & Science Corp., Saskatoon (CA)

( * ) Notice: Subject to any disclaimer, the term of this patent is extended or adjusted under 35 U.S.C. 154(b) by 374 days.

(21) Appl. No.: 14/684,682

(22) Filed: Apr. 13, 2015

(65) Prior Publication Data

US 2015/0211032 A1    Jul. 30, 2015

Related U.S. Application Data

(62) Division of application No. 12/438,373, filed as application No. PCT/EP2007/058528 on Aug. 16, 2007, now Pat. No. 9,029,111.

(30) Foreign Application Priority Data

Aug. 24, 2006    (EP) .................................... 06119502

(51) Int. Cl.
| | |
|---|---|
| *C12P 7/64* | (2006.01) |
| *C12N 15/82* | (2006.01) |
| *C12N 9/02* | (2006.01) |
| *C12N 15/52* | (2006.01) |
| *C12N 9/04* | (2006.01) |
| *A61K 8/92* | (2006.01) |
| *A61K 31/202* | (2006.01) |
| *A61K 8/64* | (2006.01) |
| *A61Q 19/00* | (2006.01) |

(52) U.S. Cl.
CPC ............ *C12P 7/6472* (2013.01); *A61K 8/64* (2013.01); *A61K 8/922* (2013.01); *A61K 31/202* (2013.01); *A61Q 19/00* (2013.01); *C12N 9/0006* (2013.01); *C12N 9/0083* (2013.01); *C12N 9/0093* (2013.01); *C12N 15/52* (2013.01); *C12P 7/6427* (2013.01); *C12P 7/6436* (2013.01); *A61K 2800/10* (2013.01)

(58) Field of Classification Search
None
See application file for complete search history.

(56) References Cited

U.S. PATENT DOCUMENTS

| | | | |
|---|---|---|---|
| 4,962,028 | A | 10/1990 | Bedbrook et al. |
| 5,187,267 | A | 2/1993 | Comai et al. |
| 5,352,605 | A | 10/1994 | Fraley et al. |
| 5,504,200 | A | 4/1996 | Hall et al. |
| 5,608,152 | A | 3/1997 | Kridl et al. |
| 5,614,393 | A | 3/1997 | Thomas et al. |
| 6,043,411 | A | 3/2000 | Nishizawa et al. |
| 7,765,793 | B2 | 8/2010 | Nishiyama et al. |
| 2007/0224661 | A1 | 9/2007 | Cirpus et al. |

FOREIGN PATENT DOCUMENTS

| | | |
|---|---|---|
| CA | 2007091 A1 | 6/1990 |
| EP | 0 249 676 A2 | 12/1987 |
| EP | 0 335 528 A2 | 10/1989 |
| EP | 0 375 091 A1 | 6/1990 |
| EP | 0 388 186 A1 | 9/1990 |
| EP | 0 550 162 A1 | 7/1993 |
| EP | 0 794 250 A1 | 9/1997 |
| WO | WO-84/02913 A1 | 8/1984 |
| WO | WO-91/13972 A1 | 9/1991 |
| WO | WO-91/13980 A1 | 9/1991 |
| WO | WO-93/06712 A1 | 4/1993 |
| WO | WO-93/11245 A1 | 6/1993 |
| WO | WO-93/21334 A1 | 10/1993 |
| WO | WO-94/11516 A1 | 5/1994 |
| WO | WO-94/18337 A1 | 8/1994 |
| WO | WO-95/15389 A2 | 6/1995 |
| WO | WO-95/16783 A1 | 6/1995 |
| WO | WO-95/18222 A1 | 7/1995 |

(Continued)

OTHER PUBLICATIONS

Google translation of Zank et al (WO 2005/012316 A2).*
Friedberg 2006 Briefings in Bioinformatics 7:3 p. 225-242.*
Poulos, A., "Very Long Chain Fatty Acids in Higher Animals—A Review", Lipids, vol. 30, No. 1, (1995), pp. 1-14.
Horrocks, L.A., et al., "Health Benefits of Docosahexaenoic Acid (DHA)", Pharmacological Research, vol. 40, No. 3, (1999), pp. 211-225.
Stukey, J. E., et al., "The OLE1 Gene of *Saccharomyces cerevisiae* Encodes the Δ 9 Fatty Acid Desaturase and Can Be Functionally Replaced by the Rat Stearoyl-CoA Desaturase Gene", The Journal of Biological Chemistry, vol. 265, No. 33, (1990), pp. 20144-20149.
Wada, H., et al., "Enhancement of Chilling Tolerance of a Cyanobacterium by Genetic Manipulation of Fatty Acid Desaturation", Nature, vol. 347, (1990), pp. 200-203.

(Continued)

*Primary Examiner* — Matthew R Keogh
(74) *Attorney, Agent, or Firm* — Drinker Biddle & Reath LLP

(57) ABSTRACT

The present invention relates to a polynucleotide encoding an omega 3 (ω-3) desaturase from *Pythium irregulare* with specificity to long chain polyunsaturated omega 6 (ω-6) fatty acids as well as a vector containing the polynucleotide, and a host cell containing the vector or the polynucleotide. Moreover, the present invention pertains to a polypeptide encoded by the polynucleotide, antibodies against the polypeptide as well as a method for the manufacture of the polypeptide. Further, encompassed by the present invention are transgenic non-human organisms. Finally, the present invention relates to methods for the manufacture of compounds and oil-fatty acid-, or lipid-containing compositions.

22 Claims, 6 Drawing Sheets

Figure 4:
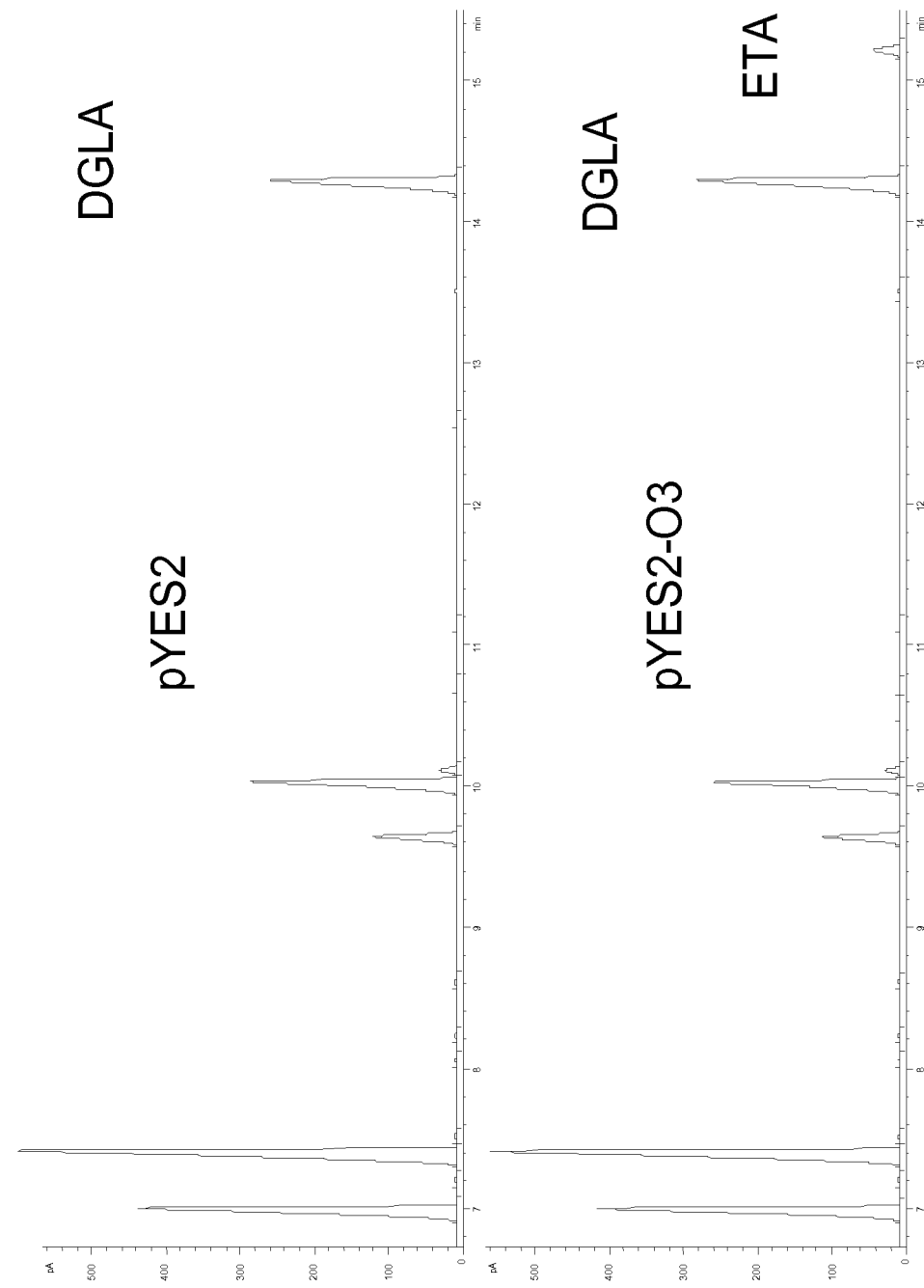

Specification includes a Sequence Listing.

(56) References Cited

FOREIGN PATENT DOCUMENTS

| WO | WO-95/19443 A2 | 7/1995 |
|---|---|---|
| WO | WO-95/23230 A1 | 8/1995 |
| WO | WO-96/12814 A1 | 5/1996 |
| WO | WO-96/21022 A2 | 7/1996 |
| WO | WO-97/06250 A1 | 2/1997 |
| WO | WO-97/21340 A1 | 6/1997 |
| WO | WO-98/45461 A1 | 10/1998 |
| WO | WO-98/46763 A1 | 10/1998 |
| WO | WO-98/46764 A1 | 10/1998 |
| WO | WO-98/46765 A1 | 10/1998 |
| WO | WO-98/46776 A2 | 10/1998 |
| WO | WO-99/16890 A2 | 4/1999 |
| WO | WO-99/27111 A1 | 6/1999 |
| WO | WO-99/46394 A1 | 9/1999 |
| WO | WO-99/64616 A2 | 12/1999 |
| WO | WO-00/21557 A1 | 4/2000 |
| WO | WO-2004/071467 A2 | 8/2004 |
| WO | WO2005012316 A2 * | 2/2005 |
| WO | WO-2005/083053 A2 | 9/2005 |
| WO | WO2005083053 A2 * | 9/2005 |
| WO | WO-2005/118814 A2 | 12/2005 |
| WO | WO-2006/052870 A2 | 5/2006 |

OTHER PUBLICATIONS

Huang, Y.-S., et al., "Cloning of Δ12- and Δ6-Desaturases from *Mortierella alpina* and Recombinant Production of γ-Linolenic Acid in *Saccharomyces cerevisiae*", Lipids, vol. 34, No. 7, (1999), pp. 649-659.
McKeon, T., et al., "Stearoyl-Acyl Carrier Protein Desaturase from Safflower Seeds", Methods in Enzymology, vol. 71, (1981), pp. 275-281.
Wang, X.-M., et al., "Biosynthesis and Regulation of Linolenic Acid in Higher Plants", Plant Physiol. Biochem. vol. 26, No. 6, (1988), pp. 777-792.
Vazhappilly, R., et al., "Heterotrophic Production Potential of Omega-3 Polyunsaturated Fatty Acids by Microalgae and Algae-like Microorganisms", Botanica Marina, vol. 41, (1998), pp. 553-558.
Totani, N., et al., "The Filamentous Fungus *Mortierella alpina*, High in Arachidonic Acid", Lipids, vol. 22, No. 12, (1987), pp. 1060-1062.
Akimoto, M., et al., "Carbon Dioxide Fixation and Polyunsaturated Fatty Acid Production by the Red Alga *Porphyridium cruentum*", Applied Biochemistry and Biotechnology, vol. 73, (1998), pp. 269-278.
Yu, R., et al., "Production of Eicosapentaenoic Acid by a Recombinant Marine Cyanobacterium, *Synechococcus* sp.", Lipids, vol. 35, No. 10, (2000), pp. 1061-1064.
Takeyama, H., et al., "Expression of the Eicosapentaenoic Acid Synthesis Gene Cluster from *Shewanella* sp. in a Transgenic Marine Cyanobacterium, *Synechococcus* sp.", Microbiology, vol. 143, (1997), pp. 2725-2731.
Zank, T. K., et al., "Cloning and Functional Characterisation of an Enzyme Involved in the Elongation of Δ6-Polyunsaturated Fatty Acids from the Moss *Physcomitrella patens*", The Plant Journal, vol. 31, No. 3, (2002), pp. 255-268.
Sakuradani, E., et al., "Δ6-Fatty Acid Desaturases from an Arachidonic Acid-Producing *Mortierella* Fungus Gene Cloning and its Heterologous Expression in a Fungus, *Aspergillus*", Gene, vol. 238, (1999), pp. 445-453.
Sprecher, H. "Metabolism of Highly Unsaturated n-3 and n-6 Fatty Acids", Biochimica et Biophysica Acta, vol. 1486, (2000), pp. 219-231.
Tocher, D.R., et al., "Recent Advances in the Biochemistry and Molecular Biology of Fatty Acyl Desaturases", Prog. Lipid. Res., vol. 37, No. 2/3, (1998), pp. 73-117.
Domergue, F., et al., "Cloning and Functional Characterization of *Phaeodactylum tricornutum* Front-End Desaturases Involved in Eicosapentaenoic Acid Biosynthesis", Eur. J. Biochem, vol. 269, (2002), pp. 4105-4113.

Shimokawa, I., "Beneficial Effects of Eicosapentaenoic Acid on Endothelial Vasodilator Functions in Animals and Humans", World Rev. Nutr. Diet. Basel, vol. 88, (2001), pp. 100-108.
Calder, P. C., "Dietary Modification of Inflammation with Lipids", Proceedings of the Nutrition Society, vol. 61, (2002), pp. 345-358.
Cleland, L. G., et al., "Fish Oil and Rheumatoid Arthritis: Antiinflammatory and Collateral Health Benefits", The Journal of Rheumatology, vol. 27, No. 10, (2000), pp. 2305-2307.
Pereira, S. L., et al., "A Novel ω3-Fatty Acid Desaturase Involved in the Biosynthesis of Eicosapentaenoic Acid", Biochem. J., vol. 378, (2004), pp. 665-671.
Franck, A., et al., "Nucleotide Sequence of Cauliflower Mosaic Virus DNA", Cell, vol. 21, (1980), pp. 285-294.
Ward, E.R., et al., "Chemical Regulation of Transgene Expression in Plants", Plant Molecular Biology, vol. 22, (1993), pp. 361-366.
Stockhaus, J., et al., "Correlation of the Expression of the Nuclear Photosynthetic Gene ST-LS1 with the Presence of Chloroplasts", The EMBO Journal, vol. 8, No. 9, (1989), pp. 2445-2451.
Baeumlein, H., et al., "Cis-Analysis of a Seed Protein Gene Promoter: The Conservative RY Repeat CATGCATG Within the Legumin Box is Essential for Tissue-Specific Expression of a Legumin Gene", The Plant Journal, vol. 2, No. 2, (1992), pp. 233-239.
Falciatore, A., et al., "Transformation of Nonselectable Reporter Genes in Marine Diatoms", Marine Biotechnology, vol. 1, (1999), pp. 239-251.
Becker, D., et al., "New Plant Binary Vectors with Selectable Markers Located Proximal to the Left T-DNA Border", Plant Molecular Biology, vol. 20, (1992), pp. 1195-1197.
Bevan, M., "Binary *Agrobacterium* Vectors for Plant Transformation", Nucleic Acids Research, vol. 12, No. 22, (1984), pp. 8711-8721.
Gielen, J., et al. The Complete Nucleotide Sequence of the TL-DNA of the *Agrobacterium tumefaciens* Plasmid pTiAch5, The EMBO Journal, vol. 3, No. 4, (1984), pp. 835-846.
Gallie, D.R., et al., "A Comparison of Eukaryotic Viral 5'-leader Sequences as Enhancers of mRNA Expression in vivo", Nucleic Acids Research, vol. 15, No. 21, (1987), pp. 8693-8711.
Benfey, P. N., et al., "The CaMV 35S Enhancer Contains at Least Two Domains Which Can Confer Different Developmental and Tissue-Specific Expression Patterns", The EMBO Journal, vol. 8, No. 8, (1989), pp. 2195-2202.
Kermode, A.R., "Mechanisms of Intracellular Protein Transport and Targeting in Plant Cells", Critical Reviews in Plant Sciences, vol. 15, No. 4, (1996), pp. 285-423.
Gatz, C., "Chemical Control of Gene Expression", Annual Rev. Plant Physiol. Plant Mol. Biol., vol. 48, (1997), pp. 89-108.
Gatz, C., et al., "Stringent Repression and Homogeneous De-Repression by Tetracycline of a Modified CaMV 35S Promoter in Intact Transgenic Tobacco Plants", The Plant Journal, vol. 2, No. 3, (1992), pp. 397-404.
Baeumlein H., et al., "A Novel Seed Protein Gene from *Vicia faba* is Developmentally Regulated in Transgenic Tobacco and Arabidopsis Plants", Mol. Gen. Genet., vol. 225, No. 3, (1991), pp. 459-467.
Mikolajczak, K. L., et al., "Search for New Industrial Oils v. Oils of Cruciferae", The Journal of the American Oil Chemists' Society, vol. 38, (1961), pp. 678-681.
O'Brien, D. J., et al., "Production of Eicosapentaenoic Acid by the Filamentous Fungus *Pythium irregulare*", Applied Microbiology and Biotechnology, vol. 40, No. 2/3, (1993), pp. 211-214.
Wu, G., et al., "Stepwise Engineering to Produce High Yields of Very Long-Chain Polyunsaturated Fatty Acids in Plants", Nature Biotechnology, vol. 23, No. 8, (2005), pp. 1013-1017.
Pereira, S. L., et al., "A Novel ω3-Fatty Acid Desaturase Involved in the Biosynthesis of Eicosapentaenoic Acid", Biochem. J., vol. 378, No. 2, (2004), pp. 665-671.
Truksa, M., et al., "Metabolic Engineering of Plants to Produce Very Long-Chain Polyunsaturated Fatty Acids", Transgenic Research, vol. 15, No. 2, (2006), pp. 131-137.
"Omega 3 Acyl-Lipid Desaturase", Database Uniprot, Accession No. 0704F0, Jul. 5, 2004.

(56) References Cited

OTHER PUBLICATIONS

Zhu et al. (Apr. 2006) Sequence Alignment for SEQ ID No. 1 from U.S. Pat. No. 7,465,793 with SEQ ID No. 2 of U.S. Appl. No. 12/438,373.

* cited by examiner

```
O3-Pythium1     (1)  ATGGCGTCCACCTCCGCCGCCCAAGACGCCGCCGCCGTACGAGTTCCCGTCGCTGACCGAGATCAAGCGCGCTGCCCAGCGAGT      85
O3-Pythium2     (1)  ATGGCGTCCACCTCCGCCGCCCAAGACGCCGCCGCCGTACGAGTTCCCGTCGCTGACCGAGATCAAGCGCGCTGCCCAGCGAGT     170

O3-Pythium1    (86)  GCTTCGAGGCGTCGGTGCCCCTGTCGCTCTACTACACCGCGCTCGCTGGCGCTTGCCGGCTCGCGGTCGCGCTCTCGTA          170
O3-Pythium2    (86)  GCTTCGAAGCGTCGGTGCCCGTGTCGCTCTACTACACCGCGCTCGCTGGCGCTTGCCGGCTCGCGGTCGCGCTCTCGTA          255

O3-Pythium1   (171)  TGCGCGTGCGCTGCCGCTGGTGCAGGCGAACGCGCGTCGCTCGAACCGCCACGCTCTGTACGGGCTACGTGCTACTGCAGGGCATCGTG  255
O3-Pythium2   (171)  CGCGCGTGCGCTGCCGCTGGTGCAGGCGAACGCGCGTCGCTCGAACCGCCACGCTCTGTACGGGCTACGTGCTACTGCAGGGCATCGTG  340

O3-Pythium1   (256)  TTCTGGGGCTTCTTCACAGTCGGCCACGACTCGGCCACGCCGTTCTCGCGACCGCCGTTCTCGCGCCGCTCGCATGTGCTCAACTTCAGCGTCGGCACGC  340
O3-Pythium2   (256)  TTCTGGGGCTTCTTCACAGTCGGCCACGACTCGGCCACGCCGTTCTCGCGACCGCCGTTCTCGCGCCGCTCGCATGTGCTCAACTTCAGCGTCGGCACGC  425

O3-Pythium1   (341)  TCATGCACTCGATCATCCTCACGCCGTTCGAGTCCTGGAAGCTGTCGCACCGCCACCACAAGAACACGGGCAACATCGACAA          425
O3-Pythium2   (341)  TCATGCACTCGATCATCCTCACGCCGTTCGAGTCCTGGAAGCTGTCGCACCGCCACCACAAGAACACGGGCAACATCGACAA          510

O3-Pythium1   (426)  GGACGAGATCTTCTACCCGGCAGCGCGGAGGCTGACTCACACCCAGTCTCCCCGCCACTTGTTCATGTCGCTCCGGCTCGGCGTGTTT      510
O3-Pythium2   (426)  GGACGAGATCTTCTACCCGGCAGCGCGGAGGCTGACTCACACCCAGTCTCCCCGCCACTTGTTCATGTCGCTCCGGCTCGGCGTGTTT      595

O3-Pythium1   (511)  GCCTACCTGTTCGCGGGCTTCCCTCCTCCGCACGATGAACCATCGCCAGTCGTCTCTACTCGTACTTGACCTTCGTCTTTGGGCTTCACGACCATGCGAT  595
O3-Pythium2   (511)  GCCTACCTGTTCGCGGGCTTCCCTCCTCCGCACGATGAACCATCGCCAGTCGTCTCTACTCGTACTTGACCTTCGTCTTTGGGCTTCACGACCATGCGAT  680

O3-Pythium1   (596)  TGATCATCTCGCTCGGCGTCGGCGCTCTCGGCGCGTCGGCGTCGGCGTTCCATTGTTCATCTTGTTCGTCTTCGCCACGATGCTCGTGGTCACCACGTTCTTGCACCAGAAGGGCAACCTCTCGTCCGTGGACGTCAACCTCTCGCGCGCTCGATCGACAACCTGAGCC  765
O3-Pythium2   (596)  TGATCATCTCGCTCGGCGTCGGCGCTCTCGGCGCGTCGGCGTCGGCGTTCCATTGTTCATCTTGTTCGTCTTCGCCACGATGCTCGTGGTCACCACGTTCTTGCACCAGAAGGGCAACCTCTCGTCCGTGGACGTCAACCTCTCGCGCGCTCGATTGACAACCTGAGCC  850

O3-Pythium1   (766)  CTACTACTTTGGTCCATTGTTCATTGTTCGTCTTCGCCACGATGCTCGTGGTCACCACGTTCTTGCACCAGAAGGGCAACCTCTCG      850
O3-Pythium2   (766)  CTACTACTTTGGTCCATTGTTCATTGTTCGTCTTCGCCACGATGCTCGTGGTCACCACGTTCTTGCACCAGAAGGGCAACCTCTCG      935

O3-Pythium1   (851)  ACAACATCGGACGGCACGCACCAGATCCACCACCACCTGTTTCCCGATCATCCCGATCATCCCGCCAAGAACGCGGCCCGATCATCCCGACGTTCTTCCCGACGTCATCCGCATGCCGCCATGTACGCCAAGTACGGC  935
O3-Pythium2   (851)  ACAACATCGGACGGCACGCACCAGATCCACCACCACCTGTTTCCCGATCATCCCGATCATCCCGCCAAGAACGCGGCCCGATCATCCCGACGTTCTTCCCGACGTCATCCGCATGCCGCCATGTACGCCAAGTACGGC  1020

O3-Pythium1   (936)  GGCGTTCCCAGAGCTCGTGCGCAAGAGCTCGTGCGCAAGAACGCGGCCCGCCATGCCGCCATGTACGCCAAGTACGGC             1020
O3-Pythium2   (936)  GGCGTTCCCAGAGCTCGTGCGCAAGAGCTCGTGCGCAAGAACGCGGCCCGCCATGCCGCCATGTACGCCAAGTACGGC             1092

O3-Pythium1  (1021)  GTGGTCGACACGGACACGGACGCCAAGACGTTCACGCTCAAGGAAGCCAAGACCAAGTCGAGCTAA
O3-Pythium2  (1021)  GTGGTCGACACGGACACGGACGCCAAGACGTTCACGCTCAAGGAAGCCAAGACCAAGTCGAGCTAA
```

Figure 1

```
                   1                                                                            75
O3-Pythium-1   (1)  MASTSAAQDAAPYEFPSLTEIKRALPSECFEASVPLSLYYTARSLALAGSLAVALSYARALPLVQANALLDATLC
O3-Pythium-2   (1)  MASTSAAQDAAPYEFPSLTEIKRALPSECFEASVPLSLYYTARSLALAGSLAVALSYARALPLVQANALLDATLC 76                                                                           150
O3-Pythium-1  (76)  TGYVLLQGIVFWGFFTVGHDCGHGAFSRSHVLNFSVGTLMHSIILTPFESWKLSHRHHHKNTGNIDKDEIFYPQR
O3-Pythium-2  (76)  TGYVLLQGIVFWGFFTVGHDCGHGAFSRSHVLNFSVGTLMHSIILTPFESWKLSHRHHHKNTGNIDKDEIFYPQR 151                                                                          225
O3-Pythium-1 (151)  EADSHPVSRHLVMSLGSAWFAYLFAGFPPRTMNHFNPWEAMYVRRVAAVIISLGVLFAFAGLYSYLTFVLGFTTM
O3-Pythium-2 (151)  EADSHPVSRHLVMSLGSAWFAYLFAGFPPRTMNHFNPWEAMYVRRVAAVIISLGVLFAFAGLYSYLTFVLGFTTM 226                                                                          300
O3-Pythium-1 (226)  AIYYFGPLFIFATMLVTTFLHHNDEETPWVADSEWTYVKGNLSSVDRSYGALIDNLSHNIGTHQIHHLFPIIPH
O3-Pythium-2 (226)  AIYYFGPLFVFATMLVTTFLHHNDEETPWVADSEWTYVKGNLSSVDRSYGALIDNLSHNIGTHQIHHLFPIIPH 301                                          363
O3-Pythium-1 (301)  YKLNDATAAFAKAFPELVRKNAAPIIPTFFRMAAMYAKYGVDTDAKTFTLKEAKAAAKTKSS
O3-Pythium-2 (301)  YKLNDATAAFAKAFPELVRKNAAPIIPTFFRMAAMYAKYGVDTDAKTFTLKEAKAAAKTKSS
```

Figure 2

```
O3-P.irregulare   (1)   MASTSAAQDAAPYEFPSLTEIKRALPSECFEASVPLSLYYTARSLALAGSLAVALSYARALPLVQANALLDATLC    75
O3-P.infestans    (1)   -----MATKEAYVFPTLTEIKRSLPKDCFEASVPLSLYYTVRCLVIAVALTFGLNYARALPEVESFWALDAALC
O3-S.diclina      (1)   -----MTEDKTKVEFPTLTELKHSIPNACFESNLGLSLYYTARAIFNASASAALLYAARSTPFIADNVLLHALVC    150

O3-P.irregulare   (76)  TGYVLLQGIVFWGFFTVGHDCGHGAFSRSHVLNFSVGTLMHSIILTPFESWKLSHRHHHKNTGNIDKDEIFYPQR
O3-P.infestans    (70)  TGYILLQGIVFWGFFTVGHDAGHGAFSRYHLLNFVVGTFMHSLLILTPFESWKLTHRHHHKNTGNIDRDEVFYPQR
O3-S.diclina      (71)  ATYIYVQGVIFWGFFTVGHDCGHSAFSRYHSVNFIIGCIMHSAILTPFESWRVTHRHHHKNTGNIDKEIFYPHR    225

O3-P.irregulare   (151) EADSHPVSRHLVMSLGSAWFAYLFAGFPPRTMNHFNPWEAMYVRRVAAVIISLGVLFAFAGLYSYLTFVLGFTTM
O3-P.infestans    (145) KADDHPLSRNLLIALGAAWLAYLVEGFPPRKVNHFNPFFEPLFVRQVSAVVISLLAHFFVAGLSIYLSLQLGLKTM
O3-S.diclina      (146) SVKDLQDVRQWVYTLGGAWFVYLKVGYAPRTMSHFDPWDPLLLRRASAVIVSLGVWAAFFAAYAYLTYSLGFAVM    300

O3-P.irregulare   (226) AIYYFGPLFVFATMLVVTTFLHHNDEETPWYADSEWTYVKGNLSSVDRSYGALIDNLSHNIGTHQIHHLFPIIPH
O3-P.infestans    (220) AIYYYGPVFVFGSMLVITTFLHHNDEETPWYADSEWTYVKGNLSSVDRSYGALIDNLSHNIGTHQIHHLFPIIPH
O3-S.diclina      (221) GLYYAPLFVFASFLVITTFLHHNDEATPWYGDSEWTYVKGNLSSVDRSYGAFVDNLSHHIGTHQVHHLFPIIPH    368

O3-P.irregulare   (301) YKLNDATAAFAKAFPELVRKNAAPIIPTFFRMAAMYAKYGVVDTDAKTFTLKEAKAAAKTKSS-----
O3-P.infestans    (295) YKLKKATAAFHQAFPELVRKSDEPIIKAFFRVGRLYANYGVVDQEAKLFTLKEAKAATEAAAKTKST-
O3-S.diclina      (296) YKLNEATKHFAAAYPHLVRRNDEPIITAFFKTAHLFVNYGAVPETAQIFTLKESAAAAKAKSD-----
```

Figure 3

SEQUENCE LISTING

```
<160> NUMBER OF SEQ ID NOS: 53

<210> SEQ ID NO 1
<211> LENGTH: 1092
<212> TYPE: DNA
<213> ORGANISM: Pythium irregulare
<220> FEATURE:
<221> NAME/KEY: CDS
<222> LOCATION: (1)..(1092)

<400> SEQUENCE: 1 atg gcg tcc acc tcc gcc gcc caa gac gcc gcg ccg tac gag ttc ccg      48
Met Ala Ser Thr Ser Ala Ala Gln Asp Ala Ala Pro Tyr Glu Phe Pro
1               5                   10                  15 tcg ctg acc gag atc aag cgc gcg ctg ccc agc gag tgc ttc gag gcg      96
Ser Leu Thr Glu Ile Lys Arg Ala Leu Pro Ser Glu Cys Phe Glu Ala
```

```
                  20                  25                  30
tcg gtg ccc ctg tcg ctc tac tac acc gcg cgc tcg ctg gcg ctt gcc      144
Ser Val Pro Leu Ser Leu Tyr Tyr Thr Ala Arg Ser Leu Ala Leu Ala
         35                  40                  45 ggc tcg ctc gcg gtc gcg ctc tcg tat gcg cgt gcg ctg ccg ctg gtg      192
Gly Ser Leu Ala Val Ala Leu Ser Tyr Ala Arg Ala Leu Pro Leu Val
 50                  55                  60 cag gcg aac gcg ctg ctc gac gcc acg ctc tgt acg ggc tac gtg cta      240
Gln Ala Asn Ala Leu Leu Asp Ala Thr Leu Cys Thr Gly Tyr Val Leu
 65                  70                  75                  80 ctg cag ggc atc gtg ttc tgg ggc ttc ttc aca gtc ggc cac gac tgc      288
Leu Gln Gly Ile Val Phe Trp Gly Phe Phe Thr Val Gly His Asp Cys
                 85                  90                  95 ggc cac ggc gcg ttc tcg cgc tcg cat gtg ctc aac ttc agc gtc ggc      336
Gly His Gly Ala Phe Ser Arg Ser His Val Leu Asn Phe Ser Val Gly
             100                 105                 110 acg ctc atg cac tcg atc atc ctc acg ccg ttc gag tcc tgg aag ctg      384
Thr Leu Met His Ser Ile Ile Leu Thr Pro Phe Glu Ser Trp Lys Leu
         115                 120                 125 tcg cac cgc cac cac cac aag aac acg ggc aac atc gac aag gac gag      432
Ser His Arg His His His Lys Asn Thr Gly Asn Ile Asp Lys Asp Glu
 130                 135                 140 atc ttc tac ccg cag cgc gag gct gac tca cac cca gtc tcc cgc cac      480
Ile Phe Tyr Pro Gln Arg Glu Ala Asp Ser His Pro Val Ser Arg His
145                 150                 155                 160 ttg gtc atg tcg ctc ggc tcg gcg tgg ttt gcc tac ctg ttc gcg ggc      528
Leu Val Met Ser Leu Gly Ser Ala Trp Phe Ala Tyr Leu Phe Ala Gly
                 165                 170                 175 ttc cct cct cgc acg atg aac cac ttc aac ccg tgg gaa gcg atg tac      576
Phe Pro Pro Arg Thr Met Asn His Phe Asn Pro Trp Glu Ala Met Tyr
             180                 185                 190 gtg cgt cgt gtg gcc gct gtg atc atc tcg ctc ggc gtg ctc ttc gcc      624
Val Arg Arg Val Ala Ala Val Ile Ile Ser Leu Gly Val Leu Phe Ala
         195                 200                 205 ttc gca ggt ctc tac tcg tac ttg acc ttc gtc ttg ggc ttc acg acc      672
Phe Ala Gly Leu Tyr Ser Tyr Leu Thr Phe Val Leu Gly Phe Thr Thr
 210                 215                 220 atg gcg atc tac tac ttt ggt cca ttg ttc atc ttc gcc acg atg ctc      720
Met Ala Ile Tyr Tyr Phe Gly Pro Leu Phe Ile Phe Ala Thr Met Leu
225                 230                 235                 240 gtg gtc acc acg ttc ttg cac cac aac gac gaa gag act ccg tgg tac      768
Val Val Thr Thr Phe Leu His His Asn Asp Glu Glu Thr Pro Trp Tyr
                 245                 250                 255 gcg gat tcg gag tgg acg tac gtc aag ggc aac ctc tcg tcc gtg gac      816
Ala Asp Ser Glu Trp Thr Tyr Val Lys Gly Asn Leu Ser Ser Val Asp
             260                 265                 270 cgc tca tac ggc gcg ctg atc gac aac ctg agc cac aac atc ggc acg      864
Arg Ser Tyr Gly Ala Leu Ile Asp Asn Leu Ser His Asn Ile Gly Thr
         275                 280                 285 cac cag atc cac cac ctg ttc ccg atc atc ccg cac tac aag ctc aac      912
His Gln Ile His His Leu Phe Pro Ile Ile Pro His Tyr Lys Leu Asn
 290                 295                 300 gac gcc acg gcg gcg ttt gcc aag gcg ttc cca gag ctc gtg cgc aag      960
Asp Ala Thr Ala Ala Phe Ala Lys Ala Phe Pro Glu Leu Val Arg Lys
305                 310                 315                 320 aac gcg gcg ccg atc atc ccg acg ttc ttc cgc atg gcc gcc atg tac     1008
Asn Ala Ala Pro Ile Ile Pro Thr Phe Phe Arg Met Ala Ala Met Tyr
                 325                 330                 335 gcc aag tac ggc gtg gtc gac acg gac gcc aag acg ttc acg ctc aag     1056
```

Ala Lys Tyr Gly Val Val Asp Thr Asp Ala Lys Thr Phe Thr Leu Lys
            340                 345                 350 gaa gcc aag gcc gcc gcc aag acc aag tcg agc taa                    1092
Glu Ala Lys Ala Ala Ala Lys Thr Lys Ser Ser
        355                 360

<210> SEQ ID NO 2
<211> LENGTH: 363
<212> TYPE: PRT
<213> ORGANISM: Pythium irregulare

<400> SEQUENCE: 2

Met Ala Ser Thr Ser Ala Ala Gln Asp Ala Ala Pro Tyr Glu Phe Pro
1               5                   10                  15

Ser Leu Thr Glu Ile Lys Arg Ala Leu Pro Ser Glu Cys Phe Glu Ala
            20                  25                  30

Ser Val Pro Leu Ser Leu Tyr Tyr Thr Ala Arg Ser Leu Ala Leu Ala
        35                  40                  45

Gly Ser Leu Ala Val Ala Leu Ser Tyr Ala Arg Ala Leu Pro Leu Val
    50                  55                  60

Gln Ala Asn Ala Leu Leu Asp Ala Thr Leu Cys Thr Gly Tyr Val Leu
65                  70                  75                  80

Leu Gln Gly Ile Val Phe Trp Gly Phe Phe Thr Val Gly His Asp Cys
                85                  90                  95

Gly His Gly Ala Phe Ser Arg Ser His Val Leu Asn Phe Ser Val Gly
            100                 105                 110

Thr Leu Met His Ser Ile Ile Leu Thr Pro Phe Glu Ser Trp Lys Leu
        115                 120                 125

Ser His Arg His His His Lys Asn Thr Gly Asn Ile Asp Lys Asp Glu
    130                 135                 140

Ile Phe Tyr Pro Gln Arg Glu Ala Asp Ser His Pro Val Ser Arg His
145                 150                 155                 160

Leu Val Met Ser Leu Gly Ser Ala Trp Phe Ala Tyr Leu Phe Ala Gly
                165                 170                 175

Phe Pro Pro Arg Thr Met Asn His Phe Asn Pro Trp Glu Ala Met Tyr
            180                 185                 190

Val Arg Arg Val Ala Ala Val Ile Ile Ser Leu Gly Val Leu Phe Ala
        195                 200                 205

Phe Ala Gly Leu Tyr Ser Tyr Leu Thr Phe Val Leu Gly Phe Thr Thr
    210                 215                 220

Met Ala Ile Tyr Tyr Phe Gly Pro Leu Phe Ile Phe Ala Thr Met Leu
225                 230                 235                 240

Val Val Thr Thr Phe Leu His His Asn Asp Glu Glu Thr Pro Trp Tyr
                245                 250                 255

Ala Asp Ser Glu Trp Thr Tyr Val Lys Gly Asn Leu Ser Ser Val Asp
            260                 265                 270

Arg Ser Tyr Gly Ala Leu Ile Asp Asn Leu Ser His Asn Ile Gly Thr
        275                 280                 285

His Gln Ile His His Leu Phe Pro Ile Ile Pro His Tyr Lys Leu Asn
    290                 295                 300

Asp Ala Thr Ala Ala Phe Ala Lys Ala Phe Pro Glu Leu Val Arg Lys
305                 310                 315                 320

Asn Ala Ala Pro Ile Ile Pro Thr Phe Phe Arg Met Ala Ala Met Tyr
                325                 330                 335

Ala Lys Tyr Gly Val Val Asp Thr Asp Ala Lys Thr Phe Thr Leu Lys

Glu Ala Lys Ala Ala Lys Thr Lys Ser Ser
       355                 360

<210> SEQ ID NO 3
<211> LENGTH: 359
<212> TYPE: PRT
<213> ORGANISM: Synechocystis sp. PCC 6803

<400> SEQUENCE: 3

Met Arg Leu Glu Ile Ser Ser Pro Gln Thr Lys Leu Pro Tyr Pro Lys
1               5                   10                  15

Thr Glu Glu Leu Pro Phe Thr Leu Gln Glu Leu Arg Asn Ala Ile Pro
            20                  25                  30

Ala Asp Cys Phe Glu Pro Ser Val Val Arg Ser Leu Gly Tyr Phe Phe
        35                  40                  45

Leu Asp Val Gly Leu Ile Ala Gly Phe Tyr Ala Leu Ala Ala Tyr Leu
    50                  55                  60

Asp Ser Trp Phe Phe Tyr Pro Ile Phe Trp Leu Ile Gln Gly Thr Leu
65                  70                  75                  80

Phe Trp Ser Leu Phe Val Val Gly His Asp Cys Gly His Gly Ser Phe
                85                  90                  95

Ser Lys Ser Lys Thr Leu Asn Asn Trp Ile Gly His Leu Ser His Thr
            100                 105                 110

Pro Ile Leu Val Pro Tyr His Gly Trp Arg Ile Ser His Arg Thr His
        115                 120                 125

His Ala Asn Thr Gly Asn Ile Asp Thr Asp Glu Ser Trp Tyr Pro Val
    130                 135                 140

Ser Glu Gln Lys Tyr Asn Gln Met Ala Trp Tyr Glu Lys Leu Leu Arg
145                 150                 155                 160

Phe Tyr Leu Pro Leu Ile Ala Tyr Pro Ile Tyr Leu Phe Arg Arg Ser
                165                 170                 175

Pro Asn Arg Gln Gly Ser His Phe Met Pro Gly Ser Pro Leu Phe Arg
            180                 185                 190

Pro Gly Glu Lys Ala Ala Val Leu Thr Ser Thr Phe Ala Leu Ala Ala
        195                 200                 205

Phe Val Gly Phe Leu Gly Phe Leu Thr Trp Gln Phe Gly Trp Leu Phe
    210                 215                 220

Leu Leu Lys Phe Tyr Val Ala Pro Tyr Leu Val Phe Val Val Trp Leu
225                 230                 235                 240

Asp Leu Val Thr Phe Leu His His Thr Glu Asp Asn Ile Pro Trp Tyr
                245                 250                 255

Arg Gly Asp Asp Trp Tyr Phe Leu Lys Gly Ala Leu Ser Thr Ile Asp
            260                 265                 270

Arg Asp Tyr Gly Phe Ile Asn Pro Ile His His Asp Ile Gly Thr His
        275                 280                 285

Val Ala His His Ile Phe Ser Asn Met Pro His Tyr Lys Leu Arg Arg
    290                 295                 300

Ala Thr Glu Ala Ile Lys Pro Ile Leu Gly Glu Tyr Tyr Arg Tyr Ser
305                 310                 315                 320

Asp Glu Pro Ile Trp Gln Ala Phe Lys Ser Tyr Trp Ala Cys His
                325                 330                 335

Phe Val Pro Asn Gln Gly Ser Gly Val Tyr Tyr Gln Ser Pro Ser Asn
            340                 345                 350

Gly Gly Tyr Gln Lys Lys Pro
        355

<210> SEQ ID NO 4
<211> LENGTH: 359
<212> TYPE: PRT
<213> ORGANISM: Nostoc punctiforme

<400> SEQUENCE: 4

Met Pro Ser Asn Ile Ile Thr Phe Asn Pro Leu Gly Ser Glu Lys
1               5                   10                  15

Ser Glu Asp Thr Thr Lys Leu Pro Phe Asn Leu Gln Asp Leu Lys Ala
                20                  25                  30

Ala Ile Pro Ala Glu Cys Phe Gln Pro Asn Val Lys Lys Ser Leu Phe
            35                  40                  45

Tyr Phe Phe Arg Asp Ile Leu Ile Ile Gly Leu Leu Tyr Ala Val Ala
    50                  55                  60

Ser Tyr Leu Asp Ser Trp Leu Phe Phe Pro Ile Phe Trp Leu Met Gln
65                  70                  75                  80

Gly Thr Met Phe Trp Ala Leu Phe Val Val Gly His Asp Cys Gly His
                85                  90                  95

Gln Ser Phe Ser Lys His Lys Trp Leu Asn Asp Leu Ile Gly His Leu
            100                 105                 110

Ser His Thr Pro Ile Leu Val Pro Tyr His Gly Trp Arg Ile Ser His
        115                 120                 125

Arg Thr His His Lys Asn Thr Gly Asn Ile Asp Asn Asp Glu Ser Trp
    130                 135                 140

Tyr Pro Val Ser Glu Ser Gln Tyr Lys Glu Met Pro Leu Ala Gln Lys
145                 150                 155                 160

Ile Gly Arg Tyr Tyr Val Phe Leu Leu Ala Tyr Pro Val Tyr Leu Phe
                165                 170                 175

Lys Arg Ser Pro Asn Lys Glu Gly Ser His Phe Leu Pro Gly Ser Ser
            180                 185                 190

Leu Phe Lys Pro Ser Glu Lys Trp Asp Val Ile Thr Ser Thr Val Leu
        195                 200                 205

Leu Ile Gly Met Val Gly Leu Leu Gly Phe Leu Thr Tyr Gln Trp Gly
    210                 215                 220

Trp Met Trp Leu Leu Lys Tyr Tyr Ala Val Pro Tyr Leu Val Phe Ile
225                 230                 235                 240

Val Trp Leu Asp Leu Val Thr Phe Leu His His Thr Glu Pro Glu Leu
                245                 250                 255

Pro Trp Tyr Arg Gly Glu Asp Trp Thr Phe Leu Lys Gly Ala Ile Ser
            260                 265                 270

Ser Ile Asp Arg Asp Tyr Gly Leu Val Asn His Ile His His Asp Ile
        275                 280                 285

Gly Thr His Val Ala His His Ile Phe Leu Asn Ile Pro His Tyr Asn
    290                 295                 300

Leu Leu Lys Ala Thr Glu Ala Ile Lys Pro Val Met Gly Glu Tyr Phe
305                 310                 315                 320

His Lys Ser Glu Glu Pro Ile Trp Lys Ser Leu Trp Asn Ser Cys Ile
                325                 330                 335

Ser Cys His Phe Val Pro Asp Thr Gly Ser Arg Val Tyr Tyr Thr Ser
            340                 345                 350

Asn Asn Lys Leu Ala Lys Asp
        355

```
<210> SEQ ID NO 5
<211> LENGTH: 358
<212> TYPE: PRT
<213> ORGANISM: Unknown
<220> FEATURE:
<223> OTHER INFORMATION: Variant of SEQ ID NO: 10

<400> SEQUENCE: 5

Met Ala Glu Asp Lys Thr Lys Val Glu Phe Pro Thr Leu Thr Glu Leu
1               5                   10                  15

Lys His Ser Ile Pro Asn Ala Cys Phe Glu Ser Asn Leu Gly Leu Ser
                20                  25                  30

Leu Tyr Tyr Thr Ala Arg Ala Ile Phe Asn Ala Ser Ala Ser Ala Ala
            35                  40                  45

Leu Leu Tyr Ala Ala Arg Ser Thr Pro Phe Ile Ala Asp Asn Val Leu
50                  55                  60

Leu His Ala Leu Val Cys Ala Thr Tyr Ile Tyr Val Gln Gly Val Ile
65                  70                  75                  80

Phe Trp Gly Phe Phe Thr Val Gly His Asp Cys Gly His Ser Ala Phe
                85                  90                  95

Ser Arg Tyr His Ser Val Asn Phe Ile Ile Gly Cys Ile Met His Ser
            100                 105                 110

Ala Ile Leu Thr Pro Phe Glu Ser Trp Arg Val Thr His Arg His His
            115                 120                 125

His Lys Asn Thr Gly Asn Ile Asp Lys Asp Glu Ile Phe Tyr Pro His
130                 135                 140

Arg Ser Val Lys Asp Leu Gln Asp Val Arg Gln Trp Val Tyr Thr Leu
145                 150                 155                 160

Gly Gly Ala Trp Phe Val Tyr Leu Lys Val Gly Tyr Ala Pro Arg Thr
                165                 170                 175

Met Ser His Phe Asp Pro Trp Asp Pro Leu Leu Leu Arg Arg Ala Ser
            180                 185                 190

Ala Val Ile Val Ser Leu Gly Val Trp Ala Ala Phe Phe Ala Ala Tyr
            195                 200                 205

Ala Tyr Leu Thr Tyr Ser Leu Gly Phe Ala Val Met Gly Leu Tyr Tyr
210                 215                 220

Tyr Ala Pro Leu Phe Val Phe Ala Ser Phe Leu Val Ile Thr Thr Phe
225                 230                 235                 240

Leu His His Asn Asp Glu Ala Thr Pro Trp Tyr Gly Asp Ser Glu Trp
                245                 250                 255

Thr Tyr Val Lys Gly Asn Leu Ser Ser Val Asp Arg Ser Tyr Gly Ala
            260                 265                 270

Phe Val Asp Asn Leu Ser His His Ile Gly Thr His Gln Val His His
            275                 280                 285

Leu Phe Pro Ile Ile Pro His Tyr Lys Leu Asn Glu Ala Thr Lys His
290                 295                 300

Phe Ala Ala Ala Tyr Pro His Leu Val Arg Arg Asn Asp Glu Pro Ile
305                 310                 315                 320

Ile Thr Ala Phe Phe Lys Thr Ala His Leu Phe Val Asn Tyr Gly Ala
                325                 330                 335

Val Pro Glu Thr Ala Gln Ile Phe Thr Leu Lys Glu Ser Ala Ala Ala
            340                 345                 350

Ala Lys Ala Lys Ser Asp
            355
```

<210> SEQ ID NO 6
<211> LENGTH: 10328
<212> TYPE: DNA
<213> ORGANISM: Yarrowia lipolytica

<400> SEQUENCE: 6

```
tatcacatca cgctctcatc aagaatactt cttgagaacc gtggagaccg gggttcgatt      60
ccccgtatcg gagtgtttat ttttttgctca accatacect ggggtgtgtt ctgtggagca    120
ttctcacttt tggtaaacga cattgcttca agtgcagcgg aatcaaaaag tataaagtgg    180
gcagcgagta tacctgtaca gactgtaggc gataactcaa tccaattacc ccccacaaca    240
tgactggcca aactgatctc aagactttat tgaaatcagc aacaccgatt ctcaatgaag    300
gcacatactt cttctgcaac attcacttga cgcctaaagt tggtgagaaa tggaccgaca    360
agacatattc tgctatccac ggactgttgc ctgtgtcggt ggctacaata cgtgagtcag    420
aagggctgac ggtggtggtt cgtacgttgt gtggaattgt gagcggataa caatttcaca    480
caggaaacag ctatgaccat gattacgcca agctcgaaat taaccctcac taaagggaac    540
aaaagctgga gctccaccgc ggacacaata tctggtcaaa tttcagtttc gttacataaa    600
tcgttatgtc aaaggagtgt gggaggttaa gagaattatc accggcaaac tatctgttaa    660
ttgctaggta cctctagacg tccacccggg tcgcttggcg gccgaagagg ccggaatctc    720
gggccgcggt ggcggccgct tactgcaact tccttgcctt ctccttggca gcgtcggcct    780
tggcctgctt ggccaacttg gcgttctttc tgtaaaagtt gtagaagaga ccgagcatgg    840
tccacatgta gaaccaaagc agagccgtga tgaagaaggg gtatccgggg cggccaagga    900
ccttcatggc gtacatgtcc caggaagact ggaccgacat catgcagaac tgtgtcatct    960
gcgagcgcgt gatgtagaac ttgatgaacg acacctgctt gaagcccaag gccgacaaga   1020
agtagtagcc gtacatgatc acatggatga acgagttcaa cgcagcagag aagtaggctt   1080
caccgttggg tgcaacaaag gtgaccaacc accagatggt gaagatggag ctgtggtggt   1140
aaacgtgcaa gaaggagatc tggcggttgt tcttcttgag gaccatgatc atggtgtcga   1200
caaactccat gatcttggag aagtagaaga gccagatcat cttggccata ggaagaccct   1260
tgaaggtatg atcagcagcg ttctcaaaca gtccatagtt ggcctgataa gcctcgtaca   1320
ggatcccacc gcacatgtag cgcctgatcg agaccagaca aaagttgtgc aggagcgaaa   1380
acgtcttgac ctcgaaccgc tcaaagttct tcatgatctg catgcccaca aagaccgtga   1440
ccaaataagc gagcacgatc aacagcacgt ggaacgggtt catcaacggc agctcacggg   1500
ccaaaggcga ctccaccgcg accaggaacc cacgcgtgtg atggacaatc gtgggatgt    1560
acttctcggc ctgggccacc agcgcggcct cgagaggatc gacatagggc gcggcccgga   1620
caccgatagc ggtggcaagg tccataaaca gatcttgcgg catctttgat gggaggaatg   1680
gcgcaatcga ctccatgcgg ccgctctaga actagtggat cctttgaatg attcttatac   1740
tcagaaggaa atgcttaacg atttcgggtg tgagttgaca aggagagaga gaaaagaaga   1800
ggaaaggtaa ttcggggacg gtggtctttt ataccttgg ctaaagtccc aaccacaaag   1860
caaaaaaatt ttcagtagtc tattttgcgt ccggcatggt ttacccggat ggccagacaa   1920
agaaactagt acaaagtctg aacaagcgta gattccagac tgcagtaccc tacgccctta   1980
acggcaagtg tgggaaccgg gggaggtttg atatgtgggg tgaaggggc tctcgccggg   2040
gttgggcccg ctactgggtc aatttggggt caattggggc aattgggct gttttttggg    2100
```

```
acacaaatac gccgccaacc cggtctctcc tgaagcttgt gagcggataa caatttcaca    2160
caggaaacag ctatgaccat gattacgcca agctcgaaat taaccctcac taaagggaac    2220
aaaagctgga gctccaccgc ggacacaata tctggtcaaa tttcagtttc gttacataaa    2280
tcgttatgtc aaaggagtgt gggaggttaa gagaattatc accggcaaac tatctgttaa    2340
ttgctaggta cctctagacg tccacccggg tcgcttggcg gccgaagagg ccggaatctc    2400 gggccgcgt ggcggccgcc tactcttcct tgggacggag tccaagaaca cgcaagtgct    2460
ccaaatgtga agcaaatgct tgccaaaacg tatccttgac aaggtatgga accttgtact    2520
cgctgcaggt gttcttgatg atggccagaa tatcgggata atggtgctgc gacacgttgg    2580
ggaacagatg gtgcacagcc tggtagttca agctgccagt gatgctggtc cagaggtgcg    2640
aatcgtgtgc gtaatcctgc gtagtctcga cctgcatagc tgcccagtcc ttttggatga    2700
tcccgttctc gtcaggcaac ggccactgaa cttcctcaac aacgtggttc gcctggaagg    2760
tcagcgccag ccagtaagac gacaccatgt ccgcgaccgt gaacaagagc agcaccttgc    2820
ccaggggcag atactgcagg ggaacaatca ggcgatacca gacaaagaaa gccttgccgc    2880
cccagaacat cacagtgtgc catgtcgaga tgggattgac acgaatagcg tcattggtct    2940
tgacaaagta caaaatgttg atgtcctgaa tgcgcaccTT gaacgccagc agtccgtaca    3000
ggaaaggaac aaacatgtgc tggttgatgt ggttgacaaa ccacttttgg ttgggcttga    3060
tacgacgaac atcgggctca gacgtcgaca cgtcgggatc tgctccagca atgttggtgt    3120
aggggtgatg gccgagcata tgttggtaca tccacaccag gtacgatgct ccgttgaaaa    3180
agtcgtgcgt ggctcccaga atcttccaga cagtgggtt gtgggtcact gaaaagtgag    3240
acgcatcatg aagagggttg agtccgactt gtgcgcacgc aaatcccatg atgattgcaa    3300
acaccacctg aagccatgtg cgttcgacaa cgaaaggcac aaagagctgc gcgtagtagg    3360
aagcgatcaa ggatccaaag ataagagcgt atcgtcccca gatctctggt ctattcttgg    3420
gatcaatgtt ccgatccgta aagtagccct cgactctcgt cttgatggtt ttgtggaaca    3480
ccgttggctc cgggaagatg gcagctcat tcgagaccag tgtaccgaca tagtacttct    3540
tcataatggc atctgcagcc ccaaacgcgt gatacatctc aaagaccgga gtaacatctc    3600
ggccagctcc gagcaggaga gtgtccactc caccaggatg gcggctcaag aactttgtga    3660
catcgtacac cctgccgcgg atggccaaga gtaggtcgtc cttggtgtta tgggccgcca    3720
gctcttccca ggtgaaggtt tttccttggt ccgttcccat ggtgaatgat tcttatactc    3780
agaaggaaat gcttaacgat ttcgggtgtg agttgacaag gagagagaga aaagaagagg    3840
aaaggtaatt cggggacggt ggtctttat acccttggct aaagtcccaa ccacaaagca    3900 aaaaatttt cagtagtcta ttttgcgtcc ggcatgggtt acccggatgg ccagacaaag    3960
aaactagtac aaagtctgaa caagcgtaga ttccagactg cagtacccta cgcccttaac    4020
ggcaagtgtg ggaaccgggg gaggtttgat atgtggggtg aaggggggctc tcgccggggt    4080 tgggcccgct actgggtcaa tttggggtca attggggcaa ttggggctgt tttttgggac    4140
acaaatacgc cgccaacccg gtctctcctg aattctgcag atgggctgca ggaattccgt    4200
cgtcgcctga tcgacatca tttatttacc agttggccac aaaccccttga cgatctcgta    4260 tgtccccTCc gacatactcc cggccggctg gggtacgttc gatagcgcta tcggcatcga    4320
caaggtttgg gtccctagcc gataccgcac tacctgagtc acaatcttcg gaggtttagt    4380
cttccacata gcacgggcaa aagtgcgtat atatacaaga gcgtttgcca gccacagatt    4440
ttcactccac acaccacatc acacatacaa ccacacacat ccacaatgga acccgaaact    4500
```

```
aagaagacca agactgactc caagaagatt gttcttctcg gcggcgactt ctgtggcccc   4560
gaggtgattg ccgaggccgt caaggtgctc aagtctgttg ctgaggcctc cggcaccgag   4620
tttgtgtttg aggaccgact cattggagga gctgccattg agaaggaggg cgagcccatc   4680
accgacgcta ctctcgacat ctgccgaaag gctgactcta ttatgctcgg tgctgtcgga   4740
ggcgctgcca acaccgtatg gaccactccc gacggacgaa ccgacgtgcg acccgagcag   4800
ggtctcctca agctgcgaaa ggacctgaac ctgtacgcca acctgcgacc ctgccagctg   4860
ctgtcgccca agctcgccga tctctccccc atccgaaacg ttgagggcac cgacttcatc   4920
attgtccgag agctcgtcgg aggtatctac tttggagagc gaaaggagga tgacggatct   4980
ggcgtcgctt ccgacaccga gacctactcc gttcctgagg ttgagcgaat tgcccgaatg   5040
gccgccttcc tggcccttca gcacaaccccc cctcttcccg tgtggtctct tgacaaggcc   5100
aacgtgctgg cctcctctcg actttggcga aagactgtca ctcgagtcct caaggacgaa   5160
ttcccccagc tcgagctcaa ccaccagctg atcgactcgg ccgccatgat cctcatcaag   5220
cagccctcca agatgaatgg tatcatcatc accaccaaca tgtttggcga tatcatctcc   5280
gacgaggcct ccgtcatccc cggttctctg ggtctgctgc cctccgcctc tctggcttct   5340
ctgcccgaca ccaacgaggc gttcggtctg tacgagccct gtcacggatc tgccccgat    5400 ctcggcaagc agaaggtcaa ccccattgcc accattctgt ctgccgccat gatgctcaag   5460
ttctctctta acatgaagcc cgccggtgac gctgttgagg ctgccgtcaa ggagtccgtc   5520
gaggctggta tcactaccgc cgatatcgga ggctcttcct ccacctccga ggtcggagac   5580
ttgttgccaa caaggtcaag gagctgctca agaaggagta agtcgtttct acgacgcatt   5640
gatggaagga gcaaactgac gcgcctgcgg gttggtctac cggcagggtc cgctagtgta   5700
taagactcta taaaagggc cctgccctgc taatgaaatg atgatttata atttaccggt    5760
gtagcaacct tgactagaag aagcagattg ggtgtgtttg tagtggagga cagtggtacg   5820
ttttggaaac agtcttcttg aaagtgtctt gtctacagta tattcactca taacctcaat   5880
agccaagggt gtagtcggtt tattaaagga agggagttgt ggctgatgtg gatagatatc   5940
tttaagctgg cgactgcacc caacgagtgt ggtggtagct tgttactgta tattcggtaa   6000
gatatatttt gtggggtttt agtggtgttt aaacgacgga attcctgcag cccatctgca   6060
gaattcagga gagaccgggt tggcggcgta tttgtgtccc aaaaaacagc cccaattgcc   6120
ccaattgacc ccaaattgac ccagtagcgg gcccaacccc ggcgagagcc cccttcaccc   6180
cacatatcaa acctcccccg gttcccacac ttgccgttaa gggcgtaggg tactgcagtc   6240
tggaatctac gcttgttcag actttgtact agtttctttg tctggccatc cgggtaaccc   6300
atgccggacg caaatagac tactgaaaat ttttttgctt tgtggttggg actttagcca    6360
agggtataaa agaccaccgt ccccgaatta cctttcctct tcttttctct ctctccttgt   6420
caactcacac ccgaaatcgt taagcatttc cttctgagta taagaatcat tcaccatggc   6480
tgaggataag accaaggtcg agttccctac cctgactgag ctgaagcact ctatccctaa   6540
cgcttgcttt gagtccaacc tcggactctc gctctactac actgcccgag cgatcttcaa   6600
cgcatctgcc tctgctgctc tgctctacgc tgcccgatct actcccttca ttgccgataa   6660
cgttctgctc cacgctctgg tttgcgccac ctacatctac gtgcagggtg tcatcttctg   6720
gggtttcttt accgtcggtc acgactgtgg tcactctgcc ttctcccgat accactccgt   6780
caacttcatc attggctgca tcatgcactc tgccattctg actcccttcg agtcctggcg   6840
```

```
agtgacccac cgacaccatc acaagaacac tggcaacatt gataaggacg agatcttcta    6900
ccctcatcgg tccgtcaagg acctccagga cgtgcgacaa tgggtctaca ccctcggagg    6960
tgcttggttt gtctacctga aggtcggata tgctcctcga accatgtccc actttgaccc    7020
ctgggaccct ctcctgcttc gacgagcctc cgctgtcatc gtgtccctcg gagtctgggc    7080
tgccttcttc gctgcctacg cctacctcac atactcgctc ggctttgccg tcatgggcct    7140
ctactactat gctcctctct tgtctttgc ttcgttcctc gtcattacta ccttcttgca     7200
tcacaacgac gaagctactc cctggtacgg tgactcggag tggacctacg tcaagggcaa    7260
cctgagctcc gtcgaccgat cgtacggagc tttcgtggac aacctgtctc accacattgg    7320
cacccaccag gtccatcact tgttccctat cattccccac tacaagctca acgaagccac    7380
caagcacttt gctgccgctt accctcacct cgtgagacgt aacgacgagc ccatcattac    7440
tgccttcttc aagaccgctc acctctttgt caactacgga gctgtgcccg agactgctca    7500
gattttcacc ctcaaagagt ctgccgctgc agccaaggcc aagagcgacc accaccatca    7560
ccaccattaa gcggccgcca ccgcggcccg agattccggc ctcttcggcc gccaagcgac    7620
ccgggtggac gtctagaggt acctagcaat taacagatag tttgccggtg ataattctct    7680
taacctccca cactcctttg acataacgat ttatgtaacg aaactgaaat ttgaccagat    7740
attgtgtccg cggtggagct ccagcttttg ttcccttta tgagggttaa tttcgagctt    7800
ggcgtaatcg atgcagaatt caggagagac cgggttggcg cgtatttgt gtcccaaaaa    7860
acagccccaa ttgccccaat tgaccccaaa ttgacccagt agcgggccca accccggcga    7920
gagccccctt caccccacat atcaaacctc ccccggttcc cacacttgcc gttaagggcg    7980
tagggtactg cagtctggaa tctacgcttg ttcagacttt gtactagttt ctttgtctgg    8040
ccatccgggt aacccatgcc ggacgcaaaa tagactacta aaatttttt tgctttgtgg    8100
ttgggacttt agccaagggt ataaaagacc accgtccccg aattaccttt cctcttcttt    8160
tctctctctc cttgtcaact cacacccgaa atcgttaagc atttccttct gagtataaga    8220
atcattcacc atggctgctg ctcccagtgt gaggacgttt actcgggccg aggttttgaa    8280
tgccgaggct ctgaatgagg gcaagaagga tgccgaggca cccttcttga tgatcatcga    8340
caacaaggtg tacgatgtcc gcgagttcgt ccctgatcat cccggtggaa gtgtgattct    8400
cacgcacgtt ggcaaggacg gcactgacgt ctttgacact tttcaccccg aggctgcttg    8460
ggagactctt gccaactttt acgttggtga tattgacgag agcgaccgcg atatcaagaa    8520
tgatgacttt gcgccgagg tccgcaagct gcgtaccttg ttccagtctc ttggttacta    8580
cgattcttcc aaggcatact acgccttcaa ggtctcgttc aacctctgca tctggggttt    8640
gtcgacggtc attgtggcca agtggggcca gacctcgacc ctcgccaacg tgctctcggc    8700
tgcgcttttg ggtctgttct ggcagcagtg cggatggttg gctcacgact ttttgcatca    8760
ccaggtcttc caggaccgtt tctgggtga tcttttcggc gccttcttgg gaggtgtctg    8820
ccagggcttc tcgtcctcgt ggtggaagga caagcacaac actcaccacg ccgccccaa    8880
cgtccacggc gaggatcccg acattgacac ccaccctctg ttgacctgga gtgagcatgc    8940
gttggagatg ttctcggatg tcccagatga ggagctgacc cgcatgtggt cgcgtttcat    9000
ggtcctgaac cagacctggt tttacttccc cattctctcg tttgcccgtc tctcctggtg    9060
cctccagtcc attctctttg tgctgcctaa cggtcaggcc cacaagccct cgggcgcgcg    9120
tgtgcccatc tcgttggtcg agcagctgtc gcttgcgatg cactgaccct ggtacctcgc    9180
caccatgttc ctgttcatca aggatcccgt caacatgctg gtgtacttt tggtgtcgca    9240
```

-continued

```
ggcggtgtgc ggaaacttgt tggccatcgt gttctcgctc aaccacaacg gtatgcctgt      9300
gatctcgaag gaggaggcgg tcgatatgga tttcttcacg aagcagatca tcacgggtcg      9360
tgatgtccac ccgggtctat ttgccaactg gttcacgggt ggattgaact atcagatcga      9420
gcaccacttg ttcccttcga tgcctcgcca caacttttca agatccagc ctgctgtcga       9480 gaccctgtgc aaaaagtaca atgtccgata ccacaccacc ggtatgatcg agggaactgc      9540
agaggtcttt agccgtctga cgaggtctc caaggctacc tccaagatgg gtaaggcgca       9600
gtaagcggcc gccaccgcgg cccgagattc cggcctcttc ggccgccaag cgacccgggt      9660
ggacgtctag aggtacctag caattaacag atagtttgcc ggtgataatt ctcttaacct      9720
cccacactcc tttgacataa cgatttatgt aacgaaactg aaatttgacc agatattgtg      9780
tccgcggtgg agctccagct tttgttccct ttagtgaggg ttaattaatt cgatatcata      9840
attgtcggcc gaggtctgta cggccagaac cgagatccta ttgaggaggc caagcgatac      9900
cagaaggctg gctgggaggc ttaccagaag attaactgtt agaggttaga ctatggtat       9960 gtcatttaac tgtgtatata gagagcgtgc aagtatggag cgcttgttca gcttgtatga     10020
tggtcagacg acctgtctga tcgagtatgt atgatactgc acaacctgtg tatccgcatg     10080
atctgtccaa tggggcatgt tgttgtgttt ctcgatacgg agatgctggg tacaagtagc     10140
taatacgatt gaactactta tacttatatg aggcttgaag aaagctgact tgtgtatgac     10200
ttattctcaa ctacatcccc agtcacaata ccaccactgc actaccacta caccaaaacc     10260
atgatcaaac cacccatgga cttcctggag gcagaagaac ttgttatgga aaagctcaag     10320
agagagaa                                                              10328
```

<210> SEQ ID NO 7
<211> LENGTH: 2001
<212> TYPE: DNA
<213> ORGANISM: Synechocystis sp. PCC 6803
<220> FEATURE:
<221> NAME/KEY: CDS
<222> LOCATION: (643)..(1722)

<400> SEQUENCE: 7

```
ccatccttgg gcaggattag tgttttggtg ggcggcccta gaaagacagg tacgggtgga       60
tggtcaagtg gaaaaaattg atccggcaga atccgatgcc tattttcagt cccgtccccg      120
gggttctcaa ttgggggcct gggcttctcc ccaaagtcgg attgttggcg atcgccagga      180
gttagaagac aatctagccc gttgggaaaa acaatacgaa aaccaatcca ttccccgccc      240
cccccactgg ggaggatttc gagtgattcc ccatcgcatc gaattttggc aaggccgccc      300
tagtcgtctc catgaccgtt tgcaatttaa tttgcttgat ggtcaatggc acagacagag      360
gttggcgccg tagaagttaa actagccccc attccattgc agtcttaaag ttttgacgtt      420
ttagtccata aagttgatca gagttgcgta tttataaaca tttgaacttt ttatcgtcct      480
ttctctacac aaatttgaat caagtattct ccttagtgtg ttttctgtct tagtcaaaat      540
tggtcttact gccgaatttt catcttccaa cggcagcctt ctttgaagat ttaggataga      600
atcataggat tgttttgccg tcatagcccc taagataaat ac gtg cgt cta gaa           654
                                              Val Arg Leu Glu
                                                1 att tca tcg cct caa aca aag ctt cct tac ccc aaa act gaa gaa tta         702
Ile Ser Ser Pro Gln Thr Lys Leu Pro Tyr Pro Lys Thr Glu Glu Leu
  5              10                  15                  20 cca ttt acc ctc caa gag ctc aga aac gct att cca gcg gat tgt ttt         750
```

```
Pro Phe Thr Leu Gln Glu Leu Arg Asn Ala Ile Pro Ala Asp Cys Phe
            25                  30                  35 gag cca tcg gta gtc cgg tcc ttg ggc tac ttt ttt ttg gat gtt ggt       798
Glu Pro Ser Val Val Arg Ser Leu Gly Tyr Phe Phe Leu Asp Val Gly
            40                  45                  50 tta att gcc ggg ttt tat gct cta gcg gcc tac ctt gat tcc tgg ttc       846
Leu Ile Ala Gly Phe Tyr Ala Leu Ala Ala Tyr Leu Asp Ser Trp Phe
            55                  60                  65 ttc tat ccg att ttt tgg tta att cag gga acc cta ttc tgg tcc ctg       894
Phe Tyr Pro Ile Phe Trp Leu Ile Gln Gly Thr Leu Phe Trp Ser Leu
        70                  75                  80 ttt gtg gtg ggc cat gat tgt ggc cat ggc tcc ttt tcc aaa tcc aaa       942
Phe Val Val Gly His Asp Cys Gly His Gly Ser Phe Ser Lys Ser Lys
85                  90                  95                 100 acc ctt aat aat tgg att ggt cat ctc agc cac acg cca att ttg gtg       990
Thr Leu Asn Asn Trp Ile Gly His Leu Ser His Thr Pro Ile Leu Val
                105                 110                 115 cct tac cat ggc tgg cgt att agt cat cgt act cac cat gcc aac acg      1038
Pro Tyr His Gly Trp Arg Ile Ser His Arg Thr His His Ala Asn Thr
                120                 125                 130 ggc aat atc gac acc gac gaa agt tgg tat cca gtg tcg gag caa aaa      1086
Gly Asn Ile Asp Thr Asp Glu Ser Trp Tyr Pro Val Ser Glu Gln Lys
            135                 140                 145 tat aac caa atg gcc tgg tat gaa aaa ctt cta cgt ttt tac ttg cct      1134
Tyr Asn Gln Met Ala Trp Tyr Glu Lys Leu Leu Arg Phe Tyr Leu Pro
150                 155                 160 ctg atc gcc tac ccc att tat cta ttt cgg cga tcg cca aac cgg caa      1182
Leu Ile Ala Tyr Pro Ile Tyr Leu Phe Arg Arg Ser Pro Asn Arg Gln
165                 170                 175                 180 ggc tcc cat ttc atg ccc ggc agt ccc cta ttc cgt ccc gga gaa aaa      1230
Gly Ser His Phe Met Pro Gly Ser Pro Leu Phe Arg Pro Gly Glu Lys
                185                 190                 195 gca gct gtt ctc acc agc acc ttt gcc ctt gca gcc ttt gtc ggc ttc      1278
Ala Ala Val Leu Thr Ser Thr Phe Ala Leu Ala Ala Phe Val Gly Phe
            200                 205                 210 ctt ggc ttt tta act tgg caa ttt ggc tgg cta ttt ttg ctg aaa ttt      1326
Leu Gly Phe Leu Thr Trp Gln Phe Gly Trp Leu Phe Leu Leu Lys Phe
            215                 220                 225 tat gtt gcc ccc tac ctc gtg ttt gtg gtg tgg tta gat ttg gtc aca      1374
Tyr Val Ala Pro Tyr Leu Val Phe Val Val Trp Leu Asp Leu Val Thr
            230                 235                 240 ttt tta cat cac act gaa gac aat atc cct tgg tat cgt ggt gat gac      1422
Phe Leu His His Thr Glu Asp Asn Ile Pro Trp Tyr Arg Gly Asp Asp
245                 250                 255                 260 tgg tat ttt ctc aaa ggt gcc ctc tcc acc att gat cgg gat tac ggc      1470
Trp Tyr Phe Leu Lys Gly Ala Leu Ser Thr Ile Asp Arg Asp Tyr Gly
                265                 270                 275 ttc att aac ccc att cac cat gac att ggc acc cac gtc gcc cac cat      1518
Phe Ile Asn Pro Ile His His Asp Ile Gly Thr His Val Ala His His
            280                 285                 290 att ttc tcg aat atg ccc cac tac aag tta cgc cgg gcg act gaa gcc      1566
Ile Phe Ser Asn Met Pro His Tyr Lys Leu Arg Arg Ala Thr Glu Ala
            295                 300                 305 atc aag ccc att tta ggg gaa tat tat cga tat tct gac gag cca att      1614
Ile Lys Pro Ile Leu Gly Glu Tyr Tyr Arg Tyr Ser Asp Glu Pro Ile
310                 315                 320 tgg caa gct ttt ttt aag tcc tac tgg gct tgc cat ttt gtt cct aat      1662
Trp Gln Ala Phe Phe Lys Ser Tyr Trp Ala Cys His Phe Val Pro Asn
325                 330                 335                 340
```

-continued

```
caa ggt tca ggg gtc tat tac caa tcc cca tcc aat ggt gga tat caa    1710
Gln Gly Ser Gly Val Tyr Tyr Gln Ser Pro Ser Asn Gly Gly Tyr Gln
            345                 350                 355 aag aaa cct taa ttgatcctaa ttgaatcaaa ccaacatcgg gagggaaggc        1762
Lys Lys Pro aatattagat ggtattactc ccttccgatc gccttatgag aagtatggaa gaagttaaac  1822
aatcacactc caaaagatca gcattaaacc aacaacggtg ctgtggtgag cagaagatt   1882 gaaaaaggat tgtttaccta actgttgact gagaaaaatc gaccaaagta ccccggccaa  1942
aagcagcata ccttgcaaaa aggcgatcgc cgctggatcc gccaccaaca tcggtaaat   2001

<210> SEQ ID NO 8
<211> LENGTH: 359
<212> TYPE: PRT
<213> ORGANISM: Synechocystis sp. PCC 6803

<400> SEQUENCE: 8

Val Arg Leu Glu Ile Ser Ser Pro Gln Thr Lys Leu Pro Tyr Pro Lys
1               5                   10                  15

Thr Glu Glu Leu Pro Phe Thr Leu Gln Glu Leu Arg Asn Ala Ile Pro
                20                  25                  30

Ala Asp Cys Phe Glu Pro Ser Val Arg Ser Leu Gly Tyr Phe Phe
            35                  40                  45

Leu Asp Val Gly Leu Ile Ala Gly Phe Tyr Ala Leu Ala Ala Tyr Leu
50                  55                  60

Asp Ser Trp Phe Phe Tyr Pro Ile Phe Trp Leu Ile Gln Gly Thr Leu
65                  70                  75                  80

Phe Trp Ser Leu Phe Val Val Gly His Asp Cys Gly His Gly Ser Phe
                85                  90                  95

Ser Lys Ser Lys Thr Leu Asn Asn Trp Ile Gly His Leu Ser His Thr
            100                 105                 110

Pro Ile Leu Val Pro Tyr His Gly Trp Arg Ile Ser His Arg Thr His
        115                 120                 125

His Ala Asn Thr Gly Asn Ile Asp Thr Asp Glu Ser Trp Tyr Pro Val
    130                 135                 140

Ser Glu Gln Lys Tyr Asn Gln Met Ala Trp Tyr Glu Lys Leu Leu Arg
145                 150                 155                 160

Phe Tyr Leu Pro Leu Ile Ala Tyr Pro Ile Tyr Leu Phe Arg Arg Ser
                165                 170                 175

Pro Asn Arg Gln Gly Ser His Phe Met Pro Gly Ser Pro Leu Phe Arg
            180                 185                 190

Pro Gly Glu Lys Ala Ala Val Leu Thr Ser Thr Phe Ala Leu Ala Ala
        195                 200                 205

Phe Val Gly Phe Leu Gly Phe Leu Thr Trp Gln Phe Gly Trp Leu Phe
    210                 215                 220

Leu Leu Lys Phe Tyr Val Ala Pro Tyr Leu Val Phe Val Val Trp Leu
225                 230                 235                 240

Asp Leu Val Thr Phe Leu His His Thr Glu Asp Asn Ile Pro Trp Tyr
                245                 250                 255

Arg Gly Asp Asp Trp Tyr Phe Leu Lys Gly Ala Leu Ser Thr Ile Asp
            260                 265                 270

Arg Asp Tyr Gly Phe Ile Asn Pro Ile His His Asp Ile Gly Thr His
        275                 280                 285

Val Ala His His Ile Phe Ser Asn Met Pro His Tyr Lys Leu Arg Arg
    290                 295                 300
```

| | | | | | | | | | | | | |
|---|---|---|---|---|---|---|---|---|---|---|---|---|
| Ala | Thr | Glu | Ala | Ile | Lys | Pro | Ile | Leu | Gly | Glu | Tyr | Tyr | Arg | Tyr | Ser |
| 305 | | | | 310 | | | | | 315 | | | | | 320 | |
| Asp | Glu | Pro | Ile | Trp | Gln | Ala | Phe | Phe | Lys | Ser | Tyr | Trp | Ala | Cys | His |
| | | | | 325 | | | | | 330 | | | | | 335 | |
| Phe | Val | Pro | Asn | Gln | Gly | Ser | Gly | Val | Tyr | Tyr | Gln | Ser | Pro | Ser | Asn |
| | | | 340 | | | | | 345 | | | | | 350 | | |
| Gly | Gly | Tyr | Gln | Lys | Lys | Pro | | | | | | | | | |
| | | | | 355 | | | | | | | | | | | |

<210> SEQ ID NO 9
<211> LENGTH: 1077
<212> TYPE: DNA
<213> ORGANISM: Saprolegnia diclina
<220> FEATURE:
<221> NAME/KEY: CDS
<222> LOCATION: (1)..(1077)

<400> SEQUENCE: 9

| | | | | | | | | | | | | | | | | |
|---|---|---|---|---|---|---|---|---|---|---|---|---|---|---|---|---|
| atg | act | gag | gat | aag | acg | aag | gtc | gag | ttc | ccg | acg | ctc | acg | gag | ctc | 48 |
| Met | Thr | Glu | Asp | Lys | Thr | Lys | Val | Glu | Phe | Pro | Thr | Leu | Thr | Glu | Leu | |
| 1 | | | | 5 | | | | | 10 | | | | | 15 | | |
| aag | cac | tcg | atc | ccg | aac | gcg | tgc | ttt | gag | tcg | aac | ctc | ggc | ctc | tcg | 96 |
| Lys | His | Ser | Ile | Pro | Asn | Ala | Cys | Phe | Glu | Ser | Asn | Leu | Gly | Leu | Ser | |
| | | | 20 | | | | | 25 | | | | | 30 | | | |
| ctc | tac | tac | acg | gcc | cgc | gcg | atc | ttc | aac | gcg | tcg | gcc | tcg | gcg | gcg | 144 |
| Leu | Tyr | Tyr | Thr | Ala | Arg | Ala | Ile | Phe | Asn | Ala | Ser | Ala | Ser | Ala | Ala | |
| | | 35 | | | | | 40 | | | | | 45 | | | | |
| ctg | ctc | tac | gcg | gcg | cgc | tcg | acg | ccg | ttc | att | gcc | gat | aac | gtt | ctg | 192 |
| Leu | Leu | Tyr | Ala | Ala | Arg | Ser | Thr | Pro | Phe | Ile | Ala | Asp | Asn | Val | Leu | |
| 50 | | | | | 55 | | | | | 60 | | | | | | |
| ctc | cac | gcg | ctc | gtt | tgc | gcc | acc | tac | atc | tac | gtg | cag | ggc | gtc | atc | 240 |
| Leu | His | Ala | Leu | Val | Cys | Ala | Thr | Tyr | Ile | Tyr | Val | Gln | Gly | Val | Ile | |
| 65 | | | | | 70 | | | | | 75 | | | | | 80 | |
| ttc | tgg | ggc | ttc | ttc | acg | gtc | ggc | cac | gac | tgc | ggc | cac | tcg | gcc | ttc | 288 |
| Phe | Trp | Gly | Phe | Phe | Thr | Val | Gly | His | Asp | Cys | Gly | His | Ser | Ala | Phe | |
| | | | | 85 | | | | | 90 | | | | | 95 | | |
| tcg | cgc | tac | cac | agc | gtc | aac | ttt | atc | atc | ggc | tgc | atc | atg | cac | tct | 336 |
| Ser | Arg | Tyr | His | Ser | Val | Asn | Phe | Ile | Ile | Gly | Cys | Ile | Met | His | Ser | |
| | | | 100 | | | | | 105 | | | | | 110 | | | |
| gcg | att | ttg | acg | ccg | ttc | gag | agc | tgg | cgc | gtg | acg | cac | cgc | cac | cac | 384 |
| Ala | Ile | Leu | Thr | Pro | Phe | Glu | Ser | Trp | Arg | Val | Thr | His | Arg | His | His | |
| | | 115 | | | | | 120 | | | | | 125 | | | | |
| cac | aag | aac | acg | ggc | aac | att | gat | aag | gac | gag | atc | ttt | tac | ccg | cac | 432 |
| His | Lys | Asn | Thr | Gly | Asn | Ile | Asp | Lys | Asp | Glu | Ile | Phe | Tyr | Pro | His | |
| 130 | | | | | 135 | | | | | 140 | | | | | | |
| cgg | tcg | gtc | aag | gac | ctc | cag | gac | gtg | cgc | caa | tgg | gtc | tac | acg | ctc | 480 |
| Arg | Ser | Val | Lys | Asp | Leu | Gln | Asp | Val | Arg | Gln | Trp | Val | Tyr | Thr | Leu | |
| 145 | | | | | 150 | | | | | 155 | | | | | 160 | |
| ggc | ggt | gcg | tgg | ttt | gtc | tac | ttg | aag | gtc | ggg | tat | gcc | ccg | cgc | acg | 528 |
| Gly | Gly | Ala | Trp | Phe | Val | Tyr | Leu | Lys | Val | Gly | Tyr | Ala | Pro | Arg | Thr | |
| | | | | 165 | | | | | 170 | | | | | 175 | | |
| atg | agc | cac | ttt | gac | ccg | tgg | gac | ccg | ctc | ctc | ctt | cgc | cgc | gcg | tcg | 576 |
| Met | Ser | His | Phe | Asp | Pro | Trp | Asp | Pro | Leu | Leu | Leu | Arg | Arg | Ala | Ser | |
| | | | 180 | | | | | 185 | | | | | 190 | | | |
| gcc | gtc | atc | gtg | tcg | ctc | ggc | gtc | tgg | gcc | gcc | ttc | ttc | gcc | gcg | tac | 624 |
| Ala | Val | Ile | Val | Ser | Leu | Gly | Val | Trp | Ala | Ala | Phe | Phe | Ala | Ala | Tyr | |
| | | 195 | | | | | 200 | | | | | 205 | | | | |
| gcg | tac | ctc | aca | tac | tcg | ctc | ggc | ttt | gcc | gtc | atg | ggc | ctc | tac | tac | 672 |
| Ala | Tyr | Leu | Thr | Tyr | Ser | Leu | Gly | Phe | Ala | Val | Met | Gly | Leu | Tyr | Tyr | |
| 210 | | | | | 215 | | | | | 220 | | | | | | |

-continued

| | | | | | | | | | | | | | | | | |
|---|---|---|---|---|---|---|---|---|---|---|---|---|---|---|---|---|
| tat | gcg | ccg | ctc | ttt | gtc | ttt | gct | tcg | ttc | ctc | gtc | att | acg | acc | ttc | 720 |
| Tyr | Ala | Pro | Leu | Phe | Val | Phe | Ala | Ser | Phe | Leu | Val | Ile | Thr | Thr | Phe | |
| 225 | | | | 230 | | | | | 235 | | | | | 240 | | |

| | | | | | | | | | | | | | | | |
|---|---|---|---|---|---|---|---|---|---|---|---|---|---|---|---|
| ttg | cac | cac | aac | gac | gaa | gcg | acg | ccg | tgg | tac | ggc | gac | tcg | gag | tgg | 768 |
| Leu | His | His | Asn | Asp | Glu | Ala | Thr | Pro | Trp | Tyr | Gly | Asp | Ser | Glu | Trp | |
| | | | | 245 | | | | | 250 | | | | | 255 | | |

| acg | tac | gtc | aag | ggc | aac | ctc | tcg | agc | gtc | gac | cgc | tcg | tac | ggc | gcg | 816 |
| Thr | Tyr | Val | Lys | Gly | Asn | Leu | Ser | Ser | Val | Asp | Arg | Ser | Tyr | Gly | Ala | |
| | | | 260 | | | | | 265 | | | | | 270 | | | |

| ttc | gtg | gac | aac | ctg | agc | cac | cac | att | ggc | acg | cac | cag | gtc | cac | cac | 864 |
| Phe | Val | Asp | Asn | Leu | Ser | His | His | Ile | Gly | Thr | His | Gln | Val | His | His | |
| | | 275 | | | | | 280 | | | | | 285 | | | | |

| ttg | ttc | ccg | atc | att | ccg | cac | tac | aag | ctc | aac | gaa | gcc | acc | aag | cac | 912 |
| Leu | Phe | Pro | Ile | Ile | Pro | His | Tyr | Lys | Leu | Asn | Glu | Ala | Thr | Lys | His | |
| 290 | | | | | 295 | | | | | 300 | | | | | | |

| ttt | gcg | gcc | gcg | tac | ccg | cac | ctc | gtg | cgc | agg | aac | gac | gag | ccc | atc | 960 |
| Phe | Ala | Ala | Ala | Tyr | Pro | His | Leu | Val | Arg | Arg | Asn | Asp | Glu | Pro | Ile | |
| 305 | | | | 310 | | | | | 315 | | | | | 320 | | |

| atc | acg | gcc | ttc | ttc | aag | acc | gcg | cac | ctc | ttt | gtc | aac | tac | ggc | gct | 1008 |
| Ile | Thr | Ala | Phe | Phe | Lys | Thr | Ala | His | Leu | Phe | Val | Asn | Tyr | Gly | Ala | |
| | | | | 325 | | | | | 330 | | | | | 335 | | |

| gtg | ccc | gag | acg | gcg | cag | atc | ttc | acg | ctc | aaa | gag | tcg | gcc | gcg | gcc | 1056 |
| Val | Pro | Glu | Thr | Ala | Gln | Ile | Phe | Thr | Leu | Lys | Glu | Ser | Ala | Ala | Ala | |
| | | | 340 | | | | | 345 | | | | | 350 | | | |

| gcc | aag | gcc | aag | tcg | gac | taa | | | | | | | | | | 1077 |
| Ala | Lys | Ala | Lys | Ser | Asp | | | | | | | | | | | |
| | | 355 | | | | | | | | | | | | | | |

<210> SEQ ID NO 10
<211> LENGTH: 358
<212> TYPE: PRT
<213> ORGANISM: Saprolegnia diclina

<400> SEQUENCE: 10

Met Thr Glu Asp Lys Thr Lys Val Glu Phe Pro Thr Leu Thr Glu Leu
1               5                   10                  15

Lys His Ser Ile Pro Asn Ala Cys Phe Glu Ser Asn Leu Gly Leu Ser
            20                  25                  30

Leu Tyr Tyr Thr Ala Arg Ala Ile Phe Asn Ala Ser Ala Ser Ala Ala
        35                  40                  45

Leu Leu Tyr Ala Ala Arg Ser Thr Pro Phe Ile Ala Asp Asn Val Leu
    50                  55                  60

Leu His Ala Leu Val Cys Ala Thr Tyr Ile Tyr Val Gln Gly Val Ile
65                  70                  75                  80

Phe Trp Gly Phe Phe Thr Val Gly His Asp Cys Gly His Ser Ala Phe
                85                  90                  95

Ser Arg Tyr His Ser Val Asn Phe Ile Ile Gly Cys Ile Met His Ser
            100                 105                 110

Ala Ile Leu Thr Pro Phe Glu Ser Trp Arg Val Thr His Arg His His
        115                 120                 125

His Lys Asn Thr Gly Asn Ile Asp Lys Asp Glu Ile Phe Tyr Pro His
    130                 135                 140

Arg Ser Val Lys Asp Leu Gln Asp Val Arg Gln Trp Val Tyr Thr Leu
145                 150                 155                 160

Gly Gly Ala Trp Phe Val Tyr Leu Lys Val Gly Tyr Ala Pro Arg Thr
                165                 170                 175

Met Ser His Phe Asp Pro Trp Asp Pro Leu Leu Leu Arg Arg Ala Ser

```
                  180                 185                 190
Ala Val Ile Val Ser Leu Gly Val Trp Ala Ala Phe Phe Ala Ala Tyr
            195                 200                 205

Ala Tyr Leu Thr Tyr Ser Leu Gly Phe Ala Val Met Gly Leu Tyr Tyr
        210                 215                 220

Tyr Ala Pro Leu Phe Val Phe Ala Ser Phe Leu Val Ile Thr Thr Phe
225                 230                 235                 240

Leu His His Asn Asp Glu Ala Thr Pro Trp Tyr Gly Asp Ser Glu Trp
                245                 250                 255

Thr Tyr Val Lys Gly Asn Leu Ser Ser Val Asp Arg Ser Tyr Gly Ala
            260                 265                 270

Phe Val Asp Asn Leu Ser His His Ile Gly Thr His Gln Val His His
        275                 280                 285

Leu Phe Pro Ile Ile Pro His Tyr Lys Leu Asn Glu Ala Thr Lys His
    290                 295                 300

Phe Ala Ala Ala Tyr Pro His Leu Val Arg Arg Asn Asp Glu Pro Ile
305                 310                 315                 320

Ile Thr Ala Phe Phe Lys Thr Ala His Leu Phe Val Asn Tyr Gly Ala
                325                 330                 335

Val Pro Glu Thr Ala Gln Ile Phe Thr Leu Lys Glu Ser Ala Ala Ala
            340                 345                 350

Ala Lys Ala Lys Ser Asp
        355

<210> SEQ ID NO 11
<211> LENGTH: 1086
<212> TYPE: DNA
<213> ORGANISM: Phytophthora infestans
<220> FEATURE:
<221> NAME/KEY: CDS
<222> LOCATION: (1)..(1086)

<400> SEQUENCE: 11 atg gcg acg aag gag gcg tat gtg ttc ccc act ctg acg gag atc aag      48
Met Ala Thr Lys Glu Ala Tyr Val Phe Pro Thr Leu Thr Glu Ile Lys
1               5                   10                  15 cgg tcg cta cct aaa gac tgt ttc gag gct tcg gtg cct ctg tcg ctc      96
Arg Ser Leu Pro Lys Asp Cys Phe Glu Ala Ser Val Pro Leu Ser Leu
            20                  25                  30 tac tac acc gtg cgt tgt ctg gtg atc gcg gtg gct cta acc ttc ggt     144
Tyr Tyr Thr Val Arg Cys Leu Val Ile Ala Val Ala Leu Thr Phe Gly
        35                  40                  45 ctc aac tac gct cgc gct ctg ccc gag gtc gag agc ttc tgg gct ctg     192
Leu Asn Tyr Ala Arg Ala Leu Pro Glu Val Glu Ser Phe Trp Ala Leu
    50                  55                  60 gac gcc gca ctc tgc acg ggc tac atc ttg ctg cag ggc atc gtg ttc     240
Asp Ala Ala Leu Cys Thr Gly Tyr Ile Leu Leu Gln Gly Ile Val Phe
65                  70                  75                  80 tgg ggc ttc ttc acg gtg ggc cac gat gcc ggc cac ggc gcc ttc tcg     288
Trp Gly Phe Phe Thr Val Gly His Asp Ala Gly His Gly Ala Phe Ser
                85                  90                  95 cgc tac cac ctg ctt aac ttc gtg gtg ggc act ttc atg cac tcg ctc     336
Arg Tyr His Leu Leu Asn Phe Val Val Gly Thr Phe Met His Ser Leu
            100                 105                 110 atc ctc acg ccc ttc gag tcg tgg aag ctc acg cac cgt cac cac cac     384
Ile Leu Thr Pro Phe Glu Ser Trp Lys Leu Thr His Arg His His His
        115                 120                 125 aag aac acg ggc aac att gac cgt gac gag gtc ttc tac ccg caa cgc     432
```

```
Lys Asn Thr Gly Asn Ile Asp Arg Asp Glu Val Phe Tyr Pro Gln Arg
    130                 135                 140 aag gcc gac gac cac ccg ctg tct cgc aac ctg att ctg gcg ctc ggg      480
Lys Ala Asp Asp His Pro Leu Ser Arg Asn Leu Ile Leu Ala Leu Gly
145                 150                 155                 160 gca gcg tgg ctc gcc tat ttg gtc gag ggc ttc cct cct cgt aag gtc      528
Ala Ala Trp Leu Ala Tyr Leu Val Glu Gly Phe Pro Pro Arg Lys Val
                165                 170                 175 aac cac ttc aac ccg ttc gag cct ctg ttc gtg cgt cag gtg tca gct      576
Asn His Phe Asn Pro Phe Glu Pro Leu Phe Val Arg Gln Val Ser Ala
            180                 185                 190 gta gta atc tct ctt ctc gcc cac ttc ttc gtg gcc gga ctc tcc atc      624
Val Val Ile Ser Leu Leu Ala His Phe Phe Val Ala Gly Leu Ser Ile
        195                 200                 205 tat ctg agc ctc cag ctg ggc ctt aag acg atg gca atc tac tac tat      672
Tyr Leu Ser Leu Gln Leu Gly Leu Lys Thr Met Ala Ile Tyr Tyr Tyr
    210                 215                 220 gga cct gtt ttt gtg ttc ggc agc atg ctg gtc att acc acc ttc cta      720
Gly Pro Val Phe Val Phe Gly Ser Met Leu Val Ile Thr Thr Phe Leu
225                 230                 235                 240 cac cac aat gat gag gag acc cca tgg tac gcc gac tcg gag tgg acg      768
His His Asn Asp Glu Glu Thr Pro Trp Tyr Ala Asp Ser Glu Trp Thr
                245                 250                 255 tac gtc aag ggc aac ctc tcg tcc gtg gac cga tcg tac ggc gcg ctc      816
Tyr Val Lys Gly Asn Leu Ser Ser Val Asp Arg Ser Tyr Gly Ala Leu
            260                 265                 270 att gac aac ctg agc cac aac atc ggc acg cac cag atc cac cac ctt      864
Ile Asp Asn Leu Ser His Asn Ile Gly Thr His Gln Ile His His Leu
        275                 280                 285 ttc cct atc att ccg cac tac aaa ctc aag aaa gcc act gcg gcc ttc      912
Phe Pro Ile Ile Pro His Tyr Lys Leu Lys Lys Ala Thr Ala Ala Phe
    290                 295                 300 cac cag gct ttc cct gag ctc gtg cgc aag agc gac gag cca att atc      960
His Gln Ala Phe Pro Glu Leu Val Arg Lys Ser Asp Glu Pro Ile Ile
305                 310                 315                 320 aag gct ttc ttc cgg gtt gga cgt ctc tac gca aac tac ggc gtt gtg     1008
Lys Ala Phe Phe Arg Val Gly Arg Leu Tyr Ala Asn Tyr Gly Val Val
                325                 330                 335 gac cag gag gcg aag ctc ttc acg cta aag gaa gcc aag gcg gcg acc     1056
Asp Gln Glu Ala Lys Leu Phe Thr Leu Lys Glu Ala Lys Ala Ala Thr
            340                 345                 350 gag gcg gcg gcc aag acc aag tcc acg taa                             1086
Glu Ala Ala Ala Lys Thr Lys Ser Thr
        355                 360

<210> SEQ ID NO 12
<211> LENGTH: 361
<212> TYPE: PRT
<213> ORGANISM: Phytophthora infestans

<400> SEQUENCE: 12

Met Ala Thr Lys Glu Ala Tyr Val Phe Pro Thr Leu Thr Glu Ile Lys
1               5                   10                  15

Arg Ser Leu Pro Lys Asp Cys Phe Glu Ala Ser Val Pro Leu Ser Leu
            20                  25                  30

Tyr Tyr Thr Val Arg Cys Leu Val Ile Ala Val Ala Leu Thr Phe Gly
        35                  40                  45

Leu Asn Tyr Ala Arg Ala Leu Pro Glu Val Glu Ser Phe Trp Ala Leu
    50

```
Asp Ala Ala Leu Cys Thr Gly Tyr Ile Leu Leu Gln Gly Ile Val Phe
 65                  70                  75                  80

Trp Gly Phe Phe Thr Val Gly His Asp Ala Gly His Gly Ala Phe Ser
             85                  90                  95

Arg Tyr His Leu Leu Asn Phe Val Val Gly Thr Phe Met His Ser Leu
            100                 105                 110

Ile Leu Thr Pro Phe Glu Ser Trp Lys Leu Thr His Arg His His His
        115                 120                 125

Lys Asn Thr Gly Asn Ile Asp Arg Asp Glu Val Phe Tyr Pro Gln Arg
    130                 135                 140

Lys Ala Asp His Pro Leu Ser Arg Asn Leu Ile Leu Ala Leu Gly
145                 150                 155                 160

Ala Ala Trp Leu Ala Tyr Leu Val Glu Gly Phe Pro Pro Arg Lys Val
                165                 170                 175

Asn His Phe Asn Pro Phe Glu Pro Leu Phe Val Arg Gln Val Ser Ala
            180                 185                 190

Val Val Ile Ser Leu Leu Ala His Phe Phe Val Ala Gly Leu Ser Ile
        195                 200                 205

Tyr Leu Ser Leu Gln Leu Gly Leu Lys Thr Met Ala Ile Tyr Tyr Tyr
    210                 215                 220

Gly Pro Val Phe Val Phe Gly Ser Met Leu Val Ile Thr Thr Phe Leu
225                 230                 235                 240

His His Asn Asp Glu Glu Thr Pro Trp Tyr Ala Asp Ser Glu Trp Thr
                245                 250                 255

Tyr Val Lys Gly Asn Leu Ser Ser Val Asp Arg Ser Tyr Gly Ala Leu
            260                 265                 270

Ile Asp Asn Leu Ser His Asn Ile Gly Thr His Gln Ile His His Leu
        275                 280                 285

Phe Pro Ile Ile Pro His Tyr Lys Leu Lys Ala Thr Ala Ala Phe
    290                 295                 300

His Gln Ala Phe Pro Glu Leu Val Arg Lys Ser Asp Glu Pro Ile Ile
305                 310                 315                 320

Lys Ala Phe Phe Arg Val Gly Arg Leu Tyr Ala Asn Tyr Gly Val Val
                325                 330                 335

Asp Gln Glu Ala Lys Leu Phe Thr Leu Lys Glu Ala Lys Ala Ala Thr
            340                 345                 350

Glu Ala Ala Ala Lys Thr Lys Ser Thr
        355                 360

<210> SEQ ID NO 13
<211> LENGTH: 1080
<212> TYPE: DNA
<213> ORGANISM: Nostoc sp
<220> FEATURE:
<221> NAME/KEY: CDS
<222> LOCATION: (1)..(1080)
<223> OTHER INFORMATION: transl_table=11

<400> SEQUENCE: 13 gtg caa tta gat acc atc agt ttc aac aat cct ctt aac agt gaa act      48
Val Gln Leu Asp Thr Ile Ser Phe Asn Asn Pro Leu Asn Ser Glu Thr
 1               5                  10                  15 tct gag gat aca act aaa tta cct ttc aca ctt ggg gat tta aaa gct      96
Ser Glu Asp Thr Thr Lys Leu Pro Phe Thr Leu Gly Asp Leu Lys Ala
             20                  25                  30 gca ata cct gct gaa tgc ttt cag ccc aat gtg aca aaa tca ctt ttt     144
Ala Ile Pro Ala Glu Cys Phe Gln Pro Asn Val Thr Lys Ser Leu Phe
```

-continued

```
                35                  40                  45
tac ttt ttt cgt gat atc ctg att atc ggt ctg ctt tat gca gtt gct      192
Tyr Phe Phe Arg Asp Ile Leu Ile Ile Gly Leu Leu Tyr Ala Val Ala
 50                  55                  60 tct tac ctg gat tct tgg ctt ttc ttt ccg att ttc tgg cta atg caa      240
Ser Tyr Leu Asp Ser Trp Leu Phe Phe Pro Ile Phe Trp Leu Met Gln
 65                  70                  75                  80 gga acg atg ttt tgg gct ttg ttt gta gtc ggg cat gac tgc gga cac      288
Gly Thr Met Phe Trp Ala Leu Phe Val Val Gly His Asp Cys Gly His
                 85                  90                  95 caa tct ttt tct aag cag aaa tgg ctc aat gat ttg att gga cat ctt      336
Gln Ser Phe Ser Lys Gln Lys Trp Leu Asn Asp Leu Ile Gly His Leu
            100                 105                 110 tct cac aca cca ata ctt gtt cct tat cat ggt tgg cgg att agt cac      384
Ser His Thr Pro Ile Leu Val Pro Tyr His Gly Trp Arg Ile Ser His
        115                 120                 125 aga act cac cac aaa aat act ggc aat att gat aac gat gaa agc tgg      432
Arg Thr His His Lys Asn Thr Gly Asn Ile Asp Asn Asp Glu Ser Trp
    130                 135                 140 tat cct gtg aca gaa tcc caa tat aaa gat atg cct tta gcc caa aag      480
Tyr Pro Val Thr Glu Ser Gln Tyr Lys Asp Met Pro Leu Ala Gln Lys
145                 150                 155                 160 ata ggc aga tat tat gtt ttt ctc ttg gct tat cct gta tat ctg ttt      528
Ile Gly Arg Tyr Tyr Val Phe Leu Leu Ala Tyr Pro Val Tyr Leu Phe
                165                 170                 175 aag cgt tct cct aat aaa gaa ggc tcc cac ttt tta ccc agt agt tca      576
Lys Arg Ser Pro Asn Lys Glu Gly Ser His Phe Leu Pro Ser Ser Ser
            180                 185                 190 ctt ttc aag cca tca gaa aaa tgg gat gtc ctc act agc act gta ctt      624
Leu Phe Lys Pro Ser Glu Lys Trp Asp Val Leu Thr Ser Thr Val Leu
        195                 200                 205 ttg att ggc atg gtt ggt ttg cta ggt ttc ctc acc tac caa tgg ggt      672
Leu Ile Gly Met Val Gly Leu Leu Gly Phe Leu Thr Tyr Gln Trp Gly
    210                 215                 220 tgg atg tgg ttg ctg aaa tat tat gca gtg ccc tac ctt gta ttc ata      720
Trp Met Trp Leu Leu Lys Tyr Tyr Ala Val Pro Tyr Leu Val Phe Ile
225                 230                 235                 240 gtt tgg cta gat ttg gtg aca ttc ttg cac cat act gag cca gaa ctt      768
Val Trp Leu Asp Leu Val Thr Phe Leu His His Thr Glu Pro Glu Leu
                245                 250                 255 cct tgg tat cgt gga gaa gat tgg act ttc ttg aaa ggt gca att tct      816
Pro Trp Tyr Arg Gly Glu Asp Trp Thr Phe Leu Lys Gly Ala Ile Ser
            260                 265                 270 agt att gac cgt gat tat ggt ttg gtt tat cat atc cat cac gat atc      864
Ser Ile Asp Arg Asp Tyr Gly Leu Val Tyr His Ile His His Asp Ile
        275                 280                 285 ggt act cat gtt gct cac cat ata ttc ctc aat atc cct cac tac aat      912
Gly Thr His Val Ala His His Ile Phe Leu Asn Ile Pro His Tyr Asn
    290                 295                 300 ttg ctg aag gca act gag gca ata aaa cca gtg atg ggc gag tat ttc      960
Leu Leu Lys Ala Thr Glu Ala Ile Lys Pro Val Met Gly Glu Tyr Phe
305                 310                 315                 320 cat aaa tcg gaa gaa cca att tgg aag tca tta tgg aat tca tgt atc     1008
His Lys Ser Glu Glu Pro Ile Trp Lys Ser Leu Trp Asn Ser Cys Ile
                325                 330                 335 agt tgc cat ttt gta cct gat act ggt agt aag gtt tac tac aca tct     1056
Ser Cys His Phe Val Pro Asp Thr Gly Ser Lys Val Tyr Tyr Thr Ser
            340                 345                 350 aag aac aag tca gct aaa gcc taa                                      1080
```

Lys Asn Lys Ser Ala Lys Ala
        355

<210> SEQ ID NO 14
<211> LENGTH: 359
<212> TYPE: PRT
<213> ORGANISM: Nostoc sp

<400> SEQUENCE: 14

Val Gln Leu Asp Thr Ile Ser Phe Asn Pro Leu Asn Ser Glu Thr
1               5                   10                  15

Ser Glu Asp Thr Thr Lys Leu Pro Phe Thr Leu Gly Asp Leu Lys Ala
                20                  25                  30

Ala Ile Pro Ala Glu Cys Phe Gln Pro Asn Val Thr Lys Ser Leu Phe
            35                  40                  45

Tyr Phe Phe Arg Asp Ile Leu Ile Ile Gly Leu Leu Tyr Ala Val Ala
        50                  55                  60

Ser Tyr Leu Asp Ser Trp Leu Phe Phe Pro Ile Phe Trp Leu Met Gln
65                  70                  75                  80

Gly Thr Met Phe Trp Ala Leu Phe Val Val Gly His Asp Cys Gly His
                85                  90                  95

Gln Ser Phe Ser Lys Gln Lys Trp Leu Asn Asp Leu Ile Gly His Leu
            100                 105                 110

Ser His Thr Pro Ile Leu Val Pro Tyr His Gly Trp Arg Ile Ser His
        115                 120                 125

Arg Thr His His Lys Asn Thr Gly Asn Ile Asp Asn Asp Glu Ser Trp
        130                 135                 140

Tyr Pro Val Thr Glu Ser Gln Tyr Lys Asp Met Pro Leu Ala Gln Lys
145                 150                 155                 160

Ile Gly Arg Tyr Tyr Val Phe Leu Leu Ala Tyr Pro Val Tyr Leu Phe
                165                 170                 175

Lys Arg Ser Pro Asn Lys Glu Gly Ser His Phe Leu Pro Ser Ser Ser
            180                 185                 190

Leu Phe Lys Pro Ser Glu Lys Trp Asp Val Leu Thr Ser Thr Val Leu
        195                 200                 205

Leu Ile Gly Met Val Gly Leu Leu Gly Phe Leu Thr Tyr Gln Trp Gly
        210                 215                 220

Trp Met Trp Leu Leu Lys Tyr Tyr Ala Val Pro Tyr Leu Val Phe Ile
225                 230                 235                 240

Val Trp Leu Asp Leu Val Thr Phe Leu His His Thr Glu Pro Glu Leu
                245                 250                 255

Pro Trp Tyr Arg Gly Glu Asp Trp Thr Phe Leu Lys Gly Ala Ile Ser
            260                 265                 270

Ser Ile Asp Arg Asp Tyr Gly Leu Val Tyr His Ile His His Asp Ile
        275                 280                 285

Gly Thr His Val Ala His His Ile Phe Leu Asn Ile Pro His Tyr Asn
        290                 295                 300

Leu Leu Lys Ala Thr Glu Ala Ile Lys Pro Val Met Gly Glu Tyr Phe
305                 310                 315                 320

His Lys Ser Glu Glu Pro Ile Trp Lys Ser Leu Trp Asn Ser Cys Ile
                325                 330                 335

Ser Cys His Phe Val Pro Asp Thr Gly Ser Lys Val Tyr Tyr Thr Ser
            340                 345                 350

Lys Asn Lys Ser Ala Lys Ala
        355

```
<210> SEQ ID NO 15
<211> LENGTH: 354
<212> TYPE: PRT
<213> ORGANISM: Artificial sequence
<220> FEATURE:
<223> OTHER INFORMATION: consensus sequence
<220> FEATURE:
<221> NAME/KEY: Variant
<222> LOCATION: (2)..(8)
<223> OTHER INFORMATION: Xaa in position 2 to 8 is any amino acid
<220> FEATURE:
<221> NAME/KEY: Variant
<222> LOCATION: (10)..(11)
<223> OTHER INFORMATION: Xaa in position 10 to 11 is any amino acid
<220> FEATURE:
<221> NAME/KEY: Variant
<222> LOCATION: (14)..(19)
<223> OTHER INFORMATION: Xaa in position 14 to 19 is any amino acid
<220> FEATURE:
<221> NAME/KEY: Variant
<222> LOCATION: (22)..(22)
<223> OTHER INFORMATION: Xaa in position 22 is any amino acid
<220> FEATURE:
<221> NAME/KEY: Variant
<222> LOCATION: (24)..(53)
<223> OTHER INFORMATION: Xaa in position 24 to 53 is any amino acid
<220> FEATURE:
<221> NAME/KEY: Variant
<222> LOCATION: (54)..(64)
<223> OTHER INFORMATION: Xaa in position 54 to 64 is any or no amino
    acid
<220> FEATURE:
<221> NAME/KEY: Variant
<222> LOCATION: (67)..(68)
<223> OTHER INFORMATION: Xaa in position 67 to 68 is any amino acid
<220> FEATURE:
<221> NAME/KEY: Variant
<222> LOCATION: (71)..(72)
<223> OTHER INFORMATION: Xaa in position 71 to 72 is any amino acid
<220> FEATURE:
<221> NAME/KEY: Variant
<222> LOCATION: (74)..(74)
<223> OTHER INFORMATION: Xaa in position 74 is any amino acid
<220> FEATURE:
<221> NAME/KEY: Variant
<222> LOCATION: (82)..(83)
<223> OTHER INFORMATION: Xaa in position 82 to 83 is any amino acid
<220> FEATURE:
<221> NAME/KEY: Variant
<222> LOCATION: (86)..(90)
<223> OTHER INFORMATION: Xaa in position 86 to 90 is any amino acid
<220> FEATURE:
<221> NAME/KEY: Variant
<222> LOCATION: (92)..(94)
<223> OTHER INFORMATION: Xaa in position 92 to 94 is any amino acid
<220> FEATURE:
<221> NAME/KEY: Variant
<222> LOCATION: (96)..(98)
<223> OTHER INFORMATION: Xaa in position 96 to 98 is any amino acid
<220> FEATURE:
<221> NAME/KEY: Variant
<222> LOCATION: (100)..(101)
<223> OTHER INFORMATION: Xaa in position 100 to 101 is any amino acid
<220> FEATURE:
<221> NAME/KEY: Variant
<222> LOCATION: (104)..(104)
<223> OTHER INFORMATION: Xaa in position 104 is any amino acid
<220> FEATURE:
<221> NAME/KEY: Variant
<222> LOCATION: (106)..(108)
<223> OTHER INFORMATION: Xaa in position 106 to 108 is any amino acid
<220> FEATURE:
<221> NAME/KEY: Variant
<222> LOCATION: (110)..(112)
<223> OTHER INFORMATION: Xaa in position 110 to 112 is any amino acid
<220> FEATURE:
<221> NAME/KEY: Variant
```

```
<222> LOCATION: (115)..(115)
<223> OTHER INFORMATION: Xaa in position 115 is any amino acid
<220> FEATURE:
<221> NAME/KEY: Variant
<222> LOCATION: (118)..(118)
<223> OTHER INFORMATION: Xaa in position 118 is any amino acid
<220> FEATURE:
<221> NAME/KEY: Variant
<222> LOCATION: (125)..(125)
<223> OTHER INFORMATION: Xaa in position 125 is any amino acid
<220> FEATURE:
<221> NAME/KEY: Variant
<222> LOCATION: (128)..(129)
<223> OTHER INFORMATION: Xaa in position 128 to 129 is any amino acid
<220> FEATURE:
<221> NAME/KEY: Variant
<222> LOCATION: (132)..(150)
<223> OTHER INFORMATION: Xaa in position 132 to 150 is any amino acid
<220> FEATURE:
<221> NAME/KEY: Variant
<222> LOCATION: (151)..(154)
<223> OTHER INFORMATION: Xaa in position 151 to 154 is any or no amino
      acid
<220> FEATURE:
<221> NAME/KEY: Variant
<222> LOCATION: (156)..(158)
<223> OTHER INFORMATION: Xaa in position 156 to 158 is any amino acid
<220> FEATURE:
<221> NAME/KEY: Variant
<222> LOCATION: (161)..(170)
<223> OTHER INFORMATION: Xaa in position 161 to 170 is any amino acid
<220> FEATURE:
<221> NAME/KEY: Variant
<222> LOCATION: (171)..(171)
<223> OTHER INFORMATION: Xaa in position 171 is any or no amino acid
<220> FEATURE:
<221> NAME/KEY: Variant
<222> LOCATION: (174)..(174)
<223> OTHER INFORMATION: Xaa in position 174 is any amino acid
<220> FEATURE:
<221> NAME/KEY: Variant
<222> LOCATION: (176)..(178)
<223> OTHER INFORMATION: Xaa in position 176 to 178 is any amino acid
<220> FEATURE:
<221> NAME/KEY: Variant
<222> LOCATION: (180)..(186)
<223> OTHER INFORMATION: Xaa in position 180 to 186 is any amino acid
<220> FEATURE:
<221> NAME/KEY: Variant
<222> LOCATION: (187)..(187)
<223> OTHER INFORMATION: Xaa in position 187 is any or no amino acid
<220> FEATURE:
<221> NAME/KEY: Variant
<222> LOCATION: (189)..(190)
<223> OTHER INFORMATION: Xaa in position 189 to 190 is any amino acid
<220> FEATURE:
<221> NAME/KEY: Variant
<222> LOCATION: (192)..(204)
<223> OTHER INFORMATION: Xaa in position 192 to 204 is any amino acid
<220> FEATURE:
<221> NAME/KEY: Variant
<222> LOCATION: (207)..(209)
<223> OTHER INFORMATION: Xaa in position 207 to 209 is any amino acid
<220> FEATURE:
<221> NAME/KEY: Variant
<222> LOCATION: (211)..(217)
<223> OTHER INFORMATION: Xaa in position 211 to 217 is any amino acid
<220> FEATURE:
<221> NAME/KEY: Variant
<222> LOCATION: (219)..(220)
<223> OTHER INFORMATION: Xaa in position 219 to 220 is any amino acid
<220> FEATURE:
<221> NAME/KEY: Variant
<222> LOCATION: (222)..(224)
<223> OTHER INFORMATION: Xaa in position 222 to 224 is any amino acid
<220> FEATURE:
<221> NAME/KEY: Variant
<222> LOCATION: (226)..(228)
<223> OTHER INFORMATION: Xaa in position 226 to 228 is any amino acid
```

```
<220> FEATURE:
<221> NAME/KEY: Variant
<222> LOCATION: (230)..(232)
<223> OTHER INFORMATION: Xaa in position 230 to 232 is any amino acid
<220> FEATURE:
<221> NAME/KEY: Variant
<222> LOCATION: (238)..(242)
<223> OTHER INFORMATION: Xaa in position 238 to 242 is any amino acid
<220> FEATURE:
<221> NAME/KEY: Variant
<222> LOCATION: (246)..(249)
<223> OTHER INFORMATION: Xaa in position 246 to 249 is any amino acid
<220> FEATURE:
<221> NAME/KEY: Variant
<222> LOCATION: (251)..(253)
<223> OTHER INFORMATION: Xaa in position 251 to 253 is any amino acid
<220> FEATURE:
<221> NAME/KEY: Variant
<222> LOCATION: (256)..(257)
<223> OTHER INFORMATION: Xaa in position 256 to 257 is any amino acid
<220> FEATURE:
<221> NAME/KEY: Variant
<222> LOCATION: (259)..(260)
<223> OTHER INFORMATION: Xaa in position 259 to 260 is any amino acid
<220> FEATURE:
<221> NAME/KEY: Variant
<222> LOCATION: (263)..(263)
<223> OTHER INFORMATION: Xaa in position 263 is any amino acid
<220> FEATURE:
<221> NAME/KEY: Variant
<222> LOCATION: (266)..(271)
<223> OTHER INFORMATION: Xaa in position 266 to 271 is any amino acid
<220> FEATURE:
<221> NAME/KEY: Variant
<222> LOCATION: (272)..(272)
<223> OTHER INFORMATION: Xaa in position 272 is any or no amino acid
<220> FEATURE:
<221> NAME/KEY: Variant
<222> LOCATION: (274)..(274)
<223> OTHER INFORMATION: Xaa in position 274 is any amino acid
<220> FEATURE:
<221> NAME/KEY: Variant
<222> LOCATION: (279)..(280)
<223> OTHER INFORMATION: Xaa in position 279 to 280 is any amino acid
<220> FEATURE:
<221> NAME/KEY: Variant
<222> LOCATION: (283)..(283)
<223> OTHER INFORMATION: Xaa in position 283 is any amino acid
<220> FEATURE:
<221> NAME/KEY: Variant
<222> LOCATION: (285)..(287)
<223> OTHER INFORMATION: Xaa in position 285 to 287 is any amino acid
<220> FEATURE:
<221> NAME/KEY: Variant
<222> LOCATION: (291)..(291)
<223> OTHER INFORMATION: Xaa in position 291 is any amino acid
<220> FEATURE:
<221> NAME/KEY: Variant
<222> LOCATION: (293)..(294)
<223> OTHER INFORMATION: Xaa in position 293 to 294 is any amino acid
<220> FEATURE:
<221> NAME/KEY: Variant
<222> LOCATION: (297)..(312)
<223> OTHER INFORMATION: Xaa in position 297 to 312 is any amino acid
<220> FEATURE:
<221> NAME/KEY: Variant
<222> LOCATION: (315)..(340)
<223> OTHER INFORMATION: Xaa in position 315 to 340 is any amino acid
<220> FEATURE:
<221> NAME/KEY: Variant
<222> LOCATION: (341)..(353)
<223> OTHER INFORMATION: Xaa in position 341 to 353 is any or no amino
      acid

<400> SEQUENCE: 15

Leu Xaa Xaa Xaa Xaa Xaa Xaa Xaa Pro Xaa Xaa Cys Phe Xaa Xaa Xaa
1               5                   10                  15
```

Xaa Xaa Xaa Ser Leu Xaa Tyr Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa
    50                  55                  60

Gln Gly Xaa Xaa Phe Trp Xaa Xaa Phe Xaa Val Gly His Asp Cys Gly
65                  70                  75                  80

His Xaa Xaa Phe Ser Xaa Xaa Xaa Xaa Asn Xaa Xaa Xaa Gly Xaa
                85                  90                  95

Xaa Xaa His Xaa Xaa Ile Leu Xaa Pro Xaa Xaa Xaa Trp Xaa Xaa
            100                 105                 110

His Arg Xaa His His Xaa Asn Thr Gly Asn Ile Asp Xaa Asp Glu Xaa
            115                 120                 125

Xaa Tyr Pro Xaa Xaa Xaa Xaa Xaa Xaa Xaa Xaa Xaa Xaa Xaa
        130                 135                 140

Xaa Xaa Xaa Xaa Xaa Xaa Xaa Xaa Ala Xaa Xaa Xaa Tyr Leu
145                 150                 155                 160

Xaa Xaa Xaa Xaa Xaa Xaa Xaa Xaa Xaa Xaa His Phe Xaa Pro Xaa
                165                 170                 175

Xaa Xaa Leu Xaa Xaa Xaa Xaa Xaa Xaa Xaa Val Xaa Xaa Ser Xaa
            180                 185                 190

Xaa Xaa Xaa Xaa Xaa Xaa Xaa Xaa Xaa Xaa Leu Thr Xaa Xaa
        195                 200                 205

Xaa Gly Xaa Xaa Xaa Xaa Xaa Xaa Tyr Xaa Xaa Pro Xaa Xaa Xaa
    210                 215                 220

Phe Xaa Xaa Xaa Leu Xaa Xaa Xaa Thr Phe Leu His His Xaa Xaa
225                 230                 235                 240

Xaa Xaa Pro Trp Tyr Xaa Xaa Xaa Xaa Trp Xaa Xaa Xaa Lys Gly Xaa
                245                 250                 255

Xaa Ser Xaa Xaa Asp Arg Xaa Tyr Gly Xaa Xaa Xaa Xaa Xaa Xaa
            260                 265                 270

His Xaa Ile Gly Thr His Xaa Xaa His His Xaa Phe Xaa Xaa Xaa Pro
            275                 280                 285

His Tyr Xaa Leu Xaa Xaa Ala Thr Xaa Xaa Xaa Xaa Xaa Xaa Xaa
        290                 295                 300

Xaa Xaa Xaa Xaa Xaa Xaa Xaa Xaa Pro Ile Xaa Xaa Xaa Xaa Xaa
305                 310                 315                 320

Xaa Xaa Xaa Xaa Xaa Xaa Xaa Xaa Xaa Xaa Xaa Xaa Xaa Xaa
        325                 330                 335

Xaa Xaa Xaa Xaa Xaa Xaa Xaa Xaa Xaa Xaa Xaa Xaa Xaa Xaa Xaa
        340                 345                 350

Xaa Lys

<210> SEQ ID NO 16
<211> LENGTH: 60
<212> TYPE: PRT
<213> ORGANISM: Artificial sequence
<220> FEATURE:
<223> OTHER INFORMATION: sequence motif
<220> FEATURE:
<221> NAME/KEY: Variant
<222> LOCATION: (2)..(2)
<223> OTHER INFORMATION: Xaa in position 2 is any or no amino acid
<220> FEATURE:
<221> NAME/KEY: Variant
<222> LOCATION: (4)..(4)

```
<223> OTHER INFORMATION: Xaa in position 4 is any or no amino acid
<220> FEATURE:
<221> NAME/KEY: Variant
<222> LOCATION: (11)..(11)
<223> OTHER INFORMATION: Xaa in position 11 is Gly, Gln or Ser
<220> FEATURE:
<221> NAME/KEY: Variant
<222> LOCATION: (12)..(12)
<223> OTHER INFORMATION: Xaa in position 12 is Ala or Ser
<220> FEATURE:
<221> NAME/KEY: Variant
<222> LOCATION: (15)..(15)
<223> OTHER INFORMATION: Xaa in position 15 is Lys or Arg
<220> FEATURE:
<221> NAME/KEY: Variant
<222> LOCATION: (16)..(16)
<223> OTHER INFORMATION: Xaa in position 16 is any amino acid
<220> FEATURE:
<221> NAME/KEY: Variant
<222> LOCATION: (17)..(17)
<223> OTHER INFORMATION: Xaa in position 17 is His or Lys
<220> FEATURE:
<221> NAME/KEY: Variant
<222> LOCATION: (18)..(18)
<223> OTHER INFORMATION: Xaa in position 18 is any amino acid
<220> FEATURE:
<221> NAME/KEY: Variant
<222> LOCATION: (19)..(19)
<223> OTHER INFORMATION: Xaa in position 19 is Leu or Val
<220> FEATURE:
<221> NAME/KEY: Variant
<222> LOCATION: (21)..(22)
<223> OTHER INFORMATION: Xaa in position 21 to 22 is any amino acid
<220> FEATURE:
<221> NAME/KEY: Variant
<222> LOCATION: (23)..(23)
<223> OTHER INFORMATION: Xaa in position 23 is Ile or Val
<220> FEATURE:
<221> NAME/KEY: Variant
<222> LOCATION: (25)..(25)
<223> OTHER INFORMATION: Xaa in position 25 is any amino acid
<220> FEATURE:
<221> NAME/KEY: Variant
<222> LOCATION: (26)..(26)
<223> OTHER INFORMATION: Xaa in position 26 is Ile or Leu
<220> FEATURE:
<221> NAME/KEY: Variant
<222> LOCATION: (27)..(27)
<223> OTHER INFORMATION: Xaa in position 27 is any amino acid
<220> FEATURE:
<221> NAME/KEY: Variant
<222> LOCATION: (29)..(29)
<223> OTHER INFORMATION: Xaa in position 29 is Ser or Thr
<220> FEATURE:
<221> NAME/KEY: Variant
<222> LOCATION: (30)..(30)
<223> OTHER INFORMATION: Xaa in position 30 is Ala, Ile or Pro
<220> FEATURE:
<221> NAME/KEY: Variant
<222> LOCATION: (33)..(33)
<223> OTHER INFORMATION: Xaa in position 33 is Thr or Val
<220> FEATURE:
<221> NAME/KEY: Variant
<222> LOCATION: (35)..(35)
<223> OTHER INFORMATION: Xaa in position 35 is Phe or Tyr
<220> FEATURE:
<221> NAME/KEY: Variant
<222> LOCATION: (36)..(36)
<223> OTHER INFORMATION: Xaa in position 36 is Glu or His
<220> FEATURE:
<221> NAME/KEY: Variant
<222> LOCATION: (37)..(37)
<223> OTHER INFORMATION: Xaa in position 37 is Gly or Ser
<220> FEATURE:
<221> NAME/KEY: Variant
<222> LOCATION: (39)..(39)
<223> OTHER INFORMATION: Xaa in position 39 is Lys or Arg
<220> FEATURE:
<221> NAME/KEY: Variant
```

```
<222> LOCATION: (40)..(40)
<223> OTHER INFORMATION: Xaa in position 40 is Ile, Leu or Val
<220> FEATURE:
<221> NAME/KEY: Variant
<222> LOCATION: (41)..(41)
<223> OTHER INFORMATION: Xaa in position 41 is Ser or Thr
<220> FEATURE:
<221> NAME/KEY: Variant
<222> LOCATION: (44)..(44)
<223> OTHER INFORMATION: Xaa in position 44 is any amino acid
<220> FEATURE:
<221> NAME/KEY: Variant
<222> LOCATION: (47)..(47)
<223> OTHER INFORMATION: Xaa in position 47 is any amino acid
<220> FEATURE:
<221> NAME/KEY: Variant
<222> LOCATION: (54)..(54)
<223> OTHER INFORMATION: Xaa in position 54 is any amino acid
<220> FEATURE:
<221> NAME/KEY: Variant
<222> LOCATION: (57)..(57)
<223> OTHER INFORMATION: Xaa in position 57 is any amino acid
<220> FEATURE:
<221> NAME/KEY: Variant
<222> LOCATION: (58)..(58)
<223> OTHER INFORMATION: Xaa in position 58 is Phe or Trp

<400> SEQUENCE: 16

Phe Xaa Val Xaa Gly His Asp Cys Gly His Xaa Xaa Phe Ser Xaa Xaa
1               5                   10                  15

Xaa Xaa Xaa Asn Xaa Xaa Xaa Gly Xaa Xaa Xaa His Xaa Xaa Ile Leu
            20                  25                  30

Xaa Pro Xaa Xaa Xaa Trp Xaa Xaa Xaa His Arg Xaa His His Xaa Asn
        35                  40                  45

Thr Gly Asn Ile Asp Xaa Asp Glu Xaa Xaa Tyr Pro
    50                  55                  60

<210> SEQ ID NO 17
<211> LENGTH: 38
<212> TYPE: PRT
<213> ORGANISM: Artificial sequence
<220> FEATURE:
<223> OTHER INFORMATION: sequence motif
<220> FEATURE:
<221> NAME/KEY: Variant
<222> LOCATION: (2)..(2)
<223> OTHER INFORMATION: Xaa in position 2 is any or no amino acid
<220> FEATURE:
<221> NAME/KEY: Variant
<222> LOCATION: (4)..(4)
<223> OTHER INFORMATION: Xaa in position 4 is any or no amino acid
<220> FEATURE:
<221> NAME/KEY: Variant
<222> LOCATION: (6)..(6)
<223> OTHER INFORMATION: Xaa in position 6 is any or no amino acid
<220> FEATURE:
<221> NAME/KEY: Variant
<222> LOCATION: (11)..(11)
<223> OTHER INFORMATION: Xaa in position 11 is Asn or Thr
<220> FEATURE:
<221> NAME/KEY: Variant
<222> LOCATION: (12)..(12)
<223> OTHER INFORMATION: Xaa in position 12 is Asp or Glu
<220> FEATURE:
<221> NAME/KEY: Variant
<222> LOCATION: (13)..(13)
<223> OTHER INFORMATION: Xaa in position 13 is Asp, Glu or Pro
<220> FEATURE:
<221> NAME/KEY: Variant
<222> LOCATION: (14)..(14)
<223> OTHER INFORMATION: Xaa in position 14 is Ala, Glu or Asn
<220> FEATURE:
<221> NAME/KEY: Variant
<222> LOCATION: (15)..(15)
```

```
<223> OTHER INFORMATION: Xaa in position 15 is any amino acid
<220> FEATURE:
<221> NAME/KEY: Variant
<222> LOCATION: (19)..(19)
<223> OTHER INFORMATION: Xaa in position 19 is any amino acid
<220> FEATURE:
<221> NAME/KEY: Variant
<222> LOCATION: (20)..(20)
<223> OTHER INFORMATION: Xaa in position 20 is Asp or Gly
<220> FEATURE:
<221> NAME/KEY: Variant
<222> LOCATION: (21)..(21)
<223> OTHER INFORMATION: Xaa in position 21 is Asp, Glu or Ser
<220> FEATURE:
<221> NAME/KEY: Variant
<222> LOCATION: (22)..(22)
<223> OTHER INFORMATION: Xaa in position 22 is Asp or Glu
<220> FEATURE:
<221> NAME/KEY: Variant
<222> LOCATION: (24)..(24)
<223> OTHER INFORMATION: Xaa in position 24 is any amino acid
<220> FEATURE:
<221> NAME/KEY: Variant
<222> LOCATION: (25)..(25)
<223> OTHER INFORMATION: Xaa in position 25 is Phe or Tyr
<220> FEATURE:
<221> NAME/KEY: Variant
<222> LOCATION: (26)..(26)
<223> OTHER INFORMATION: Xaa in position 26 is Leu or Val
<220> FEATURE:
<221> NAME/KEY: Variant
<222> LOCATION: (29)..(29)
<223> OTHER INFORMATION: Xaa in position 29 is Ala or Asn
<220> FEATURE:
<221> NAME/KEY: Variant
<222> LOCATION: (30)..(30)
<223> OTHER INFORMATION: Xaa in position 30 is Ile or Leu
<220> FEATURE:
<221> NAME/KEY: Variant
<222> LOCATION: (32)..(32)
<223> OTHER INFORMATION: Xaa in position 32 is Ser or Thr
<220> FEATURE:
<221> NAME/KEY: Variant
<222> LOCATION: (33)..(33)
<223> OTHER INFORMATION: Xaa in position 33 is Ile or Val
<220> FEATURE:
<221> NAME/KEY: Variant
<222> LOCATION: (36)..(36)
<223> OTHER INFORMATION: Xaa in position 36 is Asp or Ser

<400> SEQUENCE: 17

Leu Xaa Val Xaa Thr Xaa Phe Leu His His Xaa Xaa Xaa Xaa Xaa Pro
1               5                   10                  15

Trp Tyr Xaa Xaa Xaa Xaa Trp Xaa Xaa Xaa Lys Gly Xaa Xaa Ser Xaa
            20                  25                  30

Xaa Asp Arg Xaa Tyr Gly
        35

<210> SEQ ID NO 18
<211> LENGTH: 28
<212> TYPE: PRT
<213> ORGANISM: Artificial sequence
<220> FEATURE:
<223> OTHER INFORMATION: sequence motif
<220> FEATURE:
<221> NAME/KEY: Variant
<222> LOCATION: (2)..(6)
<223> OTHER INFORMATION: Xaa in position 2 to 6 is any or no amino acid
<220> FEATURE:
<221> NAME/KEY: Variant
<222> LOCATION: (11)..(11)
<223> OTHER INFORMATION: Xaa in position 11 is any amino acid
<220> FEATURE:
<221> NAME/KEY: Variant
<222> LOCATION: (12)..(12)
```

```
<223> OTHER INFORMATION: Xaa in position 12 is Ala, Ile or Val
<220> FEATURE:
<221> NAME/KEY: Variant
<222> LOCATION: (15)..(15)
<223> OTHER INFORMATION: Xaa in position 15 is Ile or Leu
<220> FEATURE:
<221> NAME/KEY: Variant
<222> LOCATION: (17)..(18)
<223> OTHER INFORMATION: Xaa in position 17 to 18 is any amino acid
<220> FEATURE:
<221> NAME/KEY: Variant
<222> LOCATION: (19)..(19)
<223> OTHER INFORMATION: Xaa in position 19 is Ile or Met
<220> FEATURE:
<221> NAME/KEY: Variant
<222> LOCATION: (23)..(23)
<223> OTHER INFORMATION: Xaa in position 23 is any amino acid
<220> FEATURE:
<221> NAME/KEY: Variant
<222> LOCATION: (25)..(25)
<223> OTHER INFORMATION: Xaa in position 25 is any amino acid
<220> FEATURE:
<221> NAME/KEY: Variant
<222> LOCATION: (26)..(26)
<223> OTHER INFORMATION: Xaa in position 26 is Asp, Glu, Lys or Arg

<400> SEQUENCE: 18

Asp Xaa Xaa Xaa Xaa Xaa Ile Gly Thr His Xaa Xaa His His Xaa Phe
1               5                   10                  15

Xaa Xaa Xaa Pro His Tyr Xaa Leu Xaa Xaa Ala Thr
            20                  25

<210> SEQ ID NO 19
<211> LENGTH: 32
<212> TYPE: PRT
<213> ORGANISM: Artificial sequence
<220> FEATURE:
<223> OTHER INFORMATION: sequence motif
<220> FEATURE:
<221> NAME/KEY: Variant
<222> LOCATION: (2)..(3)
<223> OTHER INFORMATION: Xaa in position 2 to 3 is any amino acid
<220> FEATURE:
<221> NAME/KEY: Variant
<222> LOCATION: (4)..(4)
<223> OTHER INFORMATION: Xaa in position 4 is any or no amino acid
<220> FEATURE:
<221> NAME/KEY: Variant
<222> LOCATION: (6)..(9)
<223> OTHER INFORMATION: Xaa in position 6 to 9 is any or no amino acid
<220> FEATURE:
<221> NAME/KEY: Variant
<222> LOCATION: (11)..(11)
<223> OTHER INFORMATION: Xaa in position 11 is any amino acid
<220> FEATURE:
<221> NAME/KEY: Variant
<222> LOCATION: (12)..(12)
<223> OTHER INFORMATION: Xaa in position 12 is Ala, Asp or Glu
<220> FEATURE:
<221> NAME/KEY: Variant
<222> LOCATION: (15)..(15)
<223> OTHER INFORMATION: Xaa in position 15 is Glu or Gln
<220> FEATURE:
<221> NAME/KEY: Variant
<222> LOCATION: (16)..(16)
<223> OTHER INFORMATION: Xaa in position 16 is Ala, Pro or Ser
<220> FEATURE:
<221> NAME/KEY: Variant
<222> LOCATION: (17)..(17)
<223> OTHER INFORMATION: Xaa in position 17 is Asn or Ser
<220> FEATURE:
<221> NAME/KEY: Variant
<222> LOCATION: (18)..(18)
<223> OTHER INFORMATION: Xaa in position 18 is Leu or Val
<220> FEATURE:
<221> NAME/KEY: Variant
```

```
<222> LOCATION: (19)..(20)
<223> OTHER INFORMATION: Xaa in position 19 to 20 is any amino acid
<220> FEATURE:
<221> NAME/KEY: Variant
<222> LOCATION: (23)..(23)
<223> OTHER INFORMATION: Xaa in position 23 is any amino acid
<220> FEATURE:
<221> NAME/KEY: Variant
<222> LOCATION: (25)..(27)
<223> OTHER INFORMATION: Xaa in position 25 to 27 is any amino acid
<220> FEATURE:
<221> NAME/KEY: Variant
<222> LOCATION: (28)..(28)
<223> OTHER INFORMATION: Xaa in position 28 is Ala, Cys, Asp or Ser
<220> FEATURE:
<221> NAME/KEY: Variant
<222> LOCATION: (29)..(29)
<223> OTHER INFORMATION: Xaa in position 29 is Ile, Leu or Val
<220> FEATURE:
<221> NAME/KEY: Variant
<222> LOCATION: (30)..(31)
<223> OTHER INFORMATION: Xaa in position 30 to 31 is any amino acid
<220> FEATURE:
<221> NAME/KEY: Variant
<222> LOCATION: (32)..(32)
<223> OTHER INFORMATION: Xaa in position 32 is Ala or Ile

<400> SEQUENCE: 19

Leu Xaa Xaa Xaa Ile Xaa Xaa Xaa Xaa Pro Xaa Xaa Cys Phe Xaa Xaa
1               5                   10                  15

Xaa Xaa Xaa Xaa Ser Leu Xaa Tyr Xaa Xaa Xaa Xaa Xaa Xaa Xaa Xaa
            20                  25                  30

<210> SEQ ID NO 20
<211> LENGTH: 13
<212> TYPE: PRT
<213> ORGANISM: Artificial sequence
<220> FEATURE:
<223> OTHER INFORMATION: sequence motif
<220> FEATURE:
<221> NAME/KEY: Variant
<222> LOCATION: (2)..(3)
<223> OTHER INFORMATION: Xaa in position 2 to 3 is any amino acid
<220> FEATURE:
<221> NAME/KEY: Variant
<222> LOCATION: (4)..(5)
<223> OTHER INFORMATION: Xaa in position 4 to 5 is any or no amino acid
<220> FEATURE:
<221> NAME/KEY: Variant
<222> LOCATION: (8)..(8)
<223> OTHER INFORMATION: Xaa in position 8 is any amino acid
<220> FEATURE:
<221> NAME/KEY: Variant
<222> LOCATION: (9)..(9)
<223> OTHER INFORMATION: Xaa in position 9 is Ile, Leu, Met or Val
<220> FEATURE:
<221> NAME/KEY: Variant
<222> LOCATION: (12)..(12)
<223> OTHER INFORMATION: Xaa in position 12 is Ala, Gly or Ser
<220> FEATURE:
<221> NAME/KEY: Variant
<222> LOCATION: (13)..(13)
<223> OTHER INFORMATION: Xaa in position 13 is Phe or Leu

<400> SEQUENCE: 20

Ile Xaa Xaa Xaa Xaa Gln Gly Xaa Xaa Phe Trp Xaa Xaa
1               5                   10

<210> SEQ ID NO 21
<211> LENGTH: 17
<212> TYPE: PRT
<213> ORGANISM: Artificial sequence
<220> FEATURE:
<223> OTHER INFORMATION: sequence motif
```

```
<220> FEATURE:
<221> NAME/KEY: Variant
<222> LOCATION: (2)..(2)
<223> OTHER INFORMATION: Xaa in position 2 is any amino acid
<220> FEATURE:
<221> NAME/KEY: Variant
<222> LOCATION: (3)..(4)
<223> OTHER INFORMATION: Xaa in position 3 to 4 is any or no amino acid
<220> FEATURE:
<221> NAME/KEY: Variant
<222> LOCATION: (6)..(6)
<223> OTHER INFORMATION: Xaa in position 6 is Trp or Tyr
<220> FEATURE:
<221> NAME/KEY: Variant
<222> LOCATION: (7)..(7)
<223> OTHER INFORMATION: Xaa in position 7 is any amino acid
<220> FEATURE:
<221> NAME/KEY: Variant
<222> LOCATION: (8)..(8)
<223> OTHER INFORMATION: Xaa in position 8 is Ala, Ile or Val
<220> FEATURE:
<221> NAME/KEY: Variant
<222> LOCATION: (11)..(14)
<223> OTHER INFORMATION: Xaa in position 11 to 14 is any amino acid
<220> FEATURE:
<221> NAME/KEY: Variant
<222> LOCATION: (15)..(15)
<223> OTHER INFORMATION: Xaa in position 15 is any or no amino acid
<220> FEATURE:
<221> NAME/KEY: Variant
<222> LOCATION: (17)..(17)
<223> OTHER INFORMATION: Xaa in position 17 is Asn or Arg

<400> SEQUENCE: 21

Leu Xaa Xaa Xaa Ala Xaa Xaa Xaa Tyr Leu Xaa Xaa Xaa Xaa Xaa Pro
1               5                   10                  15

Xaa

<210> SEQ ID NO 22
<211> LENGTH: 15
<212> TYPE: PRT
<213> ORGANISM: Artificial sequence
<220> FEATURE:
<223> OTHER INFORMATION: sequence motif
<220> FEATURE:
<221> NAME/KEY: Variant
<222> LOCATION: (2)..(4)
<223> OTHER INFORMATION: Xaa in position 2 to 4 is any amino acid
<220> FEATURE:
<221> NAME/KEY: Variant
<222> LOCATION: (5)..(5)
<223> OTHER INFORMATION: Xaa in position 5 is Phe, Leu or Met
<220> FEATURE:
<221> NAME/KEY: Variant
<222> LOCATION: (6)..(6)
<223> OTHER INFORMATION: Xaa in position 6 is Ala, Gly, Leu or Val
<220> FEATURE:
<221> NAME/KEY: Variant
<222> LOCATION: (7)..(7)
<223> OTHER INFORMATION: Xaa in position 7 is any amino acid
<220> FEATURE:
<221> NAME/KEY: Variant
<222> LOCATION: (8)..(8)
<223> OTHER INFORMATION: Xaa in position 8 is Phe or Tyr
<220> FEATURE:
<221> NAME/KEY: Variant
<222> LOCATION: (10)..(10)
<223> OTHER INFORMATION: Xaa in position 10 is any amino acid
<220> FEATURE:
<221> NAME/KEY: Variant
<222> LOCATION: (11)..(11)
<223> OTHER INFORMATION: Xaa in position 11 is Ala, Gly or Val
<220> FEATURE:
<221> NAME/KEY: Variant
<222> LOCATION: (13)..(13)
<223> OTHER INFORMATION: Xaa in position 13 is any amino acid
```

```
<220> FEATURE:
<221> NAME/KEY: Variant
<222> LOCATION: (14)..(14)
<223> OTHER INFORMATION: Xaa in position 14 is any or no amino acid

<400> SEQUENCE: 22

Gly Xaa Xaa Xaa Xaa Xaa Xaa Tyr Xaa Xaa Pro Xaa Xaa Val
1               5                   10                  15

<210> SEQ ID NO 23
<211> LENGTH: 1092
<212> TYPE: DNA
<213> ORGANISM: Pythium irregulare
<220> FEATURE:
<221> NAME/KEY: CDS
<222> LOCATION: (1)..(1092)

<400> SEQUENCE: 23 atg gcg tcc acc tcc gcc gcc caa gac gcc gcg ccg tac gag ttc ccg        48
Met Ala Ser Thr Ser Ala Ala Gln Asp Ala Ala Pro Tyr Glu Phe Pro
1               5                   10                  15 tcg ctg acc gag atc aag cgc gcg ctg ccc agc gag tgc ttc gaa gcg        96
Ser Leu Thr Glu Ile Lys Arg Ala Leu Pro Ser Glu Cys Phe Glu Ala
                20                  25                  30 tcg gtg ccc ctg tcg ctc tac tac acc gcg cgc tcg ctg gcg ctt gcc       144
Ser Val Pro Leu Ser Leu Tyr Tyr Thr Ala Arg Ser Leu Ala Leu Ala
            35                  40                  45 ggc tcg ctc gcg gtc gcg ctc tcg tac gcg cgt gcg ctg ccg ctg gtg       192
Gly Ser Leu Ala Val Ala Leu Ser Tyr Ala Arg Ala Leu Pro Leu Val
        50                  55                  60 cag gcg aac gcg ctg ctc gac gcc acg ctc tgt acg ggc tac gtg cta       240
Gln Ala Asn Ala Leu Leu Asp Ala Thr Leu Cys Thr Gly Tyr Val Leu
65                  70                  75                  80 ctg cag ggc atc gtg ttc tgg ggc ttc ttc aca gtc ggc cac gac tgc       288
Leu Gln Gly Ile Val Phe Trp Gly Phe Phe Thr Val Gly His Asp Cys
                85                  90                  95 ggc cac ggc gcg ttc tcg cgc tcg cat gtg ctc aac ttc agc gtc ggc       336
Gly His Gly Ala Phe Ser Arg Ser His Val Leu Asn Phe Ser Val Gly
            100                 105                 110 acg ctc atg cac tcg atc atc ctc acg ccg ttc gag tcc tgg aag ctg       384
Thr Leu Met His Ser Ile Ile Leu Thr Pro Phe Glu Ser Trp Lys Leu
        115                 120                 125 tcg cac cgc cac cac cac aag aac acg ggc aac atc gac aag gac gag       432
Ser His Arg His His His Lys Asn Thr Gly Asn Ile Asp Lys Asp Glu
    130                 135                 140 atc ttc tac ccg cag cgc gag gct gac tcg cac cca gtc tcc cgc cac       480
Ile Phe Tyr Pro Gln Arg Glu Ala Asp Ser His Pro Val Ser Arg His
145                 150                 155                 160 ttg gtc atg tcg ctc ggc tcg gcg tgg ttt gcc tac ctg ttc gcg ggc       528
Leu Val Met Ser Leu Gly Ser Ala Trp Phe Ala Tyr Leu Phe Ala Gly
                165                 170                 175 ttc cct cct cgc acg atg aac cac ttc aac ccg tgg gaa gcg atg tac       576
Phe Pro Pro Arg Thr Met Asn His Phe Asn Pro Trp Glu Ala Met Tyr
            180                 185                 190 gtg cgt cgt gtg gcc gct gtg atc atc tcg ctc ggc gtg ctc ttc gcc       624
Val Arg Arg Val Ala Ala Val Ile Ile Ser Leu Gly Val Leu Phe Ala
        195                 200                 205 ttc gca ggt ctc tac tcg tac ctg acc ttc gtc ttg ggc ttc acg acc       672
Phe Ala Gly Leu Tyr Ser Tyr Leu Thr Phe Val Leu Gly Phe Thr Thr
    210                 215                 220 atg gcg atc tac tac ttt ggt cca ttg ttc gtc ttc gcc acg atg ctc       720
Met Ala Ile Tyr Tyr Phe Gly Pro Leu Phe Val Phe Ala Thr Met Leu
```

-continued

```
                225                 230                 235                 240
gtg gtc acc acg ttc ttg cac cac aac gac gaa gag acc ccg tgg tac      768
Val Val Thr Thr Phe Leu His His Asn Asp Glu Glu Thr Pro Trp Tyr
                    245                 250                 255 gcg gac tcg gag tgg acg tac gtc aag ggc aac ctc tcg tcc gtg gac      816
Ala Asp Ser Glu Trp Thr Tyr Val Lys Gly Asn Leu Ser Ser Val Asp
                    260                 265                 270 cgc tca tac ggc gcg ctg att gac aac ctg agc cac aac atc ggc acg      864
Arg Ser Tyr Gly Ala Leu Ile Asp Asn Leu Ser His Asn Ile Gly Thr
                    275                 280                 285 cac cag atc cac cac ctg ttc ccg atc atc ccg cac tac aag ctc aac      912
His Gln Ile His His Leu Phe Pro Ile Ile Pro His Tyr Lys Leu Asn
                    290                 295                 300 gac gcc acg gcg gcg ttt gcc aag gcg ttc cca gag ctc gtg cgc aag      960
Asp Ala Thr Ala Ala Phe Ala Lys Ala Phe Pro Glu Leu Val Arg Lys
305                 310                 315                 320 aac gcg gcg ccg atc atc ccg acg ttc ttc cgc atg gcc gcc atg tac     1008
Asn Ala Ala Pro Ile Ile Pro Thr Phe Phe Arg Met Ala Ala Met Tyr
                    325                 330                 335 gcc aag tac ggc gtg gtc gac acg gac gcc aag acg ttc acg ctc aag     1056
Ala Lys Tyr Gly Val Val Asp Thr Asp Ala Lys Thr Phe Thr Leu Lys
                    340                 345                 350 gaa gcc aag gcc gcc gcc aag acc aag tcg agc taa                      1092
Glu Ala Lys Ala Ala Ala Lys Thr Lys Ser Ser
                    355                 360
```

<210> SEQ ID NO 24
<211> LENGTH: 363
<212> TYPE: PRT
<213> ORGANISM: Pythium irregulare

<400> SEQUENCE: 24

Met Ala Ser Thr Ser Ala Ala Gln Asp Ala Ala Pro Tyr Glu Phe Pro
1               5                   10                  15

Ser Leu Thr Glu Ile Lys Arg Ala Leu Pro Ser Glu Cys Phe Glu Ala
                20                  25                  30

Ser Val Pro Leu Ser Leu Tyr Tyr Thr Ala Arg Ser Leu Ala Leu Ala
            35                  40                  45

Gly Ser Leu Ala Val Ala Leu Ser Tyr Ala Arg Ala Leu Pro Leu Val
        50                  55                  60

Gln Ala Asn Ala Leu Leu Asp Ala Thr Leu Cys Thr Gly Tyr Val Leu
65                  70                  75                  80

Leu Gln Gly Ile Val Phe Trp Gly Phe Thr Val Gly His Asp Cys
                85                  90                  95

Gly His Gly Ala Phe Ser Arg Ser His Val Leu Asn Phe Ser Val Gly
            100                 105                 110

Thr Leu Met His Ser Ile Ile Leu Thr Pro Phe Glu Ser Trp Lys Leu
        115                 120                 125

Ser His Arg His His His Lys Asn Thr Gly Asn Ile Asp Lys Asp Glu
    130                 135                 140

Ile Phe Tyr Pro Gln Arg Glu Ala Asp Ser His Pro Val Ser Arg His
145                 150                 155                 160

Leu Val Met Ser Leu Gly Ser Ala Trp Phe Ala Tyr Leu Phe Ala Gly
                165                 170                 175

Phe Pro Pro Arg Thr Met Asn His Phe Asn Pro Trp Glu Ala Met Tyr
            180                 185                 190

Val Arg Arg Val Ala Ala Val Ile Ile Ser Leu Gly Val Leu Phe Ala

Phe Ala Gly Leu Tyr Ser Tyr Leu Thr Phe Val Leu Gly Phe Thr Thr
        195                 200                 205
Met Ala Ile Tyr Tyr Phe Gly Pro Leu Phe Val Phe Ala Thr Met Leu
225                 230                 235                 240
Val Val Thr Thr Phe Leu His His Asn Asp Glu Glu Thr Pro Trp Tyr
                    245                 250                 255
Ala Asp Ser Glu Trp Thr Tyr Val Lys Gly Asn Leu Ser Ser Val Asp
                260                 265                 270
Arg Ser Tyr Gly Ala Leu Ile Asp Asn Leu Ser His Asn Ile Gly Thr
                275                 280                 285
His Gln Ile His His Leu Phe Pro Ile Ile Pro His Tyr Lys Leu Asn
            290                 295                 300
Asp Ala Thr Ala Ala Phe Ala Lys Ala Phe Pro Glu Leu Val Arg Lys
305                 310                 315                 320
Asn Ala Ala Pro Ile Ile Pro Thr Phe Phe Arg Met Ala Ala Met Tyr
                    325                 330                 335
Ala Lys Tyr Gly Val Val Asp Thr Asp Ala Lys Thr Phe Thr Leu Lys
                340                 345                 350
Glu Ala Lys Ala Ala Ala Lys Thr Lys Ser Ser
                355                 360

<210> SEQ ID NO 25
<211> LENGTH: 359
<212> TYPE: PRT
<213> ORGANISM: Synechocystis sp. PCC 6803

<400> SEQUENCE: 25

Met Arg Leu Glu Ile Ser Ser Pro Gln Thr Lys Leu Pro Tyr Pro Lys
1               5                   10                  15
Thr Glu Glu Leu Pro Phe Thr Leu Gln Glu Leu Arg Asn Ala Ile Pro
                20                  25                  30
Ala Asp Cys Phe Glu Pro Ser Val Val Arg Ser Leu Gly Tyr Phe Phe
            35                  40                  45
Leu Asp Val Gly Leu Ile Ala Gly Phe Tyr Ala Leu Ala Ala Tyr Leu
        50                  55                  60
Asp Ser Trp Phe Phe Tyr Pro Ile Phe Trp Leu Ile Gln Gly Thr Leu
65              70                  75                  80
Phe Trp Ser Leu Phe Val Val Gly His Asp Cys Gly His Gly Ser Phe
                85                  90                  95
Ser Lys Ser Lys Thr Leu Asn Asn Trp Ile Gly His Leu Ser His Thr
                100                 105                 110
Pro Ile Leu Val Pro Tyr His Gly Trp Arg Ile Ser His Arg Thr His
            115                 120                 125
His Ala Asn Thr Gly Asn Ile Asp Thr Asp Glu Ser Trp Tyr Pro Val
        130                 135                 140
Ser Glu Gln Lys Tyr Asn Gln Met Ala Trp Tyr Glu Lys Leu Leu Arg
145                 150                 155                 160
Phe Tyr Leu Pro Leu Ile Ala Tyr Pro Ile Tyr Leu Phe Arg Arg Ser
                165                 170                 175
Pro Asn Arg Gln Gly Ser His Phe Met Pro Gly Ser Pro Leu Phe Arg
                180                 185                 190
Pro Gly Glu Lys Ala Ala Val Leu Thr Ser Thr Phe Ala Leu Ala Ala
            195                 200                 205

-continued

```
Phe Val Gly Phe Leu Gly Phe Leu Thr Trp Gln Phe Gly Trp Leu Phe
    210                 215                 220

Leu Leu Lys Phe Tyr Val Ala Pro Tyr Leu Val Phe Val Val Trp Leu
225                 230                 235                 240

Asp Leu Val Thr Phe Leu His His Thr Glu Asp Asn Ile Pro Trp Tyr
                245                 250                 255

Arg Gly Asp Asp Trp Tyr Phe Leu Lys Gly Ala Leu Ser Thr Ile Asp
                260                 265                 270

Arg Asp Tyr Gly Phe Ile Asn Pro Ile His His Asp Ile Gly Thr His
            275                 280                 285

Val Ala His His Ile Phe Ser Asn Met Pro His Tyr Lys Leu Arg Arg
290                 295                 300

Ala Thr Glu Ala Ile Lys Pro Ile Leu Gly Glu Tyr Arg Tyr Ser
305                 310                 315                 320

Asp Glu Pro Ile Trp Gln Ala Phe Phe Lys Ser Tyr Trp Ala Cys His
                325                 330                 335

Phe Val Pro Asn Gln Gly Ser Gly Val Tyr Tyr Gln Ser Pro Ser Asn
                340                 345                 350

Gly Gly Tyr Gln Lys Lys Pro
            355

<210> SEQ ID NO 26
<211> LENGTH: 359
<212> TYPE: PRT
<213> ORGANISM: Nostoc punctiforme

<400> SEQUENCE: 26

Met Pro Ser Asn Ile Ile Thr Phe Asn Asn Pro Leu Gly Ser Glu Lys
1               5                   10                  15

Ser Glu Asp Thr Thr Lys Leu Pro Phe Asn Leu Gln Asp Leu Lys Ala
            20                  25                  30

Ala Ile Pro Ala Glu Cys Phe Gln Pro Asn Val Lys Lys Ser Leu Phe
        35                  40                  45

Tyr Phe Phe Arg Asp Ile Leu Ile Ile Gly Leu Leu Tyr Ala Val Ala
    50                  55                  60

Ser Tyr Leu Asp Ser Trp Leu Phe Phe Pro Ile Phe Trp Leu Met Gln
65                  70                  75                  80

Gly Thr Met Phe Trp Ala Leu Phe Val Val Gly His Asp Cys Gly His
                85                  90                  95

Gln Ser Phe Ser Lys His Lys Trp Leu Asn Asp Leu Ile Gly His Leu
            100                 105                 110

Ser His Thr Pro Ile Leu Val Pro Tyr His Gly Trp Arg Ile Ser His
        115                 120                 125

Arg Thr His His Lys Asn Thr Gly Asn Ile Asp Asp Glu Ser Trp
    130                 135                 140

Tyr Pro Val Ser Glu Ser Gln Tyr Lys Glu Met Pro Leu Ala Gln Lys
145                 150                 155                 160

Ile Gly Arg Tyr Tyr Val Phe Leu Leu Ala Tyr Pro Val Tyr Leu Phe
                165                 170                 175

Lys Arg Ser Pro Asn Lys Glu Gly Ser His Phe Leu Pro Gly Ser Ser
            180                 185                 190

Leu Phe Lys Pro Ser Glu Lys Trp Asp Val Ile Thr Ser Thr Val Leu
        195                 200                 205

Leu Ile Gly Met Val Gly Leu Leu Gly Phe Leu Thr Tyr Gln Trp Gly
    210                 215                 220
```

```
Trp Met Trp Leu Leu Lys Tyr Tyr Ala Val Pro Tyr Leu Val Phe Ile
225                 230                 235                 240

Val Trp Leu Asp Leu Val Thr Phe Leu His Thr Glu Pro Glu Leu
                245                 250                 255

Pro Trp Tyr Arg Gly Glu Asp Trp Thr Phe Leu Lys Gly Ala Ile Ser
                260                 265                 270

Ser Ile Asp Arg Asp Tyr Gly Leu Val Asn His Ile His His Asp Ile
            275                 280                 285

Gly Thr His Val Ala His Ile Phe Leu Asn Ile Pro His Tyr Asn
            290                 295                 300

Leu Leu Lys Ala Thr Glu Ala Ile Lys Pro Val Met Gly Glu Tyr Phe
305                 310                 315                 320

His Lys Ser Glu Glu Pro Ile Trp Lys Ser Leu Trp Asn Ser Cys Ile
                325                 330                 335

Ser Cys His Phe Val Pro Asp Thr Gly Ser Arg Val Tyr Tyr Thr Ser
                340                 345                 350

Asn Asn Lys Leu Ala Lys Asp
            355

<210> SEQ ID NO 27
<211> LENGTH: 359
<212> TYPE: PRT
<213> ORGANISM: Nostoc sp. PCC 7120

<400> SEQUENCE: 27

Met Gln Ser Thr Thr Ile Pro Ser Asp Asn Ser Pro Ser Phe Gly Gln
1               5                   10                  15

Ser Glu Asn Thr Thr Thr Leu Pro Phe Thr Leu Gln Asp Leu Lys Ala
                20                  25                  30

Ala Ile Pro Ala Glu Cys Phe Gln Pro Asn Val Ser Lys Ser Leu Phe
            35                  40                  45

Tyr Phe Phe Arg Asp Val Leu Ile Val Gly Leu Tyr Ala Val Ala
    50                  55                  60

His Tyr Leu Asp Ser Trp Tyr Phe Trp Pro Ile Phe Trp Leu Ile Gln
65                  70                  75                  80

Gly Thr Met Phe Trp Ala Leu Phe Val Val Gly His Asp Cys Gly His
                85                  90                  95

Gln Ser Phe Ser Lys His Lys Trp Leu Asn Asp Leu Ile Gly His Leu
            100                 105                 110

Thr His Thr Phe Ile Leu Val Pro Tyr His Gly Trp Arg Ile Ser His
            115                 120                 125

Arg Thr His His Lys Asn Thr Gly Asn Ile Asp Asn Asp Glu Ser Trp
130                 135                 140

Tyr Pro Val Thr Gln Ser Gln Tyr Lys Glu Met Pro Leu Gly Gln Lys
145                 150                 155                 160

Ile Gly Arg Tyr Tyr Val Phe Leu Leu Ala Tyr Pro Val Tyr Leu Phe
                165                 170                 175

Lys Arg Ser Pro Asn Lys Glu Gly Ser His Phe Leu Pro Ser Ser Ser
            180                 185                 190

Leu Phe Lys Pro Ser Glu Lys Trp Asp Val Ile Thr Ser Thr Val Leu
            195                 200                 205

Trp Ser Cys Met Val Gly Leu Leu Gly Phe Leu Thr Tyr Gln Trp Gly
210                 215                 220

Trp Met Trp Leu Leu Lys Tyr Tyr Ala Ala Pro Tyr Ile Val Phe Val
```

```
            225                 230                 235                 240

Ile Trp Leu Asp Leu Val Thr Phe Leu His His Thr Glu Ala Asp Leu
                        245                 250                 255

Pro Trp Tyr Arg Gly Glu Asp Trp Thr Phe Leu Lys Gly Ala Ile Ser
                        260                 265                 270

Ser Ile Asp Arg Asn Tyr Gly Leu Val Asn His Ile His Asp Ile
                        275                 280                 285

Gly Thr His Val Ala His His Ile Phe Leu Asn Ile Pro His Tyr Asn
                        290                 295                 300

Leu Leu Lys Ala Thr Glu Ala Ile Lys Pro Val Met Gly Glu Tyr Tyr
        305                 310                 315                 320

Arg Lys Ser Glu Glu Pro Ile Trp Lys Ser Leu Trp Arg Ser Cys Val
                        325                 330                 335

Ser Cys His Phe Val Pro Asp Thr Gly Gly Lys Val Tyr Tyr Thr Ser
                        340                 345                 350

Asn Asn Gln Val Val Asn Lys
                        355

<210> SEQ ID NO 28
<211> LENGTH: 358
<212> TYPE: PRT
<213> ORGANISM: Unknown
<220> FEATURE:
<223> OTHER INFORMATION: Variant of SEQ ID NO: 10

<400> SEQUENCE: 28

Met Ala Glu Asp Lys Thr Lys Val Glu Phe Pro Thr Leu Thr Glu Leu
        1               5                   10                  15

Lys His Ser Ile Pro Asn Ala Cys Phe Glu Ser Asn Leu Gly Leu Ser
                        20                  25                  30

Leu Tyr Tyr Thr Ala Arg Ala Ile Phe Asn Ala Ser Ala Ser Ala Ala
                        35                  40                  45

Leu Leu Tyr Ala Ala Arg Ser Thr Pro Phe Ile Ala Asp Asn Val Leu
                        50                  55                  60

Leu His Ala Leu Val Cys Ala Thr Tyr Ile Tyr Val Gln Gly Val Ile
        65                  70                  75                  80

Phe Trp Gly Phe Phe Thr Val Gly His Asp Cys Gly His Ser Ala Phe
                        85                  90                  95

Ser Arg Tyr His Ser Val Asn Phe Ile Ile Gly Cys Ile Met His Ser
                        100                 105                 110

Ala Ile Leu Thr Pro Phe Glu Ser Trp Arg Val Thr His Arg His His
                        115                 120                 125

His Lys Asn Thr Gly Asn Ile Asp Lys Asp Glu Ile Phe Tyr Pro His
        130                 135                 140

Arg Ser Val Lys Asp Leu Gln Asp Val Arg Gln Trp Val Tyr Thr Leu
        145                 150                 155                 160

Gly Gly Ala Trp Phe Val Tyr Leu Lys Val Gly Tyr Ala Pro Arg Thr
                        165                 170                 175

Met Ser His Phe Asp Pro Trp Asp Pro Leu Leu Leu Arg Arg Ala Ser
                        180                 185                 190

Ala Val Ile Val Ser Leu Gly Val Trp Ala Ala Phe Phe Ala Ala Tyr
                        195                 200                 205

Ala Tyr Leu Thr Tyr Ser Leu Gly Phe Ala Val Met Gly Leu Tyr Tyr
                        210                 215                 220

Tyr Ala Pro Leu Phe Val Phe Ala Ser Phe Leu Val Ile Thr Thr Phe
```

-continued

```
                225                 230                 235                 240
Leu His His Asn Asp Glu Ala Thr Pro Trp Tyr Gly Asp Ser Glu Trp
                    245                 250                 255

Thr Tyr Val Lys Gly Asn Leu Ser Ser Val Asp Arg Ser Tyr Gly Ala
                    260                 265                 270

Phe Val Asp Asn Leu Ser His Ile Gly Thr His Gln Val His His
                275                 280                 285

Leu Phe Pro Ile Ile Pro His Tyr Lys Leu Asn Glu Ala Thr Lys His
            290                 295                 300

Phe Ala Ala Ala Tyr Pro His Leu Val Arg Arg Asn Asp Glu Pro Ile
305                 310                 315                 320

Ile Thr Ala Phe Phe Lys Thr Ala His Leu Phe Val Asn Tyr Gly Ala
                    325                 330                 335

Val Pro Glu Thr Ala Gln Ile Phe Thr Leu Lys Glu Ser Ala Ala Ala
                340                 345                 350

Ala Lys Ala Lys Ser Asp
            355
```

<210> SEQ ID NO 29
<211> LENGTH: 359
<212> TYPE: PRT
<213> ORGANISM: Synechocystis sp. PCC 6803

<400> SEQUENCE: 29

```
Val Arg Leu Glu Ile Ser Ser Pro Gln Thr Lys Leu Pro Tyr Pro Lys
1               5                   10                  15

Thr Glu Glu Leu Pro Phe Thr Leu Gln Glu Leu Arg Asn Ala Ile Pro
                20                  25                  30

Ala Asp Cys Phe Glu Pro Ser Val Val Arg Ser Leu Gly Tyr Phe Phe
            35                  40                  45

Leu Asp Val Gly Leu Ile Ala Gly Phe Tyr Ala Leu Ala Ala Tyr Leu
        50                  55                  60

Asp Ser Trp Phe Phe Tyr Pro Ile Phe Trp Leu Ile Gln Gly Thr Leu
65                  70                  75                  80

Phe Trp Ser Leu Phe Val Val Gly His Asp Cys Gly His Gly Ser Phe
                85                  90                  95

Ser Lys Ser Lys Thr Leu Asn Asn Trp Ile Gly His Leu Ser His Thr
            100                 105                 110

Pro Ile Leu Val Pro Tyr His Gly Trp Arg Ile Ser His Arg Thr His
        115                 120                 125

His Ala Asn Thr Gly Asn Ile Asp Thr Asp Glu Ser Trp Tyr Pro Val
130                 135                 140

Ser Glu Gln Lys Tyr Asn Gln Met Ala Trp Tyr Glu Lys Leu Leu Arg
145                 150                 155                 160

Phe Tyr Leu Pro Leu Ile Ala Tyr Pro Ile Tyr Leu Phe Arg Arg Ser
                165                 170                 175

Pro Asn Arg Gln Gly Ser His Phe Met Pro Gly Ser Pro Leu Phe Arg
            180                 185                 190

Pro Gly Glu Lys Ala Ala Val Leu Thr Ser Thr Phe Ala Leu Ala Ala
        195                 200                 205

Phe Val Gly Phe Leu Gly Phe Leu Thr Trp Gln Phe Gly Trp Leu Phe
    210                 215                 220

Leu Leu Lys Phe Tyr Val Ala Pro Tyr Leu Val Phe Val Val Trp Leu
225                 230                 235                 240
```

```
Asp Leu Val Thr Phe Leu His His Thr Glu Asp Asn Ile Pro Trp Tyr
                245                 250                 255

Arg Gly Asp Asp Trp Tyr Phe Leu Lys Gly Ala Leu Ser Thr Ile Asp
            260                 265                 270

Arg Asp Tyr Gly Phe Ile Asn Pro Ile His His Asp Ile Gly Thr His
        275                 280                 285

Val Ala His His Ile Phe Ser Asn Met Pro His Tyr Lys Leu Arg Arg
    290                 295                 300

Ala Thr Glu Ala Ile Lys Pro Ile Leu Gly Glu Tyr Tyr Arg Tyr Ser
305                 310                 315                 320

Asp Glu Pro Ile Trp Gln Ala Phe Phe Lys Ser Tyr Trp Ala Cys His
                325                 330                 335

Phe Val Pro Asn Gln Gly Ser Gly Val Tyr Tyr Gln Ser Pro Ser Asn
            340                 345                 350

Gly Gly Tyr Gln Lys Lys Pro
        355

<210> SEQ ID NO 30
<211> LENGTH: 1077
<212> TYPE: DNA
<213> ORGANISM: Saprolegnia diclina
<220> FEATURE:
<221> NAME/KEY: CDS
<222> LOCATION: (1)..(1077)

<400> SEQUENCE: 30 atg act gag gat aag acg aag gtc gag ttc ccg acg ctc acg gag ctc      48
Met Thr Glu Asp Lys Thr Lys Val Glu Phe Pro Thr Leu Thr Glu Leu
 1               5                  10                  15 aag cac tcg atc ccg aac gcg tgc ttt gag tcg aac ctc ggc ctc tcg      96
Lys His Ser Ile Pro Asn Ala Cys Phe Glu Ser Asn Leu Gly Leu Ser
                20                  25                  30 ctc tac tac acg gcc cgc gcg atc ttc aac gcg tcg gcc tcg gcg gcg     144
Leu Tyr Tyr Thr Ala Arg Ala Ile Phe Asn Ala Ser Ala Ser Ala Ala
            35                  40                  45 ctg ctc tac gcg gcg cgc tcg acg ccg ttc att gcc gat aac gtt ctg     192
Leu Leu Tyr Ala Ala Arg Ser Thr Pro Phe Ile Ala Asp Asn Val Leu
        50                  55                  60 ctc cac gcg ctc gtt tgc gcc acc tac atc tac gtg cag ggc gtc atc     240
Leu His Ala Leu Val Cys Ala Thr Tyr Ile Tyr Val Gln Gly Val Ile
65                  70                  75                  80 ttc tgg ggc ttc ttc acg gtc ggc cac gac tgc ggc cac tcg gcc ttc     288
Phe Trp Gly Phe Phe Thr Val Gly His Asp Cys Gly His Ser Ala Phe
                85                  90                  95 tcg cgc tac cac agc gtc aac ttt atc atc ggc tgc atc atg cac tct     336
Ser Arg Tyr His Ser Val Asn Phe Ile Ile Gly Cys Ile Met His Ser
            100                 105                 110 gcg att ttg acg ccg ttc gag agc tgg cgc gtg acg cac cgc cac cac     384
Ala Ile Leu Thr Pro Phe Glu Ser Trp Arg Val Thr His Arg His His
        115                 120                 125 cac aag aac acg ggc aac att gat aag gac gag atc ttt tac ccg cac     432
His Lys Asn Thr Gly Asn Ile Asp Lys Asp Glu Ile Phe Tyr Pro His
    130                 135                 140 cgg tcg gtc aag gac ctc cag gac gtg cgc caa tgg gtc tac acg ctc     480
Arg Ser Val Lys Asp Leu Gln Asp Val Arg Gln Trp Val Tyr Thr Leu
145                 150                 155                 160 ggc ggt gcg tgg ttt gtc tac ttg aag gtc ggg tat gcc ccg cgc acg     528
Gly Gly Ala Trp Phe Val Tyr Leu Lys Val Gly Tyr Ala Pro Arg Thr
                165                 170                 175
```

-continued

| | | |
|---|---|---|
| atg agc cac ttt gac ccg tgg gac ccg ctc ctc ctt cgc cgc gcg tcg<br>Met Ser His Phe Asp Pro Trp Asp Pro Leu Leu Leu Arg Arg Ala Ser<br>180                              185                                  190 | | 576 |
| gcc gtc atc gtg tcg ctc ggc gtc tgg gcc gcc ttc ttc gcc gcg tac<br>Ala Val Ile Val Ser Leu Gly Val Trp Ala Ala Phe Phe Ala Ala Tyr<br>              195                          200                          205 | | 624 |
| gcg tac ctc aca tac tcg ctc ggc ttt gcc gtc atg ggc ctc tac tac<br>Ala Tyr Leu Thr Tyr Ser Leu Gly Phe Ala Val Met Gly Leu Tyr Tyr<br>210                              215                                  220 | | 672 |
| tat gcg ccg ctc ttt gtc ttt gct tcg ttc ctc gtc att acg acc ttc<br>Tyr Ala Pro Leu Phe Val Phe Ala Ser Phe Leu Val Ile Thr Thr Phe<br>225                              230                              235                  240 | | 720 |
| ttg cac cac aac gac gaa gcg acg ccg tgg tac ggc gac tcg gag tgg<br>Leu His His Asn Asp Glu Ala Thr Pro Trp Tyr Gly Asp Ser Glu Trp<br>                          245                          250                          255 | | 768 |
| acg tac gtc aag ggc aac ctc tcg agc gtc gac cgc tcg tac ggc gcg<br>Thr Tyr Val Lys Gly Asn Leu Ser Ser Val Asp Arg Ser Tyr Gly Ala<br>260                              265                                  270 | | 816 |
| ttc gtg gac aac ctg agc cac cac att ggc acg cac cag gtc cac cac<br>Phe Val Asp Asn Leu Ser His His Ile Gly Thr His Gln Val His His<br>              275                          280                          285 | | 864 |
| ttg ttc ccg atc att ccg cac tac aag ctc aac gaa gcc acc aag cac<br>Leu Phe Pro Ile Ile Pro His Tyr Lys Leu Asn Glu Ala Thr Lys His<br>290                              295                              300 | | 912 |
| ttt gcg gcc gcg tac ccg cac ctc gtg cgc agg aac gac gag ccc atc<br>Phe Ala Ala Ala Tyr Pro His Leu Val Arg Arg Asn Asp Glu Pro Ile<br>305                              310                              315                  320 | | 960 |
| atc acg gcc ttc ttc aag acc gcg cac ctc ttt gtc aac tac ggc gct<br>Ile Thr Ala Phe Phe Lys Thr Ala His Leu Phe Val Asn Tyr Gly Ala<br>                          325                          330                          335 | | 1008 |
| gtg ccc gag acg gcg cag atc ttc acg ctc aaa gag tcg gcc gcg gcc<br>Val Pro Glu Thr Ala Gln Ile Phe Thr Leu Lys Glu Ser Ala Ala Ala<br>340                              345                              350 | | 1056 |
| gcc aag gcc aag tcg gac taa<br>Ala Lys Ala Lys Ser Asp<br>        355 | | 1077 |

```
<210> SEQ ID NO 31
<211> LENGTH: 358
<212> TYPE: PRT
<213> ORGANISM: Saprolegnia diclina

<400> SEQUENCE: 31

Met Thr Glu Asp Lys Thr Lys Val Glu Phe Pro Thr Leu Thr Glu Leu
1               5                   10                  15

Lys His Ser Ile Pro Asn Ala Cys Phe Glu Ser Asn Leu Gly Leu Ser
            20                  25                  30

Leu Tyr Tyr Thr Ala Arg Ala Ile Phe Asn Ala Ser Ala Ser Ala Ala
        35                  40                  45

Leu Leu Tyr Ala Ala Arg Ser Thr Pro Phe Ile Ala Asp Asn Val Leu
    50                  55                  60

Leu His Ala Leu Val Cys Ala Thr Tyr Ile Tyr Val Gln Gly Val Ile
65                  70                  75                  80

Phe Trp Gly Phe Phe Thr Val Gly His Asp Cys Gly His Ser Ala Phe
                85                  90                  95

Ser Arg Tyr His Ser Val Asn Phe Ile Ile Gly Cys Ile Met His Ser
            100                 105                 110

Ala Ile Leu Thr Pro Phe Glu Ser Trp Arg Val Thr His Arg His
        115                 120                 125
```

His Lys Asn Thr Gly Asn Ile Asp Lys Asp Glu Ile Phe Tyr Pro His
            130                 135                 140

Arg Ser Val Lys Asp Leu Gln Asp Val Arg Gln Trp Val Tyr Thr Leu
145                 150                 155                 160

Gly Gly Ala Trp Phe Val Tyr Leu Lys Val Gly Tyr Ala Pro Arg Thr
                165                 170                 175

Met Ser His Phe Asp Pro Trp Asp Pro Leu Leu Leu Arg Arg Ala Ser
            180                 185                 190

Ala Val Ile Val Ser Leu Gly Val Trp Ala Ala Phe Phe Ala Ala Tyr
                195                 200                 205

Ala Tyr Leu Thr Tyr Ser Leu Gly Phe Ala Val Met Gly Leu Tyr Tyr
            210                 215                 220

Tyr Ala Pro Leu Phe Val Phe Ala Ser Phe Leu Val Ile Thr Thr Phe
225                 230                 235                 240

Leu His His Asn Asp Glu Ala Thr Pro Trp Tyr Gly Asp Ser Glu Trp
                245                 250                 255

Thr Tyr Val Lys Gly Asn Leu Ser Ser Val Asp Arg Ser Tyr Gly Ala
            260                 265                 270

Phe Val Asp Asn Leu Ser His His Ile Gly Thr His Gln Val His His
                275                 280                 285

Leu Phe Pro Ile Ile Pro His Tyr Lys Leu Asn Glu Ala Thr Lys His
            290                 295                 300

Phe Ala Ala Ala Tyr Pro His Leu Val Arg Arg Asn Asp Glu Pro Ile
305                 310                 315                 320

Ile Thr Ala Phe Phe Lys Thr Ala His Leu Phe Val Asn Tyr Gly Ala
                325                 330                 335

Val Pro Glu Thr Ala Gln Ile Phe Thr Leu Lys Glu Ser Ala Ala Ala
            340                 345                 350

Ala Lys Ala Lys Ser Asp
            355

<210> SEQ ID NO 32
<211> LENGTH: 361
<212> TYPE: PRT
<213> ORGANISM: Phytophthora infestans

<400> SEQUENCE: 32

Met Ala Thr Lys Glu Ala Tyr Val Phe Pro Thr Leu Thr Glu Ile Lys
1               5                   10                  15

Arg Ser Leu Pro Lys Asp Cys Phe Glu Ala Ser Val Pro Leu Ser Leu
                20                  25                  30

Tyr Tyr Thr Val Arg Cys Leu Val Ile Ala Val Ala Leu Thr Phe Gly
            35                  40                  45

Leu Asn Tyr Ala Arg Ala Leu Pro Glu Val Glu Ser Phe Trp Ala Leu
50                  55                  60

Asp Ala Ala Leu Cys Thr Gly Tyr Ile Leu Leu Gln Gly Ile Val Phe
65                  70                  75                  80

Trp Gly Phe Phe Thr Val Gly His Asp Ala Gly His Gly Ala Phe Ser
                85                  90                  95

Arg Tyr His Leu Leu Asn Phe Val Gly Thr Phe Met His Ser Leu
                100                 105                 110

Ile Leu Thr Pro Phe Glu Ser Trp Lys Leu Thr His Arg His His
            115                 120                 125

Lys Asn Thr Gly Asn Ile Asp Arg Asp Glu Val Phe Tyr Pro Gln Arg

```
                130                 135                 140
Lys Ala Asp Asp His Pro Leu Ser Arg Asn Leu Ile Leu Ala Leu Gly
145                 150                 155                 160

Ala Ala Trp Leu Ala Tyr Leu Val Glu Gly Phe Pro Pro Arg Lys Val
                165                 170                 175

Asn His Phe Asn Pro Phe Glu Pro Leu Phe Val Arg Gln Val Ser Ala
            180                 185                 190

Val Val Ile Ser Leu Leu Ala His Phe Phe Val Ala Gly Leu Ser Ile
        195                 200                 205

Tyr Leu Ser Leu Gln Leu Gly Leu Lys Thr Met Ala Ile Tyr Tyr Tyr
    210                 215                 220

Gly Pro Val Phe Val Phe Gly Ser Met Leu Val Ile Thr Thr Phe Leu
225                 230                 235                 240

His His Asn Asp Glu Glu Thr Pro Trp Tyr Ala Asp Ser Glu Trp Thr
                245                 250                 255

Tyr Val Lys Gly Asn Leu Ser Ser Val Asp Arg Ser Tyr Gly Ala Leu
            260                 265                 270

Ile Asp Asn Leu Ser His Asn Ile Gly Thr His Gln Ile His His Leu
        275                 280                 285

Phe Pro Ile Ile Pro His Tyr Lys Leu Lys Lys Ala Thr Ala Ala Phe
    290                 295                 300

His Gln Ala Phe Pro Glu Leu Val Arg Lys Ser Asp Glu Pro Ile Ile
305                 310                 315                 320

Lys Ala Phe Phe Arg Val Gly Arg Leu Tyr Ala Asn Tyr Gly Val Val
                325                 330                 335

Asp Gln Glu Ala Lys Leu Phe Thr Leu Lys Glu Ala Lys Ala Ala Thr
            340                 345                 350

Glu Ala Ala Ala Lys Thr Lys Ser Thr
        355                 360

<210> SEQ ID NO 33
<211> LENGTH: 1080
<212> TYPE: DNA
<213> ORGANISM: Anabaena variabilis ATCC 29413
<220> FEATURE:
<221> NAME/KEY: CDS
<222> LOCATION: (1)..(1080)
<223> OTHER INFORMATION: transl_table=11

<400> SEQUENCE: 33 gtg caa tca act aca atc ccc tcc gat aat tct cct agc ttt gac caa     48
Val Gln Ser Thr Thr Ile Pro Ser Asp Asn Ser Pro Ser Phe Asp Gln
1               5                   10                  15 tca gag aat aca act acg ctg cca ttt act ctt cag gat tta aaa gca     96
Ser Glu Asn Thr Thr Thr Leu Pro Phe Thr Leu Gln Asp Leu Lys Ala
            20                  25                  30 gct att ccg gct gaa tgt ttt caa cca aac gtg ggc aaa tca ctg ttt    144
Ala Ile Pro Ala Glu Cys Phe Gln Pro Asn Val Gly Lys Ser Leu Phe
        35                  40                  45 tac ttt ttt cgt gat gta gtg att gtt agc tca cta tac gca gtt gct    192
Tyr Phe Phe Arg Asp Val Val Ile Val Ser Ser Leu Tyr Ala Val Ala
    50                  55                  60 cat tac cta gat tct tgg tat ttc tgg cca att ttc tgg tta atg caa    240
His Tyr Leu Asp Ser Trp Tyr Phe Trp Pro Ile Phe Trp Leu Met Gln
65                  70                  75                  80 gga acg atg ttt tgg gct ttg ttt gtg gtt gga cat gac tgc gga cac    288
Gly Thr Met Phe Trp Ala Leu Phe Val Val Gly His Asp Cys Gly His
                85                  90                  95
```

```
caa tct ttt tct aag cat aaa tgg ctc aat gat tta gtt ggg cat ctg      336
Gln Ser Phe Ser Lys His Lys Trp Leu Asn Asp Leu Val Gly His Leu
            100                 105                 110 act cac acc ttc ata tta gtc cct tat cac ggt tgg cgt att agt cac      384
Thr His Thr Phe Ile Leu Val Pro Tyr His Gly Trp Arg Ile Ser His
        115                 120                 125 aga act cat cac aaa aat act ggc aat atc gat aat gat gaa agc tgg      432
Arg Thr His His Lys Asn Thr Gly Asn Ile Asp Asn Asp Glu Ser Trp
130                 135                 140 tat cct gtg act gag tcg caa tac aag gaa atg cca tta ggg caa aag      480
Tyr Pro Val Thr Glu Ser Gln Tyr Lys Glu Met Pro Leu Gly Gln Lys
145                 150                 155                 160 ata ggc cgt tat tac gtc ttt cta ctg gct tat cca gtg tat ttg ttt      528
Ile Gly Arg Tyr Tyr Val Phe Leu Leu Ala Tyr Pro Val Tyr Leu Phe
                165                 170                 175 aag cgt tct cct aat aag gaa ggc tct cat ttt tta cct agt agc cct      576
Lys Arg Ser Pro Asn Lys Glu Gly Ser His Phe Leu Pro Ser Ser Pro
            180                 185                 190 ctt ttc aag cca tca gaa aaa tgg gat gtc atc acc agc act gta ctg      624
Leu Phe Lys Pro Ser Glu Lys Trp Asp Val Ile Thr Ser Thr Val Leu
        195                 200                 205 tgg act tgt atg gtt gct tcg tta ggt ttc cta act tat caa tgg ggc      672
Trp Thr Cys Met Val Ala Ser Leu Gly Phe Leu Thr Tyr Gln Trp Gly
210                 215                 220 tgg atg tgg ttg tta aaa tac tac gct gca cca tat atc gtg ttt gta      720
Trp Met Trp Leu Leu Lys Tyr Tyr Ala Ala Pro Tyr Ile Val Phe Val
225                 230                 235                 240 atc tgg ctt gat tta gtc aca ttc cta cac cac act gag gca gat atc      768
Ile Trp Leu Asp Leu Val Thr Phe Leu His His Thr Glu Ala Asp Ile
                245                 250                 255 ccc tgg tat cgt ggc gaa gat tgg act ttc ctc aaa ggt gca att tct      816
Pro Trp Tyr Arg Gly Glu Asp Trp Thr Phe Leu Lys Gly Ala Ile Ser
            260                 265                 270 agc att gac cgc aat tat ggt tta gtc aat cat atc cat cat gat atc      864
Ser Ile Asp Arg Asn Tyr Gly Leu Val Asn His Ile His His Asp Ile
        275                 280                 285 ggc act cat gta gca cac cac att ttc ttg aat atc cct cac tat aat      912
Gly Thr His Val Ala His His Ile Phe Leu Asn Ile Pro His Tyr Asn
290                 295                 300 ttg ctg aag gct acc gag gct att aaa cca gtc atg ggt gaa tat tac      960
Leu Leu Lys Ala Thr Glu Ala Ile Lys Pro Val Met Gly Glu Tyr Tyr
305                 310                 315                 320 cgc aag tca gaa gaa cct att tgg aag tca ttg tgg cgt tct tgc gtg     1008
Arg Lys Ser Glu Glu Pro Ile Trp Lys Ser Leu Trp Arg Ser Cys Val
                325                 330                 335 agt tgc cat ttt gtc ccc gat act ggt ggg aaa gtt tac tac act tct     1056
Ser Cys His Phe Val Pro Asp Thr Gly Gly Lys Val Tyr Tyr Thr Ser
            340                 345                 350 aac aat caa gta gtg aat aag tag                                     1080
Asn Asn Gln Val Val Asn Lys
        355
```

<210> SEQ ID NO 34
<211> LENGTH: 359
<212> TYPE: PRT
<213> ORGANISM: Anabaena variabilis ATCC 29413

<400> SEQUENCE: 34

```
Val Gln Ser Thr Thr Ile Pro Ser Asp Asn Ser Pro Ser Phe Asp Gln
1               5                   10                  15
```

Ser Glu Asn Thr Thr Thr Leu Pro Phe Thr Leu Gln Asp Leu Lys Ala
            20                  25                  30

Ala Ile Pro Ala Glu Cys Phe Gln Pro Asn Val Gly Lys Ser Leu Phe
        35                  40                  45

Tyr Phe Arg Asp Val Val Ile Val Ser Ser Leu Tyr Ala Val Ala
50                  55                  60

His Tyr Leu Asp Ser Trp Tyr Phe Trp Pro Ile Phe Trp Leu Met Gln
65                  70                  75                  80

Gly Thr Met Phe Trp Ala Leu Phe Val Val Gly His Asp Cys Gly His
                85                  90                  95

Gln Ser Phe Ser Lys His Lys Trp Leu Asn Asp Leu Val Gly His Leu
            100                 105                 110

Thr His Thr Phe Ile Leu Val Pro Tyr His Gly Trp Arg Ile Ser His
            115                 120                 125

Arg Thr His His Lys Asn Thr Gly Asn Ile Asp Asn Asp Glu Ser Trp
    130                 135                 140

Tyr Pro Val Thr Glu Ser Gln Tyr Lys Glu Met Pro Leu Gly Gln Lys
145                 150                 155                 160

Ile Gly Arg Tyr Tyr Val Phe Leu Leu Ala Tyr Pro Val Tyr Leu Phe
                165                 170                 175

Lys Arg Ser Pro Asn Lys Glu Gly Ser His Phe Leu Pro Ser Ser Pro
            180                 185                 190

Leu Phe Lys Pro Ser Glu Lys Trp Asp Val Ile Thr Ser Thr Val Leu
        195                 200                 205

Trp Thr Cys Met Val Ala Ser Leu Gly Phe Leu Thr Tyr Gln Trp Gly
210                 215                 220

Trp Met Trp Leu Leu Lys Tyr Tyr Ala Ala Pro Tyr Ile Val Phe Val
225                 230                 235                 240

Ile Trp Leu Asp Leu Val Thr Phe Leu His His Thr Glu Ala Asp Ile
                245                 250                 255

Pro Trp Tyr Arg Gly Glu Asp Trp Thr Phe Leu Lys Gly Ala Ile Ser
            260                 265                 270

Ser Ile Asp Arg Asn Tyr Gly Leu Val Asn His Ile His His Asp Ile
        275                 280                 285

Gly Thr His Val Ala His His Ile Phe Leu Asn Ile Pro His Tyr Asn
290                 295                 300

Leu Leu Lys Ala Thr Glu Ala Ile Lys Pro Val Met Gly Glu Tyr Tyr
305                 310                 315                 320

Arg Lys Ser Glu Glu Pro Ile Trp Lys Ser Leu Trp Arg Ser Cys Val
                325                 330                 335

Ser Cys His Phe Val Pro Asp Thr Gly Gly Lys Val Tyr Tyr Thr Ser
            340                 345                 350

Asn Asn Gln Val Val Asn Lys
        355

<210> SEQ ID NO 35
<211> LENGTH: 1080
<212> TYPE: DNA
<213> ORGANISM: Nostoc sp
<220> FEATURE:
<221> NAME/KEY: CDS
<222> LOCATION: (1)..(1080)
<223> OTHER INFORMATION: transl_table=11

<400> SEQUENCE: 35

```
                                                           -continued gtg caa tta gat acc atc agt ttc aac aat cct ctt aac agt gaa act      48
Val Gln Leu Asp Thr Ile Ser Phe Asn Asn Pro Leu Asn Ser Glu Thr
1               5                  10                  15 tct gag gat aca act aaa tta cct ttc aca ctt ggg gat tta aaa gct      96
Ser Glu Asp Thr Thr Lys Leu Pro Phe Thr Leu Gly Asp Leu Lys Ala
            20                  25                  30 gca ata cct gct gaa tgc ttt cag ccc aat gtg aca aaa tca ctt ttt     144
Ala Ile Pro Ala Glu Cys Phe Gln Pro Asn Val Thr Lys Ser Leu Phe
        35                  40                  45 tac ttt ttt cgt gat atc ctg att atc ggt ctg ctt tat gca gtt gct     192
Tyr Phe Phe Arg Asp Ile Leu Ile Ile Gly Leu Leu Tyr Ala Val Ala
50                  55                  60 tct tac ctg gat tct tgg ctt ttc ttt ccg att ttc tgg cta atg caa     240
Ser Tyr Leu Asp Ser Trp Leu Phe Phe Pro Ile Phe Trp Leu Met Gln
65                  70                  75                  80 gga acg atg ttt tgg gct ttg ttt gta gtc ggg cat gac tgc gga cac     288
Gly Thr Met Phe Trp Ala Leu Phe Val Val Gly His Asp Cys Gly His
                85                  90                  95 caa tct ttt tct aag cag aaa tgg ctc aat gat ttg att gga cat ctt     336
Gln Ser Phe Ser Lys Gln Lys Trp Leu Asn Asp Leu Ile Gly His Leu
            100                 105                 110 tct cac aca cca ata ctt gtt cct tat cat ggt tgg cgg att agt cac     384
Ser His Thr Pro Ile Leu Val Pro Tyr His Gly Trp Arg Ile Ser His
        115                 120                 125 aga act cac cac aaa aat act ggc aat att gat aac gat gaa agc tgg     432
Arg Thr His His Lys Asn Thr Gly Asn Ile Asp Asn Asp Glu Ser Trp
130                 135                 140 tat cct gtg aca gaa tcc caa tat aaa gat atg cct tta gcc caa aag     480
Tyr Pro Val Thr Glu Ser Gln Tyr Lys Asp Met Pro Leu Ala Gln Lys
145                 150                 155                 160 ata ggc aga tat tat gtt ttt ctc ttg gct tat cct gta tat ctg ttt     528
Ile Gly Arg Tyr Tyr Val Phe Leu Leu Ala Tyr Pro Val Tyr Leu Phe
                165                 170                 175 aag cgt tct cct aat aaa gaa ggc tcc cac ttt tta ccc agt agt tca     576
Lys Arg Ser Pro Asn Lys Glu Gly Ser His Phe Leu Pro Ser Ser Ser
            180                 185                 190 ctt ttc aag cca tca gaa aaa tgg gat gtc ctc act agc act gta ctt     624
Leu Phe Lys Pro Ser Glu Lys Trp Asp Val Leu Thr Ser Thr Val Leu
        195                 200                 205 ttg att ggc atg gtt ggt tta ggc ttc ctc acc tac caa tgg ggt         672
Leu Ile Gly Met Val Gly Leu Leu Gly Phe Leu Thr Tyr Gln Trp Gly
210                 215                 220 tgg atg tgg ttg ctg aaa tat tat gca gtg ccc tac ctt gta ttc ata     720
Trp Met Trp Leu Leu Lys Tyr Tyr Ala Val Pro Tyr Leu Val Phe Ile
225                 230                 235                 240 gtt tgg cta gat ttg gtg aca ttc ttg cac cat act gag cca gaa ctt     768
Val Trp Leu Asp Leu Val Thr Phe Leu His His Thr Glu Pro Glu Leu
                245                 250                 255 cct tgg tat cgt gga gaa gat tgg act ttc ttg aaa ggt gca att tct     816
Pro Trp Tyr Arg Gly Glu Asp Trp Thr Phe Leu Lys Gly Ala Ile Ser
            260                 265                 270 agt att gac cgt gat tat ggt ttg gtt tat cat atc cat cac gat atc     864
Ser Ile Asp Arg Asp Tyr Gly Leu Val Tyr His Ile His His Asp Ile
        275                 280                 285 ggt act cat gtt gct cac cat ata ttc ctc aat atc cct cac tac aat     912
Gly Thr His Val Ala His His Ile Phe Leu Asn Ile Pro His Tyr Asn
290                 295                 300 ttg ctg aag gca act gag gca ata aaa cca gtg atg ggc gag tat ttc     960
Leu Leu Lys Ala Thr Glu Ala Ile Lys Pro Val Met Gly Glu Tyr Phe
305                 310                 315                 320
```

```
cat aaa tcg gaa gaa cca att tgg aag tca tta tgg aat tca tgt atc      1008
His Lys Ser Glu Glu Pro Ile Trp Lys Ser Leu Trp Asn Ser Cys Ile
            325                 330                 335 agt tgc cat ttt gta cct gat act ggt agt aag gtt tac tac aca tct      1056
Ser Cys His Phe Val Pro Asp Thr Gly Ser Lys Val Tyr Tyr Thr Ser
        340                 345                 350 aag aac aag tca gct aaa gcc taa                                      1080
Lys Asn Lys Ser Ala Lys Ala
            355
```

<210> SEQ ID NO 36
<211> LENGTH: 359
<212> TYPE: PRT
<213> ORGANISM: Nostoc sp

<400> SEQUENCE: 36

```
Val Gln Leu Asp Thr Ile Ser Phe Asn Asn Pro Leu Asn Ser Glu Thr
1               5                   10                  15

Ser Glu Asp Thr Thr Lys Leu Pro Phe Thr Leu Gly Asp Leu Lys Ala
            20                  25                  30

Ala Ile Pro Ala Glu Cys Phe Gln Pro Asn Val Thr Lys Ser Leu Phe
        35                  40                  45

Tyr Phe Phe Arg Asp Ile Leu Ile Gly Leu Leu Tyr Ala Val Ala
    50                  55                  60

Ser Tyr Leu Asp Ser Trp Leu Phe Phe Pro Ile Phe Trp Leu Met Gln
65                  70                  75                  80

Gly Thr Met Phe Trp Ala Leu Phe Val Val Gly His Asp Cys Gly His
                85                  90                  95

Gln Ser Phe Ser Lys Gln Lys Trp Leu Asn Asp Leu Ile Gly His Leu
            100                 105                 110

Ser His Thr Pro Ile Leu Val Pro Tyr His Gly Trp Arg Ile Ser His
        115                 120                 125

Arg Thr His His Lys Asn Thr Gly Asn Ile Asp Asn Asp Glu Ser Trp
    130                 135                 140

Tyr Pro Val Thr Glu Ser Gln Tyr Lys Asp Met Pro Leu Ala Gln Lys
145                 150                 155                 160

Ile Gly Arg Tyr Tyr Val Phe Leu Leu Ala Tyr Pro Val Tyr Leu Phe
                165                 170                 175

Lys Arg Ser Pro Asn Lys Glu Gly Ser His Phe Leu Pro Ser Ser Ser
            180                 185                 190

Leu Phe Lys Pro Ser Glu Lys Trp Asp Val Leu Thr Ser Thr Val Leu
        195                 200                 205

Leu Ile Gly Met Val Gly Leu Leu Gly Phe Leu Thr Tyr Gln Trp Gly
    210                 215                 220

Trp Met Trp Leu Leu Lys Tyr Tyr Ala Val Pro Tyr Leu Val Phe Ile
225                 230                 235                 240

Val Trp Leu Asp Leu Val Thr Phe Leu His His Thr Glu Pro Glu Leu
                245                 250                 255

Pro Trp Tyr Arg Gly Glu Asp Trp Thr Phe Leu Lys Gly Ala Ile Ser
            260                 265                 270

Ser Ile Asp Arg Asp Tyr Gly Leu Val Tyr His Ile His His Asp Ile
        275                 280                 285

Gly Thr His Val Ala His His Ile Phe Leu Asn Ile Pro His Tyr Asn
    290                 295                 300

Leu Leu Lys Ala Thr Glu Ala Ile Lys Pro Val Met Gly Glu Tyr Phe
```

```
                305                 310                 315                 320
His Lys Ser Glu Glu Pro Ile Trp Lys Ser Leu Trp Asn Ser Cys Ile
                    325                 330                 335

Ser Cys His Phe Val Pro Asp Thr Gly Ser Lys Val Tyr Tyr Thr Ser
                    340                 345                 350

Lys Asn Lys Ser Ala Lys Ala
                355

<210> SEQ ID NO 37
<211> LENGTH: 354
<212> TYPE: PRT
<213> ORGANISM: Artificial sequence
<220> FEATURE:
<223> OTHER INFORMATION: consensus sequence
<220> FEATURE:
<221> NAME/KEY: Variant
<222> LOCATION: (3)..(4)
<223> OTHER INFORMATION: Xaa in position 3 to 4 is any amino acid
<220> FEATURE:
<221> NAME/KEY: Variant
<222> LOCATION: (7)..(8)
<223> OTHER INFORMATION: Xaa in position 7 to 8 is any amino acid
<220> FEATURE:
<221> NAME/KEY: Variant
<222> LOCATION: (11)..(12)
<223> OTHER INFORMATION: Xaa in position 11 to 12 is any amino acid
<220> FEATURE:
<221> NAME/KEY: Variant
<222> LOCATION: (15)..(17)
<223> OTHER INFORMATION: Xaa in position 15 to 17 is any amino acid
<220> FEATURE:
<221> NAME/KEY: Variant
<222> LOCATION: (19)..(20)
<223> OTHER INFORMATION: Xaa in position 19 to 20 is any amino acid
<220> FEATURE:
<221> NAME/KEY: Variant
<222> LOCATION: (23)..(23)
<223> OTHER INFORMATION: Xaa in position 23 is any amino acid
<220> FEATURE:
<221> NAME/KEY: Variant
<222> LOCATION: (25)..(26)
<223> OTHER INFORMATION: Xaa in position 25 to 26 is any amino acid
<220> FEATURE:
<221> NAME/KEY: Variant
<222> LOCATION: (28)..(36)
<223> OTHER INFORMATION: Xaa in position 28 to 36 is any amino acid
<220> FEATURE:
<221> NAME/KEY: Variant
<222> LOCATION: (38)..(40)
<223> OTHER INFORMATION: Xaa in position 38 to 40 is any amino acid
<220> FEATURE:
<221> NAME/KEY: Variant
<222> LOCATION: (42)..(43)
<223> OTHER INFORMATION: Xaa in position 42 to 43 is any amino acid
<220> FEATURE:
<221> NAME/KEY: Variant
<222> LOCATION: (45)..(46)
<223> OTHER INFORMATION: Xaa in position 45 to 46 is any amino acid
<220> FEATURE:
<221> NAME/KEY: Variant
<222> LOCATION: (48)..(52)
<223> OTHER INFORMATION: Xaa in position 48 to 52 is any amino acid
<220> FEATURE:
<221> NAME/KEY: Variant
<222> LOCATION: (53)..(63)
<223> OTHER INFORMATION: Xaa in position 53 to 63 is any or no amino
      acid
<220> FEATURE:
<221> NAME/KEY: Variant
<222> LOCATION: (65)..(65)
<223> OTHER INFORMATION: Xaa in position 65 is any amino acid
<220> FEATURE:
<221> NAME/KEY: Variant
<222> LOCATION: (68)..(69)
<223> OTHER INFORMATION: Xaa in position 68 to 69 is any amino acid
```

```
<220> FEATURE:
<221> NAME/KEY: Variant
<222> LOCATION: (72)..(73)
<223> OTHER INFORMATION: Xaa in position 72 to 73 is any amino acid
<220> FEATURE:
<221> NAME/KEY: Variant
<222> LOCATION: (75)..(75)
<223> OTHER INFORMATION: Xaa in position 75 is any amino acid
<220> FEATURE:
<221> NAME/KEY: Variant
<222> LOCATION: (83)..(84)
<223> OTHER INFORMATION: Xaa in position 83 to 84 is any amino acid
<220> FEATURE:
<221> NAME/KEY: Variant
<222> LOCATION: (87)..(90)
<223> OTHER INFORMATION: Xaa in position 87 to 90 is any amino acid
<220> FEATURE:
<221> NAME/KEY: Variant
<222> LOCATION: (93)..(95)
<223> OTHER INFORMATION: Xaa in position 93 to 95 is any amino acid
<220> FEATURE:
<221> NAME/KEY: Variant
<222> LOCATION: (97)..(99)
<223> OTHER INFORMATION: Xaa in position 97 to 99 is any amino acid
<220> FEATURE:
<221> NAME/KEY: Variant
<222> LOCATION: (101)..(102)
<223> OTHER INFORMATION: Xaa in position 101 to 102 is any amino acid
<220> FEATURE:
<221> NAME/KEY: Variant
<222> LOCATION: (105)..(105)
<223> OTHER INFORMATION: Xaa in position 105 is any amino acid
<220> FEATURE:
<221> NAME/KEY: Variant
<222> LOCATION: (107)..(109)
<223> OTHER INFORMATION: Xaa in position 107 to 109 is any amino acid
<220> FEATURE:
<221> NAME/KEY: Variant
<222> LOCATION: (112)..(113)
<223> OTHER INFORMATION: Xaa in position 112 to 113 is any amino acid
<220> FEATURE:
<221> NAME/KEY: Variant
<222> LOCATION: (116)..(116)
<223> OTHER INFORMATION: Xaa in position 116 is any amino acid
<220> FEATURE:
<221> NAME/KEY: Variant
<222> LOCATION: (126)..(126)
<223> OTHER INFORMATION: Xaa in position 126 is any amino acid
<220> FEATURE:
<221> NAME/KEY: Variant
<222> LOCATION: (129)..(130)
<223> OTHER INFORMATION: Xaa in position 129 to 130 is any amino acid
<220> FEATURE:
<221> NAME/KEY: Variant
<222> LOCATION: (133)..(146)
<223> OTHER INFORMATION: Xaa in position 133 to 146 is any amino acid
<220> FEATURE:
<221> NAME/KEY: Variant
<222> LOCATION: (147)..(150)
<223> OTHER INFORMATION: Xaa in position 147 to 150 is any or no amino
      acid
<220> FEATURE:
<221> NAME/KEY: Variant
<222> LOCATION: (152)..(155)
<223> OTHER INFORMATION: Xaa in position 152 to 155 is any amino acid
<220> FEATURE:
<221> NAME/KEY: Variant
<222> LOCATION: (157)..(159)
<223> OTHER INFORMATION: Xaa in position 157 to 159 is any amino acid
<220> FEATURE:
<221> NAME/KEY: Variant
<222> LOCATION: (162)..(165)
<223> OTHER INFORMATION: Xaa in position 162 to 165 is any amino acid
<220> FEATURE:
<221> NAME/KEY: Variant
<222> LOCATION: (167)..(170)
<223> OTHER INFORMATION: Xaa in position 167 to 170 is any amino acid
<220> FEATURE:
<221> NAME/KEY: Variant
```

```
<222> LOCATION: (174)..(174)
<223> OTHER INFORMATION: Xaa in position 174 is any amino acid
<220> FEATURE:
<221> NAME/KEY: Variant
<222> LOCATION: (176)..(178)
<223> OTHER INFORMATION: Xaa in position 176 to 178 is any amino acid
<220> FEATURE:
<221> NAME/KEY: Variant
<222> LOCATION: (180)..(186)
<223> OTHER INFORMATION: Xaa in position 180 to 186 is any amino acid
<220> FEATURE:
<221> NAME/KEY: Variant
<222> LOCATION: (187)..(187)
<223> OTHER INFORMATION: Xaa in position 187 is any or no amino acid
<220> FEATURE:
<221> NAME/KEY: Variant
<222> LOCATION: (189)..(190)
<223> OTHER INFORMATION: Xaa in position 189 to 190 is any amino acid
<220> FEATURE:
<221> NAME/KEY: Variant
<222> LOCATION: (192)..(204)
<223> OTHER INFORMATION: Xaa in position 192 to 204 is any amino acid
<220> FEATURE:
<221> NAME/KEY: Variant
<222> LOCATION: (207)..(209)
<223> OTHER INFORMATION: Xaa in position 207 to 209 is any amino acid
<220> FEATURE:
<221> NAME/KEY: Variant
<222> LOCATION: (211)..(216)
<223> OTHER INFORMATION: Xaa in position 211 to 216 is any amino acid
<220> FEATURE:
<221> NAME/KEY: Variant
<222> LOCATION: (219)..(220)
<223> OTHER INFORMATION: Xaa in position 219 to 220 is any amino acid
<220> FEATURE:
<221> NAME/KEY: Variant
<222> LOCATION: (222)..(223)
<223> OTHER INFORMATION: Xaa in position 222 to 223 is any amino acid
<220> FEATURE:
<221> NAME/KEY: Variant
<222> LOCATION: (226)..(228)
<223> OTHER INFORMATION: Xaa in position 226 to 228 is any amino acid
<220> FEATURE:
<221> NAME/KEY: Variant
<222> LOCATION: (230)..(232)
<223> OTHER INFORMATION: Xaa in position 230 to 232 is any amino acid
<220> FEATURE:
<221> NAME/KEY: Variant
<222> LOCATION: (238)..(242)
<223> OTHER INFORMATION: Xaa in position 238 to 242 is any amino acid
<220> FEATURE:
<221> NAME/KEY: Variant
<222> LOCATION: (246)..(249)
<223> OTHER INFORMATION: Xaa in position 246 to 249 is any amino acid
<220> FEATURE:
<221> NAME/KEY: Variant
<222> LOCATION: (252)..(253)
<223> OTHER INFORMATION: Xaa in position 252 to 253 is any amino acid
<220> FEATURE:
<221> NAME/KEY: Variant
<222> LOCATION: (256)..(257)
<223> OTHER INFORMATION: Xaa in position 256 to 257 is any amino acid
<220> FEATURE:
<221> NAME/KEY: Variant
<222> LOCATION: (260)..(260)
<223> OTHER INFORMATION: Xaa in position 260 is any amino acid
<220> FEATURE:
<221> NAME/KEY: Variant
<222> LOCATION: (263)..(263)
<223> OTHER INFORMATION: Xaa in position 263 is any amino acid
<220> FEATURE:
<221> NAME/KEY: Variant
<222> LOCATION: (266)..(271)
<223> OTHER INFORMATION: Xaa in position 266 to 271 is any amino acid
<220> FEATURE:
<221> NAME/KEY: Variant
<222> LOCATION: (272)..(272)
<223> OTHER INFORMATION: Xaa in position 272 is any or no amino acid
<220> FEATURE:
```

```
<221> NAME/KEY: Variant
<222> LOCATION: (274)..(274)
<223> OTHER INFORMATION: Xaa in position 274 is any amino acid
<220> FEATURE:
<221> NAME/KEY: Variant
<222> LOCATION: (279)..(280)
<223> OTHER INFORMATION: Xaa in position 279 to 280 is any amino acid
<220> FEATURE:
<221> NAME/KEY: Variant
<222> LOCATION: (283)..(283)
<223> OTHER INFORMATION: Xaa in position 283 is any amino acid
<220> FEATURE:
<221> NAME/KEY: Variant
<222> LOCATION: (285)..(286)
<223> OTHER INFORMATION: Xaa in position 285 to 286 is any amino acid
<220> FEATURE:
<221> NAME/KEY: Variant
<222> LOCATION: (291)..(291)
<223> OTHER INFORMATION: Xaa in position 291 is any amino acid
<220> FEATURE:
<221> NAME/KEY: Variant
<222> LOCATION: (293)..(294)
<223> OTHER INFORMATION: Xaa in position 293 to 294 is any amino acid
<220> FEATURE:
<221> NAME/KEY: Variant
<222> LOCATION: (297)..(297)
<223> OTHER INFORMATION: Xaa in position 297 is any amino acid
<220> FEATURE:
<221> NAME/KEY: Variant
<222> LOCATION: (299)..(304)
<223> OTHER INFORMATION: Xaa in position 299 to 304 is any amino acid
<220> FEATURE:
<221> NAME/KEY: Variant
<222> LOCATION: (306)..(307)
<223> OTHER INFORMATION: Xaa in position 306 to 307 is any amino acid
<220> FEATURE:
<221> NAME/KEY: Variant
<222> LOCATION: (309)..(311)
<223> OTHER INFORMATION: Xaa in position 309 to 311 is any amino acid
<220> FEATURE:
<221> NAME/KEY: Variant
<222> LOCATION: (315)..(344)
<223> OTHER INFORMATION: Xaa in position 315 to 344 is any amino acid
<220> FEATURE:
<221> NAME/KEY: Variant
<222> LOCATION: (345)..(353)
<223> OTHER INFORMATION: Xaa in position 345 to 353 is any or no amino
      acid

<400> SEQUENCE: 37

Thr Leu Xaa Xaa Leu Lys Xaa Xaa Ile Pro Xaa Xaa Cys Phe Xaa Xaa
1               5                   10                  15

Xaa Val Xaa Xaa Ser Leu Xaa Tyr Xaa Xaa Arg Xaa Xaa Xaa Xaa Xaa
            20                  25                  30

Xaa Xaa Xaa Xaa Ala Xaa Xaa Xaa Tyr Xaa Xaa Ser Xaa Xaa Phe Xaa
        35                  40                  45

Xaa Xaa Xaa Xaa Xaa Xaa Xaa Xaa Xaa Xaa Xaa Xaa Xaa Xaa Xaa Leu
    50                  55                  60

Xaa Gln Gly Xaa Xaa Phe Trp Xaa Xaa Phe Xaa Val Gly His Asp Cys
65                  70                  75                  80

Gly His Xaa Xaa Phe Ser Xaa Xaa Xaa Leu Asn Xaa Xaa Xaa Gly
                85                  90                  95

Xaa Xaa Xaa His Xaa Xaa Ile Leu Xaa Pro Xaa Xaa Xaa Trp Arg Xaa
            100                 105                 110

Xaa His Arg Xaa His His Lys Asn Thr Gly Asn Ile Asp Xaa Asp Glu
            115                 120                 125

Xaa Xaa Tyr Pro Xaa Xaa Xaa Xaa Xaa Xaa Xaa Xaa Xaa Xaa Xaa Xaa
            130                 135                 140

Xaa Xaa Xaa Xaa Xaa Xaa Tyr Xaa Xaa Xaa Xaa Ala Xaa Xaa Xaa Tyr
```

```
                145                 150                 155                 160
Leu Xaa Xaa Xaa Xaa Pro Xaa Xaa Xaa Ser His Phe Xaa Pro Xaa
                165                 170                 175
Xaa Xaa Leu Xaa Xaa Xaa Xaa Xaa Xaa Xaa Val Xaa Xaa Ser Xaa
                180                 185                 190
Xaa Xaa Xaa Xaa Xaa Xaa Xaa Xaa Xaa Xaa Xaa Leu Thr Xaa Xaa
                195                 200                 205
Xaa Gly Xaa Xaa Xaa Xaa Xaa Tyr Tyr Xaa Xaa Pro Xaa Xaa Val
        210                 215                 220
Phe Xaa Xaa Xaa Leu Xaa Xaa Thr Phe Leu His His Xaa Xaa Xaa
225                 230                 235                 240
Xaa Xaa Pro Trp Tyr Xaa Xaa Xaa Xaa Trp Thr Xaa Xaa Lys Gly Xaa
                245                 250                 255
Xaa Ser Ser Xaa Asp Arg Xaa Tyr Gly Xaa Xaa Xaa Xaa Xaa Xaa
                260                 265                 270
His Xaa Ile Gly Thr His Xaa Xaa His His Xaa Phe Xaa Xaa Ile Pro
            275                 280                 285
His Tyr Xaa Leu Xaa Xaa Ala Thr Xaa Ala Xaa Xaa Xaa Xaa Xaa
        290                 295                 300
Glu Xaa Xaa Arg Xaa Xaa Xaa Glu Pro Ile Xaa Xaa Xaa Xaa Xaa
305                 310                 315                 320
Xaa Xaa Xaa Xaa Xaa Xaa Xaa Xaa Xaa Xaa Xaa Xaa Xaa Xaa Xaa
                325                 330                 335
Xaa Xaa Xaa Xaa Xaa Xaa Xaa Xaa Xaa Xaa Xaa Xaa Xaa Xaa Xaa
                340                 345                 350

Xaa Lys

<210> SEQ ID NO 38
<211> LENGTH: 60
<212> TYPE: PRT
<213> ORGANISM: Artificial sequence
<220> FEATURE:
<223> OTHER INFORMATION: sequence motif
<220> FEATURE:
<221> NAME/KEY: Variant
<222> LOCATION: (2)..(2)
<223> OTHER INFORMATION: Xaa in position 2 is Thr or Val
<220> FEATURE:
<221> NAME/KEY: Variant
<222> LOCATION: (10)..(10)
<223> OTHER INFORMATION: Xaa in position 10 is any or no amino acid
<220> FEATURE:
<221> NAME/KEY: Variant
<222> LOCATION: (12)..(12)
<223> OTHER INFORMATION: Xaa in position 12 is any or no amino acid
<220> FEATURE:
<221> NAME/KEY: Variant
<222> LOCATION: (15)..(15)
<223> OTHER INFORMATION: Xaa in position 15 is Lys or Arg
<220> FEATURE:
<221> NAME/KEY: Variant
<222> LOCATION: (16)..(16)
<223> OTHER INFORMATION: Xaa in position 16 is any amino acid
<220> FEATURE:
<221> NAME/KEY: Variant
<222> LOCATION: (17)..(17)
<223> OTHER INFORMATION: Xaa in position 17 is His or Lys
<220> FEATURE:
<221> NAME/KEY: Variant
<222> LOCATION: (18)..(18)
<223> OTHER INFORMATION: Xaa in position 18 is any amino acid
<220> FEATURE:
<221> NAME/KEY: Variant
<222> LOCATION: (19)..(19)
<223> OTHER INFORMATION: Xaa in position 19 is Leu or Val
```

```
<220> FEATURE:
<221> NAME/KEY: Variant
<222> LOCATION: (21)..(22)
<223> OTHER INFORMATION: Xaa in position 21 to 22 is any amino acid
<220> FEATURE:
<221> NAME/KEY: Variant
<222> LOCATION: (23)..(23)
<223> OTHER INFORMATION: Xaa in position 23 is Ile or Val
<220> FEATURE:
<221> NAME/KEY: Variant
<222> LOCATION: (25)..(25)
<223> OTHER INFORMATION: Xaa in position 25 is any amino acid
<220> FEATURE:
<221> NAME/KEY: Variant
<222> LOCATION: (26)..(26)
<223> OTHER INFORMATION: Xaa in position 26 is Ile or Leu
<220> FEATURE:
<221> NAME/KEY: Variant
<222> LOCATION: (27)..(27)
<223> OTHER INFORMATION: Xaa in position 27 is any amino acid
<220> FEATURE:
<221> NAME/KEY: Variant
<222> LOCATION: (29)..(29)
<223> OTHER INFORMATION: Xaa in position 29 is Ser or Thr
<220> FEATURE:
<221> NAME/KEY: Variant
<222> LOCATION: (30)..(30)
<223> OTHER INFORMATION: Xaa in position 30 is any amino acid
<220> FEATURE:
<221> NAME/KEY: Variant
<222> LOCATION: (33)..(33)
<223> OTHER INFORMATION: Xaa in position 33 is Thr or Val
<220> FEATURE:
<221> NAME/KEY: Variant
<222> LOCATION: (35)..(35)
<223> OTHER INFORMATION: Xaa in position 35 is Phe or Tyr
<220> FEATURE:
<221> NAME/KEY: Variant
<222> LOCATION: (36)..(36)
<223> OTHER INFORMATION: Xaa in position 36 is Glu or His
<220> FEATURE:
<221> NAME/KEY: Variant
<222> LOCATION: (37)..(37)
<223> OTHER INFORMATION: Xaa in position 37 is Gly or Ser
<220> FEATURE:
<221> NAME/KEY: Variant
<222> LOCATION: (40)..(40)
<223> OTHER INFORMATION: Xaa in position 40 is Ile or Val
<220> FEATURE:
<221> NAME/KEY: Variant
<222> LOCATION: (41)..(41)
<223> OTHER INFORMATION: Xaa in position 41 is Ser or Thr
<220> FEATURE:
<221> NAME/KEY: Variant
<222> LOCATION: (44)..(44)
<223> OTHER INFORMATION: Xaa in position 44 is any amino acid
<220> FEATURE:
<221> NAME/KEY: Variant
<222> LOCATION: (47)..(47)
<223> OTHER INFORMATION: Xaa in position 47 is any amino acid
<220> FEATURE:
<221> NAME/KEY: Variant
<222> LOCATION: (54)..(54)
<223> OTHER INFORMATION: Xaa in position 54 is any amino acid
<220> FEATURE:
<221> NAME/KEY: Variant
<222> LOCATION: (57)..(57)
<223> OTHER INFORMATION: Xaa in position 57 is any amino acid
<220> FEATURE:
<221> NAME/KEY: Variant
<222> LOCATION: (58)..(58)
<223> OTHER INFORMATION: Xaa in position 58 is Phe or Trp

<400> SEQUENCE: 38

Phe Xaa Val Gly His Asp Cys Gly His Xaa Ser Xaa Phe Ser Xaa Xaa
1               5                   10                  15

Xaa Xaa Xaa Asn Xaa Xaa Xaa Gly Xaa Xaa Xaa His Xaa Xaa Ile Leu
```

```
                    20                  25                  30
Xaa Pro Xaa Xaa Xaa Trp Arg Xaa Xaa His Arg Xaa His His Xaa Asn
            35                  40                  45

Thr Gly Asn Ile Asp Xaa Asp Glu Xaa Xaa Tyr Pro
        50                  55                  60

<210> SEQ ID NO 39
<211> LENGTH: 38
<212> TYPE: PRT
<213> ORGANISM: Artificial sequence
<220> FEATURE:
<223> OTHER INFORMATION: sequence motif
<220> FEATURE:
<221> NAME/KEY: Variant
<222> LOCATION: (2)..(2)
<223> OTHER INFORMATION: Xaa in position 2 is any or no amino acid
<220> FEATURE:
<221> NAME/KEY: Variant
<222> LOCATION: (4)..(4)
<223> OTHER INFORMATION: Xaa in position 4 is any or no amino acid
<220> FEATURE:
<221> NAME/KEY: Variant
<222> LOCATION: (6)..(6)
<223> OTHER INFORMATION: Xaa in position 6 is any or no amino acid
<220> FEATURE:
<221> NAME/KEY: Variant
<222> LOCATION: (11)..(11)
<223> OTHER INFORMATION: Xaa in position 11 is Asn or Thr
<220> FEATURE:
<221> NAME/KEY: Variant
<222> LOCATION: (12)..(12)
<223> OTHER INFORMATION: Xaa in position 12 is Asp or Glu
<220> FEATURE:
<221> NAME/KEY: Variant
<222> LOCATION: (13)..(13)
<223> OTHER INFORMATION: Xaa in position 13 is any amino acid
<220> FEATURE:
<221> NAME/KEY: Variant
<222> LOCATION: (14)..(14)
<223> OTHER INFORMATION: Xaa in position 14 is Ala, Asp or Glu
<220> FEATURE:
<221> NAME/KEY: Variant
<222> LOCATION: (15)..(15)
<223> OTHER INFORMATION: Xaa in position 15 is any amino acid
<220> FEATURE:
<221> NAME/KEY: Variant
<222> LOCATION: (19)..(19)
<223> OTHER INFORMATION: Xaa in position 19 is any amino acid
<220> FEATURE:
<221> NAME/KEY: Variant
<222> LOCATION: (20)..(20)
<223> OTHER INFORMATION: Xaa in position 20 is Asp or Gly
<220> FEATURE:
<221> NAME/KEY: Variant
<222> LOCATION: (21)..(21)
<223> OTHER INFORMATION: Xaa in position 21 is Glu or Ser
<220> FEATURE:
<221> NAME/KEY: Variant
<222> LOCATION: (22)..(22)
<223> OTHER INFORMATION: Xaa in position 22 is Asp or Glu
<220> FEATURE:
<221> NAME/KEY: Variant
<222> LOCATION: (25)..(25)
<223> OTHER INFORMATION: Xaa in position 25 is Phe or Tyr
<220> FEATURE:
<221> NAME/KEY: Variant
<222> LOCATION: (26)..(26)
<223> OTHER INFORMATION: Xaa in position 26 is Leu or Val
<220> FEATURE:
<221> NAME/KEY: Variant
<222> LOCATION: (29)..(29)
<223> OTHER INFORMATION: Xaa in position 29 is Ala or Asn
<220> FEATURE:
<221> NAME/KEY: Variant
<222> LOCATION: (30)..(30)
<223> OTHER INFORMATION: Xaa in position 30 is Ile or Leu
```

```
<220> FEATURE:
<221> NAME/KEY: Variant
<222> LOCATION: (33)..(33)
<223> OTHER INFORMATION: Xaa in position 33 is Ile or Val
<220> FEATURE:
<221> NAME/KEY: Variant
<222> LOCATION: (36)..(36)
<223> OTHER INFORMATION: Xaa in position 36 is Asp, Asn or Ser

<400> SEQUENCE: 39

Leu Xaa Val Xaa Thr Xaa Phe Leu His His Xaa Xaa Xaa Xaa Pro
1               5                   10                  15

Trp Tyr Xaa Xaa Xaa Xaa Trp Thr Xaa Xaa Lys Gly Xaa Xaa Ser Ser
            20                  25                  30

Xaa Asp Arg Xaa Tyr Gly
        35

<210> SEQ ID NO 40
<211> LENGTH: 28
<212> TYPE: PRT
<213> ORGANISM: Artificial sequence
<220> FEATURE:
<223> OTHER INFORMATION: sequence motif
<220> FEATURE:
<221> NAME/KEY: Variant
<222> LOCATION: (3)..(3)
<223> OTHER INFORMATION: Xaa in position 3 is any or no amino acid
<220> FEATURE:
<221> NAME/KEY: Variant
<222> LOCATION: (8)..(8)
<223> OTHER INFORMATION: Xaa in position 8 is any amino acid
<220> FEATURE:
<221> NAME/KEY: Variant
<222> LOCATION: (9)..(9)
<223> OTHER INFORMATION: Xaa in position 9 is Ala or Val
<220> FEATURE:
<221> NAME/KEY: Variant
<222> LOCATION: (12)..(12)
<223> OTHER INFORMATION: Xaa in position 12 is Ile or Leu
<220> FEATURE:
<221> NAME/KEY: Variant
<222> LOCATION: (14)..(15)
<223> OTHER INFORMATION: Xaa in position 14 to 15 is any amino acid
<220> FEATURE:
<221> NAME/KEY: Variant
<222> LOCATION: (16)..(16)
<223> OTHER INFORMATION: Xaa in position 16 is Ile or Met
<220> FEATURE:
<221> NAME/KEY: Variant
<222> LOCATION: (20)..(20)
<223> OTHER INFORMATION: Xaa in position 20 is any amino acid
<220> FEATURE:
<221> NAME/KEY: Variant
<222> LOCATION: (22)..(22)
<223> OTHER INFORMATION: Xaa in position 22 is any amino acid
<220> FEATURE:
<221> NAME/KEY: Variant
<222> LOCATION: (23)..(23)
<223> OTHER INFORMATION: Xaa in position 23 is Glu, Lys or Arg
<220> FEATURE:
<221> NAME/KEY: Variant
<222> LOCATION: (26)..(26)
<223> OTHER INFORMATION: Xaa in position 26 is Glu or Lys
<220> FEATURE:
<221> NAME/KEY: Variant
<222> LOCATION: (27)..(27)
<223> OTHER INFORMATION: Xaa in position 27 is any amino acid
<220> FEATURE:
<221> NAME/KEY: Variant
<222> LOCATION: (28)..(28)
<223> OTHER INFORMATION: Xaa in position 28 is Phe or Ile

<400> SEQUENCE: 40

His His Xaa Ile Gly Thr His Xaa Xaa His His Xaa Phe Xaa Xaa Xaa
```

```
 1               5                  10                 15
Pro His Tyr Xaa Leu Xaa Xaa Ala Thr Xaa Xaa Xaa
             20                 25
```

<210> SEQ ID NO 41
<211> LENGTH: 32
<212> TYPE: PRT
<213> ORGANISM: Artificial sequence
<220> FEATURE:
<223> OTHER INFORMATION: sequence motif
<220> FEATURE:
<221> NAME/KEY: Variant
<222> LOCATION: (2)..(4)
<223> OTHER INFORMATION: Xaa in position 2 to 4 is any amino acid
<220> FEATURE:
<221> NAME/KEY: Variant
<222> LOCATION: (6)..(6)
<223> OTHER INFORMATION: Xaa in position 6 is any amino acid
<220> FEATURE:
<221> NAME/KEY: Variant
<222> LOCATION: (7)..(7)
<223> OTHER INFORMATION: Xaa in position 7 is Ala or Ser
<220> FEATURE:
<221> NAME/KEY: Variant
<222> LOCATION: (8)..(8)
<223> OTHER INFORMATION: Xaa in position 8 is Ile or Leu
<220> FEATURE:
<221> NAME/KEY: Variant
<222> LOCATION: (10)..(10)
<223> OTHER INFORMATION: Xaa in position 10 is any amino acid
<220> FEATURE:
<221> NAME/KEY: Variant
<222> LOCATION: (11)..(11)
<223> OTHER INFORMATION: Xaa in position 11 is Ala, Asp or Glu
<220> FEATURE:
<221> NAME/KEY: Variant
<222> LOCATION: (14)..(14)
<223> OTHER INFORMATION: Xaa in position 14 is Glu or Gln
<220> FEATURE:
<221> NAME/KEY: Variant
<222> LOCATION: (15)..(15)
<223> OTHER INFORMATION: Xaa in position 15 is Ala, Pro or Ser
<220> FEATURE:
<221> NAME/KEY: Variant
<222> LOCATION: (16)..(16)
<223> OTHER INFORMATION: Xaa in position 16 is Asn or Ser
<220> FEATURE:
<221> NAME/KEY: Variant
<222> LOCATION: (17)..(17)
<223> OTHER INFORMATION: Xaa in position 17 is Leu or Val
<220> FEATURE:
<221> NAME/KEY: Variant
<222> LOCATION: (18)..(19)
<223> OTHER INFORMATION: Xaa in position 18 to 19 is any amino acid
<220> FEATURE:
<221> NAME/KEY: Variant
<222> LOCATION: (22)..(22)
<223> OTHER INFORMATION: Xaa in position 22 is Phe or Tyr
<220> FEATURE:
<221> NAME/KEY: Variant
<222> LOCATION: (24)..(25)
<223> OTHER INFORMATION: Xaa in position 24 to 25 is any amino acid
<220> FEATURE:
<221> NAME/KEY: Variant
<222> LOCATION: (27)..(27)
<223> OTHER INFORMATION: Xaa in position 27 is Ala, Cys, Asp or Ser
<220> FEATURE:
<221> NAME/KEY: Variant
<222> LOCATION: (28)..(28)
<223> OTHER INFORMATION: Xaa in position 28 is Ile, Leu or Val
<220> FEATURE:
<221> NAME/KEY: Variant
<222> LOCATION: (29)..(30)
<223> OTHER INFORMATION: Xaa in position 29 to 30 is any amino acid
<220> FEATURE:
<221> NAME/KEY: Variant
<222> LOCATION: (31)..(31)

```
<223> OTHER INFORMATION: Xaa in position 31 is Ala, Ile or Val
<220> FEATURE:
<221> NAME/KEY: Variant
<222> LOCATION: (32)..(32)
<223> OTHER INFORMATION: Xaa in position 32 is Gly, Ser or Val

<400> SEQUENCE: 41

Leu Xaa Xaa Xaa Lys Xaa Xaa Xaa Pro Xaa Xaa Cys Phe Xaa Xaa Xaa
1               5                   10                  15

Xaa Xaa Xaa Ser Leu Xaa Tyr Xaa Xaa Arg Xaa Xaa Xaa Xaa Xaa Xaa
            20                  25                  30

<210> SEQ ID NO 42
<211> LENGTH: 35
<212> TYPE: PRT
<213> ORGANISM: Artificial sequence
<220> FEATURE:
<223> OTHER INFORMATION: sequence motif
<220> FEATURE:
<221> NAME/KEY: Variant
<222> LOCATION: (3)..(5)
<223> OTHER INFORMATION: Xaa in position 3 to 5 is any or no amino acid
<220> FEATURE:
<221> NAME/KEY: Variant
<222> LOCATION: (7)..(7)
<223> OTHER INFORMATION: Xaa in position 7 is Phe or Val
<220> FEATURE:
<221> NAME/KEY: Variant
<222> LOCATION: (8)..(10)
<223> OTHER INFORMATION: Xaa in position 8 to 10 is any amino acid
<220> FEATURE:
<221> NAME/KEY: Variant
<222> LOCATION: (12)..(12)
<223> OTHER INFORMATION: Xaa in position 12 is Asn or Pro
<220> FEATURE:
<221> NAME/KEY: Variant
<222> LOCATION: (13)..(13)
<223> OTHER INFORMATION: Xaa in position 13 is Lys or Arg
<220> FEATURE:
<221> NAME/KEY: Variant
<222> LOCATION: (14)..(15)
<223> OTHER INFORMATION: Xaa in position 14 to 15 is any amino acid
<220> FEATURE:
<221> NAME/KEY: Variant
<222> LOCATION: (16)..(16)
<223> OTHER INFORMATION: Xaa in position 16 is Asn or Ser
<220> FEATURE:
<221> NAME/KEY: Variant
<222> LOCATION: (19)..(19)
<223> OTHER INFORMATION: Xaa in position 19 is any amino acid
<220> FEATURE:
<221> NAME/KEY: Variant
<222> LOCATION: (21)..(21)
<223> OTHER INFORMATION: Xaa in position 21 is any amino acid
<220> FEATURE:
<221> NAME/KEY: Variant
<222> LOCATION: (22)..(22)
<223> OTHER INFORMATION: Xaa in position 22 is Glu or Ser
<220> FEATURE:
<221> NAME/KEY: Variant
<222> LOCATION: (23)..(23)
<223> OTHER INFORMATION: Xaa in position 23 is Ala, Pro or Ser
<220> FEATURE:
<221> NAME/KEY: Variant
<222> LOCATION: (24)..(24)
<223> OTHER INFORMATION: Xaa in position 24 is Leu or Met
<220> FEATURE:
<221> NAME/KEY: Variant
<222> LOCATION: (25)..(25)
<223> OTHER INFORMATION: Xaa in position 25 is Phe or Tyr
<220> FEATURE:
<221> NAME/KEY: Variant
<222> LOCATION: (26)..(31)
<223> OTHER INFORMATION: Xaa in position 26 to 31 is any amino acid
<220> FEATURE:
<221> NAME/KEY: Variant
```

```
<222> LOCATION: (32)..(32)
<223> OTHER INFORMATION: Xaa in position 32 is Ala, Asp or Val
<220> FEATURE:
<221> NAME/KEY: Variant
<222> LOCATION: (33)..(33)
<223> OTHER INFORMATION: Xaa in position 33 is Ile or Val
<220> FEATURE:
<221> NAME/KEY: Variant
<222> LOCATION: (34)..(34)
<223> OTHER INFORMATION: Xaa in position 34 is Ile or Leu
<220> FEATURE:
<221> NAME/KEY: Variant
<222> LOCATION: (35)..(35)
<223> OTHER INFORMATION: Xaa in position 35 is Ser or Thr

<400> SEQUENCE: 42

Ala Tyr Xaa Xaa Xaa Leu Xaa Xaa Xaa Pro Xaa Xaa Xaa Xaa Xaa
1               5                   10                  15

His Phe Xaa Pro Xaa Xaa Xaa Xaa Xaa Xaa Xaa Xaa Xaa Xaa Xaa
            20                  25                  30

Xaa Xaa Xaa
        35

<210> SEQ ID NO 43
<211> LENGTH: 13
<212> TYPE: PRT
<213> ORGANISM: Artificial sequence
<220> FEATURE:
<223> OTHER INFORMATION: sequence motif
<220> FEATURE:
<221> NAME/KEY: Variant
<222> LOCATION: (2)..(2)
<223> OTHER INFORMATION: Xaa in position 2 is any amino acid
<220> FEATURE:
<221> NAME/KEY: Variant
<222> LOCATION: (3)..(3)
<223> OTHER INFORMATION: Xaa in position 3 is Asn or Ser
<220> FEATURE:
<221> NAME/KEY: Variant
<222> LOCATION: (4)..(4)
<223> OTHER INFORMATION: Xaa in position 4 is Ala, Asp or Glu
<220> FEATURE:
<221> NAME/KEY: Variant
<222> LOCATION: (5)..(5)
<223> OTHER INFORMATION: Xaa in position 5 is Ala or Glu
<220> FEATURE:
<221> NAME/KEY: Variant
<222> LOCATION: (8)..(9)
<223> OTHER INFORMATION: Xaa in position 8 to 9 is any amino acid
<220> FEATURE:
<221> NAME/KEY: Variant
<222> LOCATION: (10)..(10)
<223> OTHER INFORMATION: Xaa in position 10 is Ala, Ser or Thr
<220> FEATURE:
<221> NAME/KEY: Variant
<222> LOCATION: (11)..(11)
<223> OTHER INFORMATION: Xaa in position 11 is Phe or Leu
<220> FEATURE:
<221> NAME/KEY: Variant
<222> LOCATION: (12)..(12)
<223> OTHER INFORMATION: Xaa in position 12 is Phe or Trp
<220> FEATURE:
<221> NAME/KEY: Variant
<222> LOCATION: (13)..(13)
<223> OTHER INFORMATION: Xaa in position 13 is Lys or Arg

<400> SEQUENCE: 43

Arg Xaa Xaa Xaa Xaa Pro Ile Xaa Xaa Xaa Xaa Xaa Xaa
1               5                   10

<210> SEQ ID NO 44
<211> LENGTH: 26
<212> TYPE: PRT
```

```
<213> ORGANISM: Artificial sequence
<220> FEATURE:
<223> OTHER INFORMATION: sequence motif
<220> FEATURE:
<221> NAME/KEY: Variant
<222> LOCATION: (2)..(2)
<223> OTHER INFORMATION: Xaa in position 2 is any amino acid
<220> FEATURE:
<221> NAME/KEY: Variant
<222> LOCATION: (3)..(7)
<223> OTHER INFORMATION: Xaa in position 3 to 7 is any or no amino acid
<220> FEATURE:
<221> NAME/KEY: Variant
<222> LOCATION: (9)..(9)
<223> OTHER INFORMATION: Xaa in position 9 is Trp or Tyr
<220> FEATURE:
<221> NAME/KEY: Variant
<222> LOCATION: (10)..(10)
<223> OTHER INFORMATION: Xaa in position 10 is Gln or Ser
<220> FEATURE:
<221> NAME/KEY: Variant
<222> LOCATION: (11)..(11)
<223> OTHER INFORMATION: Xaa in position 11 is any amino acid
<220> FEATURE:
<221> NAME/KEY: Variant
<222> LOCATION: (13)..(13)
<223> OTHER INFORMATION: Xaa in position 13 is Phe or Trp
<220> FEATURE:
<221> NAME/KEY: Variant
<222> LOCATION: (14)..(15)
<223> OTHER INFORMATION: Xaa in position 14 to 15 is any amino acid
<220> FEATURE:
<221> NAME/KEY: Variant
<222> LOCATION: (16)..(16)
<223> OTHER INFORMATION: Xaa in position 16 is Leu or Met
<220> FEATURE:
<221> NAME/KEY: Variant
<222> LOCATION: (17)..(17)
<223> OTHER INFORMATION: Xaa in position 17 is Gly or Leu
<220> FEATURE:
<221> NAME/KEY: Variant
<222> LOCATION: (18)..(18)
<223> OTHER INFORMATION: Xaa in position 18 is any amino acid
<220> FEATURE:
<221> NAME/KEY: Variant
<222> LOCATION: (19)..(19)
<223> OTHER INFORMATION: Xaa in position 19 is Phe or Tyr
<220> FEATURE:
<221> NAME/KEY: Variant
<222> LOCATION: (21)..(21)
<223> OTHER INFORMATION: Xaa in position 21 is any amino acid
<220> FEATURE:
<221> NAME/KEY: Variant
<222> LOCATION: (22)..(22)
<223> OTHER INFORMATION: Xaa in position 22 is Ala or Val
<220> FEATURE:
<221> NAME/KEY: Variant
<222> LOCATION: (24)..(24)
<223> OTHER INFORMATION: Xaa in position 24 is any amino acid
<220> FEATURE:
<221> NAME/KEY: Variant
<222> LOCATION: (25)..(25)
<223> OTHER INFORMATION: Xaa in position 25 is Phe, Ile or Leu

<400> SEQUENCE: 44

Phe Xaa Xaa Xaa Xaa Xaa Xaa Thr Xaa Xaa Xaa Gly Xaa Xaa Xaa Xaa
1               5                   10                  15

Xaa Xaa Xaa Tyr Xaa Xaa Pro Xaa Xaa Val
            20                  25

<210> SEQ ID NO 45
<211> LENGTH: 10
<212> TYPE: PRT
<213> ORGANISM: Artificial sequence
<220> FEATURE:
<223> OTHER INFORMATION: sequence motif
```

```
<220> FEATURE:
<221> NAME/KEY: Variant
<222> LOCATION: (2)..(2)
<223> OTHER INFORMATION: Xaa in position 2 is Ile, Leu or Met
<220> FEATURE:
<221> NAME/KEY: Variant
<222> LOCATION: (5)..(5)
<223> OTHER INFORMATION: Xaa in position 5 is any amino acid
<220> FEATURE:
<221> NAME/KEY: Variant
<222> LOCATION: (6)..(6)
<223> OTHER INFORMATION: Xaa in position 6 is Leu, Met or Val
<220> FEATURE:
<221> NAME/KEY: Variant
<222> LOCATION: (9)..(9)
<223> OTHER INFORMATION: Xaa in position 9 is Ala, Gly or Ser
<220> FEATURE:
<221> NAME/KEY: Variant
<222> LOCATION: (10)..(10)
<223> OTHER INFORMATION: Xaa in position 10 is Phe or Leu

<400> SEQUENCE: 45

Leu Xaa Gln Gly Xaa Xaa Phe Trp Xaa Xaa
1               5                   10

<210> SEQ ID NO 46
<211> LENGTH: 20
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (3)..(3)
<223> OTHER INFORMATION: y is c or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: y is c or t
<220> FEATURE:
<221> NAME/KEY: misc_feature
<222> LOCATION: (15)..(15)
<223> OTHER INFORMATION: y is c or t
<220> FEATURE:
<221> NAME/KEY: misc_feature
<222> LOCATION: (18)..(18)
<223> OTHER INFORMATION: n is a, c, g, or t

<400> SEQUENCE: 46
ttytggggnt tyttyacngt                                              20

<210> SEQ ID NO 47
<211> LENGTH: 19
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 47
ccyttnacyt angtccact                                               19
```

```
<210> SEQ ID NO 48
<211> LENGTH: 26
<212> TYPE: DNA
<213> ORGANISM: Artificial sequence
<220> FEATURE:
<223> OTHER INFORMATION: primer

<400> SEQUENCE: 48
tcgcgctcgc atgtgctcaa cttcag                                          26

<210> SEQ ID NO 49
<211> LENGTH: 26
<212> TYPE: DNA
<213> ORGANISM: Artificial sequence
<220> FEATURE:
<223> OTHER INFORMATION: primer

<400> SEQUENCE: 49
tggtgaccac gagcatcgtg gcgaag                                          26

<210> SEQ ID NO 50
<211> LENGTH: 26
<212> TYPE: DNA
<213> ORGANISM: Artificial sequence
<220> FEATURE:
<223> OTHER INFORMATION: primer

<400> SEQUENCE: 50
tcctcacgcc gttcgagtcc tggaag                                          26

<210> SEQ ID NO 51
<211> LENGTH: 27
<212> TYPE: DNA
<213> ORGANISM: Artificial sequence
<220> FEATURE:
<223> OTHER INFORMATION: primer

<400> SEQUENCE: 51
atggtcgtga agcccaagac gaaggtc                                         27

<210> SEQ ID NO 52
<211> LENGTH: 21
<212> TYPE: DNA
<213> ORGANISM: Artificial sequence
<220> FEATURE:
<223> OTHER INFORMATION: primer

<400> SEQUENCE: 52
tccgctcgcc atggcgtcca c                                               21

<210> SEQ ID NO 53
<211> LENGTH: 25
<212> TYPE: DNA
<213> ORGANISM: Artificial sequence
<220> FEATURE:
<223> OTHER INFORMATION: primer

<400> SEQUENCE: 53
tgaccgatca cttagctgca gctta                                           25
```

ISOLATION AND CHARACTERIZATION OF A NOVEL PYTHIUM OMEGA 3 DESATURASE WITH SPECIFICITY TO ALL OMEGA 6 FATTY ACIDS LONGER THAN 18 CARBON CHAINS

RELATED APPLICATIONS

This application is a divisional of patent application Ser. No. 12/438,373 filed on Feb. 23, 2009, which is a national stage application (under 35 U.S.C. § 371) of PCT/EP2007/058528 filed Aug. 16, 2007, which claims benefit of European application 06119502.0 filed Aug. 24, 2006. The entire content of each aforementioned application is hereby incorporated by reference in its entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_074040_0028_01. The size of the text file is 162 KB, and the text file was created on Apr. 13, 2015.

The present invention relates to a polynucleotide encoding an omega 3 (ω-3) desaturase from *Pythium irregulare* with specificity to long chain polyunsaturated omega 6 (ω-6) fatty acids as well as a vector containing said polynucleotide, and a host cell containing the vector or the polynucleotide. Moreover, the present invention pertains to a polypeptide encoded by the said polynucleotide, antibodies against the polypeptide as well as a method for the manufacture of the polypeptide. Further, encompassed by the present invention are transgenic non-human organisms. Finally, the present invention relates to methods for the manufacture of compounds and oil-fatty acid- or lipid-containing compositions.

Fatty acids and triacylglycerides have a multiplicity of applications in the food industry, in animal nutrition, in cosmetics and the pharmacological sector. Depending on whether they are free saturated or unsaturated fatty acids or else triacylglycerides with an elevated content of saturated or unsaturated fatty acids, they are suitable for various different applications.

Polyunsaturated long-chain ω-3-fatty acids such as eicosapentaenoic acid (=EPA, $C0:5^{\Delta 5,8,11,14,17}$), ω-3 eicostetraenic acid (=ETA, $C20:4^{\Delta 8,11,14,17}$) or docosahexaenoic acid (=DHA, $C22:6^{\Delta 4,7,10,13,16,19}$) are important components of human nutrition owing to their various roles in health aspects, including the development of the child brain, the functionality of the eyes, the synthesis of hormones and other signal substances, and the prevention of cardiovascular disorders, cancer and diabetes (Poulos, A Lipids 30:1-14, 1995; Horrocks, L A and Yeo Y K Pharmacol Res 40:211-225, 1999). There is, therefore, a need for the production of polyunsaturated long-chain fatty acids.

Owing to the present-day composition of human food, an addition of polyunsaturated ω-3-fatty acids, which are preferentially found in fish oils, to the food is particularly important. Thus, for example, polyunsaturated fatty acids such as DHA or EPA are added to infant formula to improve the nutritional value. The unsaturated fatty acid DHA is supposed to have a positive effect on the development and maintenance of brain functions.

In the following, polyunsaturated fatty acids are sometimes referred to as PUFA, PUFAs, LCPUFA or LCPUFAs (poly unsaturated fatty acids, PUFA long chain poly unsaturated fatty acids, LCPUFA).

The various fatty acids and triglycerides are mainly obtained from microorganisms such as *Mortierella* or *Schizochytrium* or from oil-producing plants such as soybeans, oilseed rape, algae such as *Crypthecodinium* or *Phaeodactylum* and others, being obtained, as a rule, in the form of their triacylglycerides (=triglycerides=triglycerols). However, they can also be obtained from animals, for example, fish. The free fatty acids are, advantageously, prepared by hydrolysis. Very long-chain polyunsaturated fatty acids such as DHA, EPA, arachidonic acid (=ARA, $C20:4^{\Delta 5,8,11,14}$), dihomo-γ-linolenic acid (=DGLA, $C20:3^{\Delta 8,11,14}$) or docosapentaenoic acid (DPA, $C22:5^{\Delta 47,10,13,16,19}$) are not synthesized in plants, for example in oil crops such as oilseed rape, soybeans, sunflowers and safflower. Conventional natural sources of these fatty acids are fish such as herring, salmon, sardine, redfish, eel, carp, trout, halibut, mackerel, zander or tuna, or algae. Depending on the intended use, oils with saturated or unsaturated fatty acids are preferred. In human nutrition, for example, lipids with unsaturated fatty acids, specifically polyunsaturated fatty acids, are preferred. The polyunsaturated ω-3-fatty acids are said to have a positive effect on the cholesterol level in the blood and thus on the possibility of preventing heart disease. The risk of heart disease, stroke or hypertension can be reduced markedly by adding these ω-3-fatty acids to the food. Also, ω-3-fatty acids have a positive effect on inflammatory, specifically on chronically inflammatory, processes in association with immunological diseases such as rheumatoid arthritis. They are, therefore, added to foodstuffs, specifically to dietetic foodstuffs, or are employed in medicaments. ω-6-fatty acids such as arachidonic acid tend to have an adverse effect on these disorders in connection with these rheumatic diseases on account of our usual dietary intake.

ω-3- and ω-6-fatty acids are precursors of tissue hormones, known as eicosanoids, such as the prostaglandins. The prostaglandins which are derived from dihomo-γ-linolenic acid, arachidonic acid and eicosapentaenoic acid, and of the thromoxanes and leukotrienes, which are derived from arachidonic acid and eicosapentaenoic acid. Eicosanoids (known as the $PG_2$ series) which are formed from the ω-6-fatty acids generally promote inflammatory reactions, while eicosanoids (known as the $PG_3$ series) from ω-3-fatty acids have little or no proinflammatory effect. Therefore, food having a high proportion of ω-3-fatty acid has a positive effect on human health.

Owing to their positive characteristics, there has been no lack of attempts in the past to make available genes which are involved in the synthesis of fatty acids or triglycerides for the production of oils in various organisms with a modified content of unsaturated fatty acids. Thus, WO 91/13972 and its US equivalent describe a Δ9-desaturase. WO 93/11245 claims Δ15-desaturase and WO 94/11516 a Δ12-desaturase. Further desaturases are described, for example, in EP A 0 550 162, WO 94/18337, WO 97/30582, WO 97/21340, WO 95/18222, EP A 0 794 250, Stukey et al., J. Biol. Chem., 265, 1990: 20144-20149, Wada et al., Nature 347, 1990: 200-203 or Huang et al., Lipids 34, 1999: 649-659. However, the biochemical characterization of the various desaturases has been insufficient to date since the enzymes, being membrane-bound proteins, present great difficulty in their isolation and characterization (McKeon et al., Methods in Enzymol. 71, 1981: 12141-12147, Wang et al., Plant Physiol. Biochem., 26, 1988: 777-792). As a rule, membrane-bound desaturases are characterized by being introduced into a suitable organism which is subsequently analyzed for enzyme activity by analyzing the starting materials and the products. Δ6-Desaturases are described in WO 93/06712, U.S. Pat. No. 5,614,393, U.S. Pat. No. 5,614,393, WO 96/21022, WO 00/21557 and WO 99/27111, and also the application for the production in transgenic organisms is described in WO 98/46763, WO 98/46764 and WO 98/46765. Here, the expression of various desaturases is also described and claimed in WO 99/64616 or WO 98/46776, as is the formation of polyunsaturated fatty acids. As regards the expression efficacy of desaturases and its effect on the formation of polyunsaturated fatty acids, it must be noted that the expression of a single desaturase as described to date has only resulted in low contents of unsaturated fatty acids/lipids such as, for example, γ-linolenic acid and stearidonic acid. Furthermore, mixtures of ω-3- and ω-6-fatty acids are usually obtained.

Especially suitable microorganisms for the production of PUFAs are microorganisms including microalgae such as *Phaeodactylum tricornutum, Porphiridium* species, *Thraustochytrium* species, *Schizochytrium* species or *Cryptheco-dinium* species, ciliates such as *Stylonychia* or *Colpidium*, fungi such as *Mortierella, Entomophthora* or *Mucor* and/or mosses such as *Physcomitrella, Ceratodon* and *Marchantia* (R. Vazhappilly & F. Chen (1998) Botanica Marina 41: 553-558; K. Totani & K. Oba (1987) Lipids 22: 1060-1062; M. Akimoto et al. (1998) Appl. Biochemistry and Biotechnology 73: 269-278). Strain selection has resulted in the development of a number of mutant strains of the microorganisms in question which produce a series of desirable compounds including PUFAs. However, the mutation and selection of strains with an improved production of a particular molecule such as the polyunsaturated fatty acids is a time-consuming and difficult process. Thus, recombinant methods are preferred wherever possible. However, only limited amounts of the desired polyunsaturated fatty acids such as ETA, DHA or EPA can be produced with the aid of the abovementioned microorganisms; where they are generally obtained as fatty acid mixtures of, for example, ETA, EPA and DHA, depending on the microorganism used.

A variety of synthetic pathways is being discussed for the synthesis of the polyunsaturated fatty acids, eicosapentaenoic acid and docosahexaenoic acid. EPA or DHA are produced in numerous marine bacteria such as *Vibrio* sp. or *Shewanella* sp. via the so-called polyketide pathway (Yu, R. et al. Lipids 35:1061-1064, 2000; Takeyama, H. et al. Microbiology 143:2725-2731, 1197)).

An alternative strategy is the alternating activity of desaturases and elongases (Zank, T. K. et al. Plant Journal 31:255-268, 2002; Sakuradani, E. et al. Gene 238:445-453, 1999). A modification of the above-described pathway by Δ6-desaturase, Δ6-elongase, Δ5-desaturase, Δ5-elongase and Δ4-desaturase is the Sprecher pathway (Sprecher 2000, Biochim. Biophys. Acta 1486:219-231) in mammals. Instead of the Δ4-desaturation, a further elongation step is effected here to give $C_{24}$, followed by a further Δ6-desaturation and finally n-oxidation to give the $C_{22}$ chain length. What is known as the Sprecher pathway is, however, not suitable for the production in plants and microorganisms since the regulatory mechanisms are not known.

Depending on their desaturation pattern, the polyunsaturated fatty acids can be divided into two large classes, viz. ω-6- or ω-3-fatty acids, which differ with regard to their metabolic and functional activities.

The starting material for the ω-6-metabolic pathway is the fatty acid linoleic acid ($18:2^{\Delta 9,12}$) while the ω-3-pathway proceeds via linolenic acid ($18:3^{\Delta 9,12,15}$) Linolenic acid is formed by the activity of an ω-3-desaturase (Tocher et al. 1998, Prog. Lipid Res. 37, 73-117; Domergue et al. 2002, Eur. J. Biochem. 269, 4105-4113).

Mammals, and thus also humans, have no corresponding desaturase activity (Δ12- and ω-3-desaturase) and must take up these fatty acids (essential fatty acids) via the food.

Starting with these precursors, the physiologically important polyunsaturated fatty acids arachidonic acid (=ARA, $20:4^{\Delta 5,8,11,14}$), an ω-6-fatty acid and the two ω-3-fatty acids eicosapentaenoic acid (=EPA, $20:5^{\Delta 5,8,11,14,17}$) and docosahexaenoic acid (DHA, $22:6^{\Delta 4,7,10,13,17,19}$) are synthesized via the sequence of desaturase and elongase reactions. The application of ω-3-fatty acids shows the therapeutic activity described above in the treatment of cardiovascular diseases (Shimikawa 2001, World Rev. Nutr. Diet. 88, 100-108), inflammations (Calder 2002, Proc. Nutr. Soc. 61, 345-358) and arthritis (Cleland and James 2000, J. Rheumatol. 27, 2305-2307).

From the angle of nutritional physiology, it is, therefore, important to achieve a shift between the ω-6-synthetic pathway and the ω-3-synthetic pathway (see FIG. 1) in the synthesis of polyunsaturated fatty acids so that more ω-3-fatty acids are produced. The enzymatic activities of various ω-3-desaturases which desaturate $C_{18:2}$-, $C_{22:4}$- or $C_{22:5}$-fatty acids have been described in the literature (see FIG. 1). However, none of the desaturases whose biochemistry has been described converts a broad range of substrates of the ω-6-synthetic pathway into the corresponding fatty acids of the ω-3-synthetic pathway.

There is therefore still a great demand for an ω-3-desaturase which is suitable for the production of ω-3-polyunsaturated fatty acids. All the known plant and cyanobacterial ω-3-desaturases desaturate C18-fatty acids with linoleic acid as the substrate, but cannot desaturate C20- or C22-fatty acids.

An ω-3-desaturase which can desaturate C20-polyunsaturated fatty acids is known from the fungus *Saprolegnia dicilina* (Pereira et al. 2003, Biochem. J. 2003 Dez, manuscript BJ20031319). However, it is disadvantageous that this ω-3-desaturase cannot desaturate C18- or C22-PUFAs, such as the important fatty acids C18:2-, C22:4- or 022:5-fatty acids of the ω-6-synthetic pathway. A further disadvantage of this enzyme is that it cannot desaturate fatty acids which are bound to phospholipids. Only the CoA-fatty acid esters are converted. Recently, other ω-3-desaturases have been described with a pivotal substrate specificity for ARA, DGLA and Docosatetraenoic acid (=DTA$^{\Delta 8,11,14,17}$ (WO2005/083053).

To make possible the fortification of food and/or of feed with polyunsaturated ω-3-fatty acids, there is still a great need for a simple, inexpensive process for the production of each of the aforementioned long chain polyunsaturated fatty acids, especially in eukaryotic systems.

The technical problem underlying the present invention, thus, could be seen as the provision of means and methods which allow the synthesis of LCPUFAs and which allow a shift from the ω-6-synthetic pathway to the ω-3-synthetic pathway in order to manufacture polyunsaturated fatty acids and derivatives thereof. The technical problem has been solved by the embodiments characterized below and in the accompanying claims.

Accordingly, the present invention relates to a polynucleotide comprising a nucleic acid sequences selected from the group consisting of:

(a) a nucleic acid sequence as shown in SEQ ID NO: 1 or 23;
(b) a nucleic acid sequence encoding a polypeptide having an amino acid sequence as shown in SEQ ID NO: 2 or 24;
(c) a nucleic acid sequence which is at least 70% identical to the nucleic acid sequence of (a) or (b), wherein said nucleic acid sequence encodes a polypeptide having ω-3 desaturase activity;
(d) a nucleic acid sequence being a fragment of any one of (a) to (c), wherein said fragment encodes a polypeptide having ω-3 desaturase activity; and
(e) a nucleic acid sequence encoding a polypeptide having ω-3 desaturase activity, wherein saif polypeptide comprises a polypeptide pattern as shown in a sequence selected from the group consisting of SEQ ID NO: 15, 16, 17, 18, 19, 20, 21, 22, 37, 38, 39, 40, 41, 42, 43, 44 and 45.

The term "polynucleotide" as used in accordance with the present invention relates to a polynucleotide comprising a nucleic acid sequence which encodes a polypeptide having ω-3 desaturase activity, i.e. being capable of converting a ω-6 PUFA into its corresponding ω-3 PUFA. More preferably, the polypeptide encoded by the polynucleotide of the present invention shall be capable of introducing a double bond on the ω-3-position into a ω-6 PUFA. The ω-6 PUFA is, preferably, an LCPUFA, more preferably, a C20- or C22-PUFA. C20- and C22-PUFAs are also referred to as LCPUFAs herein below. Most preferably, the polynucleotide of the present invention encodes a polypeptide which is capable of converting ω-6 DPA into DHA. Suitable assays for measuring the activities mentioned before are described in the accompanying Examples or in WO2005/083053. A polynucleotide encoding a polypeptide having the aforementioned biological activity has been obtained in accordance with the present invention from *Pythium irregulare*. Thus, the polynucleotide, preferably, comprises the nucleic acid sequence shown in SEQ ID NO: 1 or 23 encoding the polypeptide having an amino acid sequence as shown in SEQ ID NO: 2 or 24, respectively. The two polypeptides shall represent isoforms of the w3-desaturase of the present invention. It is to be understood that a polypeptide having an amino acid sequence as shown in SEQ ID NO: 2 or 24 may be also encoded due to the degenerated genetic code by other polynucleotides as well.

Moreover, the term "polynucleotide" as used in accordance with the present invention further encompasses variants of the aforementioned specific polynucleotides. Said variants may represent orthologs, paralogs or other homologs of the polynucleotide of the present invention. Homolgous polynucleotides are, preferably, polynucleotides comprise sequences as shown in any one of SEQ ID NO: 6, 7, 9, 11, 13, 30, 33 or 35 or those which encode polypeptides comprising amino acid sequences as shown in any one of SEQ ID NO: 8, 10, 12, 14, 31, 34 or 36.

The polynucleotide variants, preferably, also comprise a nucleic acid sequence characterized in that the sequence can be derived from the aforementioned specific nucleic acid sequences shown in SEQ ID NO: 1 or 23 or in any one of SEQ ID NO: 6, 7, 9, 11, 13, 30, 33 or 35 by at least one nucleotide substitution, addition and/or deletion whereby the variant nucleic acid sequence shall still encode a polypeptide having ω-3 desaturase activity as specified above. Variants also encompass polynucleotides comprising a nucleic acid sequence which is capable of hybridizing to the aforementioned specific nucleic acid sequences, preferably, under stringent hybridization conditions. These stringent conditions are known to the skilled worker and can be found in Current Protocols in Molecular Biology, John Wiley & Sons, N. Y. (1989), 6.3.1-6.3.6. A preferred example for stringent hybridization conditions are hybridization conditions in 6× sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA:DNA hybrids are, preferably, 0.1×SSC and 20° C. to 45° C., preferably between 30° C. and 45° C. The hybridization conditions for DNA:RNA hybrids are, preferably, 0.1×SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide.

The skilled worker knows how to determine the hybridization conditions required by referring to textbooks such as the textbook mentioned above, or the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. Alternatively, polynucleotide variants are obtainable by PCR-based techniques such as mixed oligonucleotide primer-based amplification of DNA, i.e. using degenerated primers against conserved domains of the polypeptides of the present invention. Conserved domains of the polypeptide of the present invention may be identified by a sequence comparison of the nucleic acid sequence of the polynucleotide or the amino acid sequence of the polypeptide of the present invention with other ω-3 desaturase sequences (see, e.g., FIG. 3). Oligonucleotides suitable as PCR primers as well as suitable PCR conditions are described in the accompanying Examples. As a template, DNA or cDNA from bacteria, fungi, plants or animals may be used. Further, variants include polynucleotides comprising nucleic acid sequences which are at least 70%, at least 75%, at least 80%, at least 85%, at least 90%, at least 95%, at least 98% or at least 99% identical to the nucleic acid sequences shown in SEQ ID NO: 1 or 23 retaining ω-3 desaturase activity. Moreover, also encompassed are polynucleotides which comprise nucleic acid sequences encoding amino acid sequences which are at least 70%, at least 75%, at least 80%, at least 85%, at least 90%, at least 95%, at least 98% or at least 99% identical to the amino acid sequences shown in SEQ ID NO: 2 or 24 or an amino acid sequence as shown in any one of SEQ ID NO: 8, 10, 12, 14, 31, 34 or 36 wherein the polypeptide comprising the amino acid sequence retains ω-3 desaturase activity. The percent identity values are, preferably, calculated over the entire amino acid or nucleic acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (J. Mol. Evolution., 25, 351-360, 1987, Higgins et al., CABIOS, 5 1989: 151-153) or the programs Gap and BestFit (Needleman and Wunsch (J. Mol. Biol. 48; 443-453 (1970)) and Smith and Waterman (Adv. Appl. Math. 2; 482-489 (1981))), which are part of the GCG software packet [Genetics Computer Group, 575 Science Drive, Madison, Wis. USA 53711 (1991)], are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

A polynucleotide comprising a fragment of any of the aforementioned nucleic acid sequences is also encompassed as a polynucleotide of the present invention. The fragment shall encode a polypeptide which still has ω-3 desaturase activity as specified above. Accordingly, the polypeptide may comprise or consist of the domains of the polypeptide of the present invention conferring the said biological activity. A fragment as meant herein, preferably, comprises at least 50, at least 100, at least 250 or at least 500 consecutive nucleotides of any one of the aforementioned nucleic acid sequences or encodes an amino acid sequence comprising at least 20, at least 30, at least 50, at least 80, at least 100 or at least 150 consecutive amino acids of any one of the aforementioned amino acid sequences.

The variant polynucleotides or fragments referred to above, preferably, encode polypeptides retaining at least 10%, at least 20%, at least 30%, at least 40%, at least 50%, at least 60%, at least 70%, at least 80% or at least 90% of the ω-3 desaturase activity exhibitited by the polypeptide shown in SEQ ID NO: 2 or 24. The activity may be tested as described in the accompanying Examples.

Further varaiant polynucleotides encompassed by the present invention comprise sequence motifs as shown in any one of SEQ ID NO: 15, 16, 17, 18, 19, 20, 21, 22, 37, 38, 39, 40, 41, 42, 43, 44 or 45. The depicted sequences show amino acid sequence patterns (also referred to as polypeptide patterns) which are required for a polynucleotide in order to encode a polypeptide having ω-3 desaturase activity as specified above and, in particular, for those polypeptides being capable of converting ω-6 DPA into DHA. In principle, a polypeptide pattern as referred to in accordance with the present invention comprises, preferably, less than 100 or less than 50, more preferably, at least 10 up to 30 or at least 15 up to 20 amino acid in length. Moreover, it is to be understood that a variant polynucleotide comprised by the present invention, preferably, comprises at least one, at least two, at least three, at least four, at least five, at least six, at least seven, at least eight, at least nine, at least ten, at least eleven, at least twelve, at least thirteen, at least fourteen, at least fifteen, at least sixteen or all of the aforementioned specific sequence motifs. Accordingly, the pattern as shown in SEQ ID NO: 15 may be combined with the pattern shown in SEQ ID NO: 16, the pattern as shown in SEQ ID NO: 16 may be combined with the pattern shown in SEQ ID NO: 17, the pattern as shown in SEQ ID NO: 17 may be combined with the pattern shown in SEQ ID NO: 18, the pattern as shown in SEQ ID NO: 18 may be combined with the pattern shown in SEQ ID NO: 19, the pattern as shown in SEQ ID NO: 19 may be combined with the pattern shown in SEQ ID NO: 20. Likewise, the pattern as shown in SEQ ID NO: 37 may be combined with the pattern shown in SEQ ID NO: 38, the pattern as shown in SEQ ID NO: 38 may be combined with the pattern shown in SEQ ID NO: 49, the pattern as shown in SEQ ID NO: 22 may be combined with the pattern shown in SEQ ID NO: 37 or the pattern as shown in SEQ ID NO: 20 may be combined with the pattern shown in SEQ ID NO: 37 and the pattern as shown in SEQ ID NO: 44. In principle, all permutations for the combination of pairs or groups of up to seventeen patterns based on the aforementioned sequence pattern are envisaged by the present invention.

The polynucleotides of the present invention either essentially consist of the aforementioned nucleic acid sequences or comprise the aforementioned nucleic acid sequences. Thus, they may contain further nucleic acid sequences as well. Preferably, the polynucleotide of the present invention may comprise further untranslated sequence at the 3' and at the 5' terminus of the coding gene region: at least 500, preferably 200, more preferably 100 nucleotides of the sequence upstream of the 5' terminus of the coding region and at least 100, preferably 50, more preferably 20 nucleotides of the sequence downstream of the 3' terminus of the coding gene region. Furthermore, the polynucleotides of the present invention may encode fusion proteins wherein one partner of the fusion protein is a polypeptide being encoded by a nucleic acid sequence recited above. Such fusion proteins may comprise as additional part other enzymes of the fatty acid or lipid biosynthesis pathways, polypeptides for monitoring expression (e.g., green, yellow, blue or red fluorescent proteins, alkaline phosphatase and the like) or so called "tags" which may serve as a detectable marker or as an auxiliary measure for purification purposes. Tags for the different purposes are well known in the art and comprise FLAG-tags, 6-histidine-tags, MYC-tags and the like.

Variant polynucleotides as referred to in accordance with the present invention may be obtained by various natural as well as artificial sources. For example, polynucleotides may be obtained by in vitro and in vivo mutagenesis approaches using the above mentioned mentioned specific polynucleotides as a basis. Moreover, polynucleotids being homologs or orthologs may be obtained from various animal, plant or fungus species. Preferably, they are obtained from plants such as algae, for example *Isochrysis, Mantoniella, Ostreococcus* or *Crypthecodinium*, algae/diatoms such as *Phaeodactylum* or *Thraustochytrium*, mosses such as *Physcomitrella* or *Ceratodon*, or higher plants such as the Primulaceae such as *Aleuritia, Calendula stellata, Osteospermum spinescens* or *Osteospermum hyoseroides*, microorganisms such as fungi, such as *Aspergillus, Thraustochytrium, Phytophthora, Entomophthora, Mucor* or *Mortierella*, bacteria such as *Shewanella*, yeasts or animals. Preferred animals are nematodes such as *Caenorhabditis*, insects or vertebrates. Among the vertebrates, the polynucleotides may, preferably, be derived from *Euteleostomi, Actinopterygii; Neopterygii; Teleostei; Euteleostei, Protacanthopterygii, Salmoniformes; Salmonidae* or *Oncorhynchus*, more preferably, from the order of the *Salmonifornnes*, most preferably, the family of the Salmonidae, such as the genus *Salmo*, for example from the genera and species *Oncorhynchus mykiss, Trutta trutta* or *Salmo trutta fario*. Moreover, the polynucleotides may be obtained from the diatoms such as the genera *Thallasiosira* or *Crypthecodinium*.

The polynucleotide of the present invention shall be provided, preferably, either as an isolated polynucleotide (i.e. isolated from its natural context such as a gene locus) or in genetically modified form. An isolated polynucleotide can, for example, comprise less than approximately 5 kb, 4 kb, 3 kb, 2 kb, 1 kb, 0.5 kb or 0.1 kb of nucleotide sequences which naturally flank the nucleic acid molecule in the genomic DNA of the cell from which the nucleic acid is derived. The polynucleotide, preferably, is double or single stranded DNA including cDNA or RNA. The term encompasses single as well as double stranded polynucleotides. Moreover, comprised are also chemically modified polynucleotides including naturally occurring modified polynucleotides such as glycosylated or methylated polynucleotides or artificial modified ones such as biotinylated polynucleotides.

Advantageously, it has been found in the studies underlying the present invention that the polypeptides being encoded by the polynucleotides of the present invention have ω-3 desaturse activity and, in particular, are capable of converting ω-6 LCPUFA substrates, such as C20- and C22-PUFAs, into the corresponding ω-3 PUFAs. As shown in Table 1 in the accompanying Examples, the conversion of ARA into EPA is catalyzed with the highest efficiency (more than 40%). However, the conversion of DGLA into ETA is also catalyzed. Remarkably, the enzymes encoded by the polynucleotides of the present invention are even capable of catalyzing the conversion of DPA into DHA. The polynucleotides of the present invention are, in principle, useful for the synthesis of LCPUFAs and compositions containing such compounds. Specifically, thanks to the present invention, LCPUFAs and, in particular, even DHA can be recombinantly manufactured using transgenic organisms, such as micro-organisms, plants and animals.

The present invention also relates to a vector comprising the polynucleotide of the present invention.

The term "vector", preferably, encompasses phage, plasmid, viral or retroviral vectors as well as artificial chromosomes, such as bacterial or yeast artificial chromosomes.

Moreover, the term also relates to targeting constructs which allow for random or site-directed integration of the targeting construct into genomic DNA. Such target constructs, preferably, comprise DNA of sufficient length for either homolgous or heterologous recombination as described in detail below. The vector encompassing the polynucleotides of the present invention, preferably, further comprises selectable markers for propagation and/or selection in a host. The vector may be incorporated into a host cell by various techniques well known in the art. If introduced into a host cell, the vector may reside in the cytoplasm or may be incorporated into the genome. In the latter case, it is to be understood that the vector may further comprise nucleic acid sequences which allow for homologous recombination or heterologous insertion. Vectors can be introduced into prokaryotic or eukaryotic cells via conventional transformation or transfection techniques. The terms "transformation" and "transfection", conjugation and transduction, as used in the present context, are intended to comprise a multiplicity of prior-art processes for introducing foreign nucleic acid (for example DNA) into a host cell, including calcium phosphate, rubidium chloride or calcium chloride co-precipitation, DEAE-dextran-mediated transfection, lipofection, natural competence, carbon-based clusters, chemically mediated transfer, electroporation or particle bombardment. Suitable methods for the transformation or transfection of host cells, including plant cells, can be found in Sambrook et al. (Molecular Cloning: A Laboratory Manual, $2^{nd}$ ed., Cold Spring Harbor Laboratory, Cold Spring Harbor Laboratory Press, Cold Spring Harbor, N.Y., 1989) and other laboratory manuals, such as Methods in Molecular Biology, 1995, Vol. 44, *Agrobacterium* protocols, Ed.: Gartland and Davey, Humana Press, Totowa, N.J. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing host/cells.

Preferably, the vector referred to herein is suitable as a cloning vector, i.e. replicable in microbial systems. Such vectors ensure efficient cloning in bacteria and, preferably, yeasts or fungi and make possible the stable transformation of plants. Those which must be mentioned are, in particular, various binary and co-integrated vector systems which are suitable for the T-DNA-mediated transformation. Such vector systems are, as a rule, characterized in that they contain at least the vir genes, which are required for the *Agrobacterium*-mediated transformation, and the sequences which delimit the T-DNA (T-DNA border). These vector systems, preferably, also comprise further cisregulatory regions such as promoters and terminators and/or selection markers with which suitable transformed host cells or organisms can be identified. While co-integrated vector systems have vir genes and T-DNA sequences arranged on the same vector, binary systems are based on at least two vectors, one of which bears vir genes, but no T-DNA, while a second one bears T-DNA, but no vir gene. As a consequence, the last-mentioned vectors are relatively small, easy to manipulate and can be replicated both in *E. coli* and in *Agrobacterium*. These binary vectors include vectors from the pBIB-HYG, pPZP, pBecks, pGreen series. Preferably used in accordance with the invention are Bin19, pBI101, pBinAR, pGPTV and pCAMBIA. An overview of binary vectors and their use can be found in Hellens et al, Trends in Plant Science (2000) 5, 446-451. Furthermore, by using appropriate cloning vectors, the polynucleotides can be introduced into host cells or organisms such as plants or animals and, thus, be used in the transformation of plants, such as those which are published, and cited, in: Plant Molecular Biology and Biotechnology (CRC Press, Boca Raton, Fla.), chapter 6/7, pp. 71-119 (1993); F. F. White, Vectors for Gene Transfer in Higher Plants; in: Transgenic Plants, vol. 1, Engineering and Utilization, Ed.: Kung and R. Wu, Academic Press, 1993, 15-38; B. Jenes et al., Techniques for Gene Transfer, in: Transgenic Plants, vol. 1, Engineering and Utilization, Ed.: Kung and R. Wu, Academic Press (1993), 128-143; Potrykus, Annu. Rev. Plant Physiol. Plant Molec. Biol. 42 (1991), 205-225.

More preferably, the vector of the present invention is an expression vector. In such an expression vector, the polynucleotide is operatively linked to expression control sequences (also called "expression cassette") allowing expression in prokaryotic or eukaryotic cells or isolated fractions thereof. Expression of said polynucleotide comprises transcription of the polynucleotide, preferably, into a translatable mRNA. Regulatory elements ensuring expression in eukaryotic cells, preferably mammalian cells, are well known in the art. They, preferably, comprise regulatory sequences ensuring initiation of transcription and, optionally, poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Moreover, inducible expression control sequences may be used in an expression vector encompassed by the present invention. Such inducible vectors may comprise tet or lac operator sequences or sequences inducible by heat shock or other environmental factors. Suitable expression control sequences are well known in the art. Beside elements which are responsible for the initiation of transcription such regulatory elements may also comprise transcription termination signals, such as the SV40-poly-A site or the tk-poly-A site, downstream of the polynucleotide. Preferably, the expression vector is also a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994).

Suitable expression vectors are known in the art such as Okayama-Berg cDNA expression vector pcDV1 (Pharmacia), pCDM8, pRc/CMV, pcDNA1, pcDNA3 (Invitro-gene) or pSPORT1 (GIBCO BRL). Further examples of typical fusion expression vectors are pGEX (Pharmacia Biotech Inc; Smith, D. B., and Johnson, K. S. (1988) Gene 67:31-40), pMAL (New England Biolabs, Beverly, Mass.) and pRIT5 (Pharmacia, Piscataway, N.J.), where glutathione S-transferase (GST), maltose E-binding protein and protein A, respectively, are fused with the recombinant target protein. Examples of suitable inducible nonfusion *E. coli* expression vectors are, inter alia, pTrc (Amann et al. (1988) Gene 69:301-315) and pET 11d (Studier et al., Gene Expression Technology: Methods in Enzymology 185, Academic Press, San Diego, Calif. (1990) 60-89). The target gene expression of the pTrc vector is based on the transcription from a hybrid trp-lac fusion promoter by host RNA polymerase. The target gene expression from the pET 11d vector is based on the transcription of a T7-gn10-lac fusion promoter, which is mediated by a coexpressed viral RNA polymerase (T7 gn1). This viral polymerase is provided by the host strains BL21 (DE3) or HMS174 (DE3) from a resident-prophage which harbors a T7 gn1 gene under the transcriptional control of the lacUV 5 promoter. The skilled worker is familiar with other vectors which are suitable in prokaryotic organisms; these vectors are, for example, in *E. coli*, pLG338, pACYC184, the pBR series such as pBR322, the pUC series such as pUC18 or pUC19, the M113mp series, pKC30, pRep4, pHS1, pHS2, pPLc236, pMBL24, pLG200, pUR290, pIN-III113-B1, λgt11 or pBdCI, in *Streptomyces* pIJ101, pIJ364, pIJ702 or pIJ361, in *Bacillus* pUB110, pC194 or pBD214, in *Corynebacterium* pSA77 or pAJ667. Examples of vectors for expression in the yeast *S. cerevisiae* comprise pYeDesaturasec1 (Baldari et al. (1987) Embo J. 6:229-234), pMFa (Kurjan and Herskowitz (1982) Cell 30:933-943), pJRY88 (Schultz et al. (1987) Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C. A. M. J. J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi (J. W. Bennett & L. L. Lasure, Ed., pp. 396-428: Academic Press: San Diego). Further suitable yeast vectors are, for example, pAG-1, YEp6, YEp13 or pEMBLYe23. As an alternative, the polynucleotides of the present invention can be also expressed in insect cells using baculovirus expression vectors. Baculovirus vectors which are available for the expression of proteins in cultured insect cells (for example Sf9 cells) comprise the pAc series (Smith et al. (1983) Mol. Cell Biol. 3:2156-2165) and the pVL series (Lucklow and Summers (1989) Virology 170:31-39).

The following promoters and expression control sequences may be, preferably, used in an expression vector according to the present invention. The cos, tac, trp, tet, trp-tet, lpp, lac, lpp-lac, laclq, T7, T5, T3, gal, trc, ara, SP6, λ-PR or λ-PL promoters are, preferably, used in Gram-negative bacteria. For Gram-positive bacteria, promoters amy and SPO2 may be used. From yeast or fungal promoters ADC1, MFα, AC, P-60, CYC1, GAPDH, TEF, rp28, ADH are, preferably, used or from plant the promoters CaMV/35S [Franck et al., Cell 21 (1980) 285-294], PRP1 [Ward et al., Plant. Mol. Biol. 22 (1993)], SSU, OCS, lib4, usp, STLS1, B33, nos or the ubiquitin or phaseolin promoter. Also preferred in this context are inducible promoters, such as the promoters described in EP A 0 388 186 (benzylsulfonamide-inducible), Plant J. 2, 1992:397-404 (Gatz et al., tetracyclin-inducible), EP A 0 335 528 (abscisic-acid-inducible) or WO 93/21334 (ethanol- or cyclohexenol-inducible). Further suitable plant promoters are the promoter of cytosolic FBPase or the ST-LSI promoter from potato (Stockhaus et al., EMBO J. 8, 1989, 2445), the phosphoribosyl-pyrophosphate amidotransferase promoter from *Glycine max* (Genbank accession No. U87999) or the node-specific promoter described in EP-A-0 249 676. Particularly preferred are promoters which enable the expression in tissues which are involved in the biosynthesis of fatty acids. Also particularly preferred are seed-specific promoters such as the USP promoter in accordance with the practice, but also other promoters such as the LeB4, DC3, phaseolin or napin promoters. Further especially advantageous promoters are seed-specific promoters which can be used for monocotyledonous or dicotyledonous plants and which are described in U.S. Pat. No. 5,608,152 (napin promoter from oilseed rape), WO 98/45461 (oleosin promoter from *Arobidopsis*, U.S. Pat. No. 5,504,200 (phaseolin promoter from *Phaseolus vulgaris*), WO 91/13980 (Bce4 promoter from *Brassica*), by Baeumlein et al., Plant J., 2, 2, 1992:233-239 (LeB4 promoter from a legume), these promoters being suitable for dicots. The following promoters are suitable for example for monocots: lpt-2 or lpt-1 promoter from barley (WO 95/15389 and WO 95/23230), hordein promoter from barley and other promoters which are suitable and which are described in WO 99/16890. In principle, it is possible to use all natural promoters together with their regulatory sequences, such as those mentioned above, for the novel process. Likewise, it is possible and advantageous to use synthetic promoters, either additionally or alone, especially when they mediate a seed-specific expression, such as, for example, as described in WO 99/16890.

The polynucleotides of the present invention can be expressed in single-cell plant cells (such as algae), see Falciatore et al., 1999, Marine Biotechnology 1 (3):239-251 and the references cited therein, and plant cells from higher plants (for example Spermatophytes, such as arable crops) by using plant expression vectors. Examples of plant expression vectors comprise those which are described in detail in: Becker, D., Kemper, E., Schell, J., and Masterson, R. (1992) "New plant binary vectors with selectable markers located proximal to the left border", Plant Mol. Biol. 20:1195-1197; and Bevan, M. W. (1984) "Binary *Agrobacterium* vectors for plant transformation", Nucl. Acids Res. 12:8711-8721; Vectors for Gene Transfer in Higher Plants; in: Transgenic Plants, Vol. 1, Engineering and Utilization, Ed.: Kung and R. Wu, Academic Press, 1993, p. 15-38. A plant expression cassette, preferably, comprises regulatory sequences which are capable of controlling the gene expression in plant cells and which are functionally linked so that each sequence can fulfill its function, such as transcriptional termination, for example polyadenylation signals. Preferred polyadenylation signals are those which are derived from *Agrobacterium tumefaciens* T-DNA, such as the gene 3 of the Ti plasmid pTiACH5, which is known as octopine synthase (Gielen et al., EMBO J. 3 (1984) 835 et seq.) or functional equivalents of these, but all other terminators which are functionally active in plants are also suitable. Since plant gene expression is very often not limited to transcriptional levels, a plant expression cassette preferably comprises other functionally linked sequences such as translation enhancers, for example the overdrive sequence, which comprises the 5'-untranslated tobacco mosaic virus leader sequence, which increases the protein/RNA ratio (Gallie et al., 1987, Nucl. Acids Research 15:8693-8711). As described above, plant gene expression must be functionally linked to a suitable promoter which performs the expression of the gene in a timely, cell-specific or tissue-specific manner. Promoters which can be used are constitutive promoters (Benfey et al., EMBO J. 8 (1989) 2195-2202) such as those which are derived from plant viruses such as 35S CAMV (Franck et al., Cell 21 (1980) 285-294), 19S CaMV (see also U.S. Pat. No. 5,352,605 and WO 84/02913) or plant promoters such as the promoter of the Rubisco small subunit, which is described in U.S. Pat. No. 4,962,028. Other preferred sequences for the use in functional linkage in plant gene expression cassettes are targeting sequences which are required for targeting the gene product into its relevant cell compartment (for a review, see Kermode, Crit. Rev. Plant Sci. 15, 4 (1996) 285-423 and references cited therein), for example into the vacuole, the nucleus, all types of plastids, such as amyloplasts, chloroplasts, chromoplasts, the extracellular space, the mitochondria, the endoplasmic reticulum, oil bodies, peroxisomes and other compartments of plant cells. As described above, plant gene expression can also be facilitated via a chemically inducible promoter (for a review, see Gatz 1997, Annu. Rev. Plant Physiol. Plant Mol. Biol., 48:89-108). Chemically inducible promoters are particularly suitable if it is desired that genes are expressed in a time-specific manner. Examples of such promoters are a salicylic-acid-inducible promoter (WO 95/19443), a tetra-cyclin-inducible promoter (Gatz et al. (1992) Plant J. 2, 397-404) and an ethanol-inducible promoter. Promoters which respond to biotic or abiotic stress conditions are also suitable promoters, for example the pathogen-induced PRP1-gene promoter (Ward et al., Plant Mol. Biol. 22 (1993) 361-366), the heat-inducible hsp80 promoter from tomato (U.S. Pat. No. 5,187,267), the cold-inducible alpha-amylase promoter from potato (WO 96/12814) or the wound-inducible pinII promoter (EP A 0 375 091). The promoters which are especially preferred are those which bring about the expression of genes in tissues and organs in which fatty acid, lipid and oil biosynthesis takes place, in seed cells such as the cells of endosperm and of the developing embryo. Suitable promoters are the napin gene promoter from oilseed rape (U.S. Pat. No. 5,608,152), the USP promoter from *Vicia faba* (Baeumlein et al., Mol. Gen. Genet., 1991, 225 (3):459-67), the oleosin promoter from *Arabidopsis* (WO 98/45461), the phaseolin promoter from *Phaseolus vulgaris* (U.S. Pat. No. 5,504,200), the Bce4 promoter from *Brassica* (WO 91/13980) or the legumin B4 promoter (LeB4; Baeumlein et al., 1992, Plant Journal, 2 (2):233-9), and promoters which bring about the seed-specific expression in monocotyledonous plants such as maize, barley, wheat, rye, rice and the like. Suitable promoters to be taken into consideration are the Ipt2 or Ipt1 gene promoter from barley (WO 95/15389 and WO 95/23230) or those which are described in WO 99/16890 (promoters from the barley hordein gene, the rice glutelin gene, the rice oryzin gene, the rice prolamin gene, the wheat gliadin gene, wheat glutelin gene, the maize zein gene, the oat glutelin gene, the *sorghum* kasirin gene, the rye secalin gene). Likewise, especially suitable are promoters which bring about the plastid-specific expression since plastids are the compartment in which the precursors and some end products of lipid biosynthesis are synthesized. Suitable promoters such as the viral RNA-polymerase promoter, are described in WO 95/16783 and WO 97/06250, and the clpP promoter from *Arabidopsis*, described in WO 99/46394.

The abovementioned vectors are only a small overview of vectors to be used in accordance with the present invention. Further vectors are known to the skilled worker and are described, for example, in: Cloning Vectors (Ed., Pouwels, P. H., et al., Elsevier, Amsterdam-New York-Oxford, 1985, ISBN 0 444 904018). For further suitable expression systems for prokaryotic and eukaryotic cells see the chapters 16 and 17 of Sambrook, J., Fritsch, E. F., and Maniatis, T., Molecular Cloning: A Laboratory Manual, $2^{nd}$ edition, Cold Spring Harbor Laboratory, Cold Spring Harbor Laboratory Press, Cold Spring Harbor, N.Y., 1989.

In a preferred embodiment of the vector of the present invention, the said vector comprises at least one polynucleotide encoding a further enzyme being involved in the biosynthesis of fatty acids or lipids. A further enzyme referred to in accordance with the present invention is, preferably, selected from the group consisting of acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allenoxide synthase(s), hydroperoxide lyase(s) or fatty acid elongase(s), acyl-CoA:lysophospholipid acyltransferase, Δ4-desaturase, Δ5-desaturase, Δ6-desaturase, Δ8-desaturase, Δ9-desaturase, Δ12-desaturase, Δ5-elongase, Δ6-elongase and Δ9-elongase. Most preferably, the vector comprises at least one polynucleotide encoding an enzyme selected from the group consisting of Δ4-desaturase, Δ5-desaturase, Δ6-desaturase, Δ8-desaturase, Δ9-desaturase, Δ12-desaturase, Δ5-elongase, Δ6-elongase and Δ9-elongase in addition to at least one polynucleotide encoding an enzyme selected from the group consisting of acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase (s), allenoxide synthase(s), hydroperoxide lyase(s) or fatty acid elongase(s), and acyl-CoA:lysophospholipid acyltransferase. The at least one polynucleotide encoding said further enzyme may be obtained from any bacteria, fungi, animal or plant and, preferably, from those specifically recited in this description. Preferably, each polynucleotide encoding a further enzyme as recited above is also linked to its own expression control sequence wherein said expression control sequences may or may not be identical. The vector of the present invention, thus, preferably, comprises at least two (i.e. the expression cassette for the polynucleotide of the present invention and the polynucleotide for the at least one further enzyme) up to a plurality of expression cassettes consisting of the polynucleotides and expression control sequences operatively linked expression control sequences thereto.

The invention also pertains to a host cell comprising the polynucleotide or the vector of the present invention.

Host cells are primary cells or cell lines derived from multicellular organisms such as plants or animals. Furthermore, host cells encompass prokaryotic or eukaryotic single cell organisms (also referred to as micro-organisms). Primary cells or cell lines to be used as host cells in accordance with the present invention may be derived from the multicellular organisms referred to below. Host cells which can be exploited are furthermore mentioned in: Goeddel, Gene Expression Technology: Methods in Enzymology 185, Academic Press, San Diego, Calif. (1990). Specific expression strains which can be used, for example those with a lower protease activity, are described in: Gottesman, S., Gene Expression Technology: Methods in Enzymology 185, Academic Press, San Diego, Calif. (1990) 119-128. These include plant cells and certain tissues, organs and parts of plants in all their phenotypic forms such as anthers, fibers, root hairs, stalks, embryos, calli, cotelydons, petioles, harvested material, plant tissue, reproductive tissue and cell cultures which is derived from the actual transgenic plant and/or can be used for bringing about the transgenic plant. Preferably, the host cells may be obtained from plants. More preferably, oil crops are envisaged which comprise large amounts of lipid compounds, such as oilseed rape, evening primrose, hemp, thistle, peanut, canola, linseed, soybean, safflower, sunflower, borage, or plants such as maize, wheat, rye, oats, triticale, rice, barley, cotton, cassava, pepper, *Tagetes*, Solanaceae plants such as potato, tobacco, eggplant and tomato, *Vicia* species, pea, alfalfa, bushy plants (coffee, cacao, tea), *Salix* species, trees (oil palm, coconut) and perennial grasses and fodder crops. Especially preferred plants according to the invention are oil crops such as soybean, peanut, oilseed rape, canola, linseed, hemp, evening primrose, sunflower, safflower, trees (oil palm, coconut). Suitable methods for obtaining host cells from the multicellular organisms referred to below as well as conditions for culturing these cells are well known in the art.

The micro-organisms are, preferably, bacteria or fungi including yeasts. Preferred fungi to be used in accordance with the present invention are selected from the group of the families Chaetomiaceae, Choanephoraceae, Cryptococcaceae, Cunninghamellaceae, Demetiaceae, Moniliaceae, Mortierellaceae, Mucoraceae, Pythiaceae, Sacaromycetaceae, Saprolegniaceae, Schizosacharomycetaceae, Sodariaceae or Tuberculariaceae. Further preferred micro-organisms are selected from the group: Choanephoraceae such as the genera *Blakeslea*, *Choanephora*, for example the genera and species *Blakeslea trispora*, *Choanephora cucurbitarum*, *Choanephora infundibulifera* var. *cucurbitarum*, Mortierellaceae, such as the genus *Mortierella*, for example the genera and species *Mortierella isabellina*, *Mortierella polycephala*, *Mortierella ramanniana*, *Mortierella vinacea*, *Mortierella zonata*, Pythiaceae such as the genera *Phytium*, *Phytophthora* for example the genera and species *Pythium debaryanum*, *Pythium intermedium*, *Pythium irregulare*, *Pythium megalacanthum*, *Pythium paroecandrum*, *Pythium sylvaticum*, *Pythium ultimum*, *Phytophthora cactorum*, *Phytophthora cinnamomi*, *Phytophthora citricola*, *Phytophthora citrophthora*, *Phytophthora cryptogea*, *Phytophthora drechsleri*, *Phytophthora erythroseptica*, *Phytophthora lateralis*, *Phytophthora megasperma*, *Phytophthora nicotianae*, *Phytophthora nicotianae* var. *parasitica*, *Phytophthora palmivora*, *Phytophthora parasitica*, *Phytophthora syringae*, Saccharomycetaceae such as the genera *Hansenula*, *Pichia*, *Saccharomyces*, *Saccharomycodes*, *Yarrowia* for example the genera and species *Hansenula anomala*, *Hansenula californica*, *Hansenula canadensis*, *Hansenula capsulata*, *Hansenula ciferrii*, *Hansenula glucozyma*, *Hansenula henricii*, *Hansenula holstii*, *Hansenula minuta*, *Hansenula nonfermentans*, *Hansenula philodendri*, *Hansenula polymorpha*, *Hansenula saturnus*, *Hansenula subpelliculosa*, *Hansenula wickerhamii*, *Hansenula wingei*, *Pichia alcoholophila*, *Pichia angusta*, *Pichia anomala*, *Pichia bispora*, *Pichia burtonii*, *Pichia canadensis*, *Pichia capsulata*, *Pichia carsonii*, *Pichia cellobiosa*, *Pichia ciferrii*, *Pichia farinosa*, *Pichia fermentans*, *Pichia finlandica*, *Pichia glucozyma*, *Pichia guilliermondii*, *Pichia haplophila*, *Pichia henricii*, *Pichia holstii*, *Pichia jadinii*, *Pichia lindnerii*, *Pichia membranaefaciens*, *Pichia methanolica*, *Pichia minuta* var. *minuta*, *Pichia minuta* var. *nonfermentans*, *Pichia norvegensis*, *Pichia ohmeri*, *Pichia pastoris*, *Pichia philodendri*, *Pichia pini*, *Pichia polymorpha*, *Pichia quercuum*, *Pichia rhodanensis*, *Pichia sargentensis*, *Pichia stipitis*, *Pichia strasburgensis*, *Pichia subpelliculosa*, *Pichia toletana*, *Pichia trehalophila*, *Pichia vinl*, *Pichia xylosa*, *Saccharomyces aceti*, *Saccharomyces bailiff*, *Saccharomyces bayanus*, *Saccharomyces bisporus*, *Saccharomyces capensis*, *Saccharomyces carlsbergensis*, *Saccharomyces cerevisiae*, *Saccharomyces cerevisiae* var. *effipsoideus*, *Saccharomyces chevalieri*, *Saccharomyces delbrueckii*, *Saccharomyces diastaticus*, *Saccharomyces drosophilarum*, *Saccharomyces elegans*, *Saccharomyces ellipsoideus*, *Saccharomyces fermentati*, *Saccharomyces florentinus*, *Saccharomyces fragilis*, *Saccharomyces heterogenicus*, *Saccharomyces hienipiensis*, *Saccharomyces inusitatus*, *Saccharomyces italicus*, *Saccharomyces kluyveri*, *Saccharomyces krusei*, *Saccharomyces lactis*, *Saccharomyces marxianus*, *Saccharomyces microeffipsoides*, *Saccharomyces montanus*, *Saccharomyces norbensis*, *Saccharomyces oleaceus*, *Saccharomyces paradoxus*, *Saccharomyces pastorianus*, *Saccharomyces pretoriensis*, *Saccharomyces roses*, *Saccharomyces Saccharomyces uvarum*, *Saccharomycodes ludwigii*, *Yarrowia lipolytica*, Schizosacharomycetaceae such as the genera *Schizosaccharomyces* e.g. the species *Schizosaccharomyces japonicus* var. *japonicus*, *Schizosaccharomyces japonicus* var. *versatilis*, *Schizosaccharomyces malidevorans*, *Schizosaccharomyces octosporus*, *Schizosaccharomyces pombe* var. *malidevorans*, *Schizosaccharomyces pombe* var. *pombe*, Thraustochytriaceae such as the genera *Althornia*, *Aplanochytrium*, *Japonochytrium*, *Schizochytrium*, *Thraustochytrium* e.g. the species *Schizochytrium aggregatum*, *Schizochytrium limacinum*, *Schizochytrium mangrovei*, *Schizochytrium minutum*, *Schizochytrium octosporum*, *Thraustochytrium aggregatum*, *Thraustochytrium amoeboideum*, *Thraustochytrium antacticum*, *Thraustochytrium arudimentale*, *Thraustochytrium aureum*, *Thraustochytrium benthicola*, *Thraustochytrium globosum*, *Thraustochytrium indicum*, *Thraustochytrium kerguelense*, *Thraustochytrium kinnei*, *Thraustochytrium motivum*, *Thraustochytrium multirudimentale*, *Thraustochytrium pachydermum*, *Thraustochytrium proliferum*, *Thraustochytrium roseum*, *Thraustochytrium rossii*, *Thraustochytrium striatum* or *Thraustochytrium visurgense*. Further preferred micro-organisms are bacteria selected from the group of the families Bacillaceae, Enterobacteriacae or Rhizobiaceae. Examples of such micro-organisms may be selected from the group: Bacillaceae such as the genera *Bacillus* for example the genera and species *Bacillus acidocaldarius, Bacillus acidoterrestris, Bacillus alcalophilus, Bacillus amyloliquefaciens, Bacillus amylolyticus, Bacillus brevis, Bacillus cereus, Bacillus circulans, Bacillus coagulans, Bacillus sphaericus* subsp. *fusiformis, Bacillus galactophilus, Bacillus globisporus, Bacillus globisporus* subsp. *marinus, Bacillus halophilus, Bacillus lentimorbus, Bacillus lentus, Bacillus licheniformis, Bacillus megaterium, Bacillus polymyxa, Bacillus psychrosaccharolyticus, Bacillus pumilus, Bacillus sphaericus, Bacillus subtilis* subsp. *spizizenii, Bacillus subtilis* subsp. *subtilis* or *Bacillus thuringiensis*; Enterobacteriacae such as the genera *Citrobacter, Edwardsiella, Enterobacter, Erwinia, Escherichia, Klebsiella, Salmonella* or *Serratia* for example the genera and species *Citrobacter amalonaticus, Citrobacter diversus, Citrobacter freundii, Citrobacter genomospecies, Citrobacter gillenii, Citrobacter intermedium, Citrobacter koseri, Citrobacter murliniae, Citrobacter* sp., *Edwardsiella hoshinae, Edwardsiella ictaluri, Edwardsiella tarda, Erwinia alni, Erwinia amylovora, Erwinia ananatis, Erwinia aphidicola, Erwinia billingiae, Erwinia cacticida, Erwinia cancerogena, Erwinia carnegieana, Erwinia carotovora* subsp. *atroseptica, Erwinia carotovora* subsp. *betavasculorum, Erwinia carotovora* subsp. *odorifera, Erwinia carotovora* subsp. *wasabiae, Erwinia chrysanthemi, Erwinia cypripedii, Erwinia dissolvens, Erwinia herbicola, Erwinia mallotivora, Erwinia milletiae, Erwinia nigrifluens, Erwinia nimipressuralis, Erwinia persicina, Erwinia psidii, Erwinia pyrifoliae, Erwinia quercina, Erwinia rhapontici, Erwinia rubrifaciens, Erwinia salicis, Erwinia stewartii, Erwinia tracheiphila, Erwinia uredovora, Escherichia adecarboxylata, Escherichia anindolica, Escherichia aurescens, Escherichia blattae, Escherichia coli, Escherichia coli* var. *communior, Escherichia coli*-mutabile, *Escherichia fergusonii, Escherichia hermannii, Escherichia* sp., *Escherichia vulneris, Klebsiella aerogenes, Klebsiella edwardsii* subsp. *atlantae, Klebsiella ornithinolytica, Klebsiella oxytoca, Klebsiella planticola, Klebsiella pneumoniae, Klebsiella pneumoniae* subsp. *pneumoniae, Klebsiella* sp., *Klebsiella terrigena, Klebsiella trevisanii, Salmonella abony, Salmonella arizonae, Salmonella bongori, Salmonella choleraesuis* subsp. *arizonae, Salmonella choleraesuis* subsp. *bongori, Salmonella choleraesuis* subsp. *cholereasuis, Salmonella choleraesuis* subsp. *diarizonae, Salmonella choleraesuis* subsp. *houtenae, Salmonella choleraesuis* subsp. *indica, Salmonella choleraesuis* subsp. *salamae, Salmonella daressalaam, Salmonella enterica* subsp. *houtenae, Salmonella enterica* subsp. *salamae, Salmonella enteritidis, Salmonella gallinarum, Salmonella heidelberg, Salmonella panama, Salmonella senftenberg, Salmonella typhimurium, Serratia entomophila, Serratia ficaria, Serratia fonticola, Serratia grimesii, Serratia liquefaciens, Serratia marcescens, Serratia marcescens* subsp. *marcescens, Serratia marinorubra, Serratia odorifera, Serratia plymouthensis, Serratia plymuthica, Serratia proteamaculans, Serratia proteamaculans* subsp. *quinovora, Serratia quinivorans* or *Serratia rubidaea*; Rhizobiaceae such as the genera *Agrobacterium, Carbophilus, Chelatobacter, Ensifer, Rhizobium, Sinorhizobium* for example the genera and species *Agrobacterium atlanticum, Agrobacterium ferrugineum, Agrobacterium gelatinovorum, Agrobacterium larrymoorei, Agrobacterium meteori, Agrobacterium radiobacter, Agrobacterium rhizogenes, Agrobacterium rubi, Agrobacterium stellulatum, Agrobacterium tumefaciens, Agrobacterium vitis, Carbophilus carboxidus, Chelatobacter heintzii, Ensifer adhaerens, Ensifer arboris, Ensifer Ensifer kostiensis, Ensifer kummerowiae, Ensifer medicae, Ensifer meliloti, Ensifer saheli, Ensifer terangae, Ensifer xinjiangensis, Rhizobium ciceri Rhizobium etli, Rhizobium fredii, Rhizobium galegae, Rhizobium gallicum, Rhizobium giardinii, Rhizobium hainanense, Rhizobium huakuii, Rhizobium huautlense, Rhizobium indigoferae, Rhizobium japonicum, Rhizobium leguminosarum, Rhizobium loessense, Rhizobium loti, Rhizobium lupini, Rhizobium mediterraneum, Rhizobium meliloti, Rhizobium mongolense, Rhizobium phaseoli, Rhizobium radiobacter, Rhizobium rhizogenes, Rhizobium rubi, Rhizobium sullae, Rhizobium tianshanense, Rhizobium trifolii, Rhizobium tropici, Rhizobium undicola, Rhizobium vitis, Sinorhizobium adhaerens, Sinorhizobium arboris, Sinorhizobium fredii, Sinorhizobium kostiense, Sinorhizobium kummerowiae, Sinorhizobium medicae, Sinorhizobium meliloti, Sinorhizobium morelense, Sinorhizobium saheli* or *Sinorhizobium xinjiangense*.

How to culture the aforementioned micro-organisms is well known to the person skilled in the art.

In a preferred embodiment of the host cell of the present invention, the said host cell additionally comprises at least one further enzyme being involved in the biosynthesis of fatty acids or lipids, preferably, selected from the group consisting of: acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allenoxide synthase(s), hydroperoxide lyase(s) or fatty acid elongase(s), acyl-CoA:lysophospholipid acyltransferase, M-desaturase, $\Delta 5$-desaturase, $\Delta 6$-desaturase, $\Delta 8$-desaturase, $\Delta 9$-desaturase, $\Delta 12$-desaturase, $\Delta 5$-elongase, $\Delta 6$-elongase and $\Delta 9$-elongase. More preferably, the host cell comprises at least one further enzyme selected from the group consisting of $\Delta 4$-desaturase, $\Delta 5$-desaturase, $\Delta 6$-desaturase, $\Delta 8$-desaturase, $\Delta 9$-desaturase, $\Delta 12$-desaturase, $\Delta 5$-elongase, $\Delta 6$-elongase and $\Delta 9$-elongase in addition to at least one further enzyme selected from the group consisting of acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allenoxide synthase(s), hydroperoxide lyase(s) or fatty acid elongase(s), and acyl-CoA:lysophospholipid acyltransferase. The enzyme may be endogenously expressed in the host cell or may be exogenously supplied, e.g., by introducing one or more expression vector(s) comprising the polynucleotides encoding the aforementioned further enzymes.

The present invention also includes a method for the manufacture of a polypeptide having ω-3 desaturase activity comprising:
  (a) expressing the polynucleotide of the present invention in a host cell as specified above; and
  (b) obtaining the polypeptide encoded by said polynucleotide from the host cell.

The polypeptide may be obtained, for example, by all conventional purification techniques including affinity chromatography, size exclusion chromatography, high pressure liquid chromatography (HPLC) and precipitation techniques including antibody precipitation. It is to be understood that the method may—although preferred—not necessarily yield an essentially pure preparation of the polypeptide.

The present invention further relates to a polypeptide encoded by the polynucleotide of the present invention or which is obtainable by the aforementioned method of the present invention.

The term "polypeptide" as used herein encompasses essentially purified polypeptides or polypeptide preparations comprising other proteins in addition. Further, the term also relates to the fusion proteins or polypeptide fragments being at least partially encoded by the polynucleotide of the present invention referred to above. Moreover, it includes chemically modified polypeptides. Such modifications may be artificial modifications or naturally occurring modifications such as phosphorylation, glycosylation, myristylation and the like. The terms "polypeptide", "peptide" or "protein" are used interchangeable throughout this specification. As referred to above, the polypeptide of the present invention shall exhibit ω-3 desaturase activity and, thus, can be used for the manufacture of LCPUFAs, in particular C20- or C22-LCPUFAS, either in a host cell or in a transgenic animal or plant as described elsewhere in this specification. Surprisingly, the ω-3 desaturase activity of the polypeptide of the present invention even includes the ability to convert ω-6 DPA into DHA.

The present invention also relates to an antibody which specifically recognizes the polypeptide of the present invention.

Antibodies against the polypeptides of the invention can be prepared by well known methods using a purified polypeptide according to the invention or a suitable fragment derived therefrom as an antigen. A fragment which is suitable as an antigen may be identified by antigenicity determining algorithms well known in the art. Such fragments may be obtained either from the polypeptide of the invention by proteolytic digestion or may be a synthetic peptide. Preferably, the antibody of the present invention is a monoclonal antibody, a polyclonal antibody, a single chain antibody, a human or humanized antibody or primatized, chimerized or fragment thereof. Also comprised as antibodies by the present invention are a bispecific antibody, a synthetic antibody, an antibody fragment, such as Fab, Fv or scFv fragments etc., or a chemically modified derivative of any of these. The antibody of the present invention shall specifically bind (i.e. does not cross react with other polypeptides or peptides) to the polypeptide of the invention. Specific binding can be tested by various well known techniques.

Antibodies or fragments thereof can be obtained by using methods which are described, e.g., in Harlow and Lane "Antibodies, A Laboratory Manual", CSH Press, Cold Spring Harbor, 1988. Monoclonal antibodies can be prepared by the techniques originally described in Köhler and Milstein, Nature 256 (1975), 495, and Galfré, Meth. Enzymol. 73 (1981), 3, which comprise the fusion of mouse myeloma cells to spleen cells derived from immunized mammals.

The antibodies can be used, for example, for the immunoprecipitation, immunolocalization or purification (e.g., by affinity chromatography) of the polypeptides of the invention as well as for the monitoring of the presence of said variant polypeptides, for example, in recombinant organisms, and for the identification of compounds interacting with the proteins according to the invention.

The present invention relates to a transgenic non-human organism comprising the polynucleotide, the vector or the host cell of the present invention.

The term "non-human transgenic organism", preferably, relates to a plant, an animal or a multicellular microorganism. The polynucleotide or vector may be present in the cytoplasm of the organism or may be incorporated into the genome either heterologous or by homologous recombination. Host cells, in particular those obtained from plants or animals, may be introduced into a developing embryo in order to obtain mosaic or chimeric organisms, i.e. non-human transgenic organisms comprising the host cells of the present invention. Preferably, the non-human transgenic organism expresses the polynucleotide of the present invention in order to produce the polypeptide in an amount resulting in a detectable ω-3 desaturase activity. Suitable transgenic organisms are, preferably, all those organisms which are capable of synthesizing fatty acids, specifically unsaturated fatty acids, or which are suitable for the expression of recombinant genes.

Preferred animals to be used for making non-human transgenic organisms according to the present invention include mammals, reptiles, birds, fishes, insects and worms. Preferred mammals are rodents such as mice, rabbits or rats or farming animals such as cows, pigs, sheep or goats. Preferred fishes are derived from the classes of the Euteleostomi, Actinopterygii; Neopterygii; Teleostei; Euteleostei, Protacanthopterygii, Salmoniformes; Salmonidae or *Oncorhynchus* and, more preferably, from the order of the Salmoniformes, in particular, the family of the Salmonidae, such as the genus *Salmo*, for example from the genera and species *Oncorhynchus mykiss, Trutta trutta* or *Salmo trutta fario*. Preferred insects are flies such as the fruitfly *Drosophila melanogaster* and preferred worms may be from the family of Caenorhabditae.

A method for the production of a transgenic non-human animal comprises introduction of the polynucleotide or vector of the present invention into a germ cell, an embryonic cell, embryonic stem (ES) cell or an egg or a cell derived therefrom. Production of transgenic embryos and screening of those can be performed, e.g., as described by A. L. Joyner Ed., Gene Targeting, A Practical Approach (1993), Oxford University Press. Genomic DNA of embryonic tissues may be analyzed for the presence of the polynucleotide or vector of the present invention by hybridization-based or PCR-based techniques. A general method for making transgenic non-human animals is described in the art, see for example WO 94/24274. For making transgenic non-human organisms (which include homologously targeted non-human animals), ES cells are preferred. Details on making such transgenic non-human organisms are described in Robertson, E. J. (1987) in Teratocarcinomas and Embryonic Stem Cells: A Practical Approach. E. J. Robertson, ed. (Oxford: IRL Press), p. 71-112. Methods for producing transgenic insects, such as *Drosophila melanogaster*, are also known in the art, see for example U.S. Pat. No. 4,670,388, Brand & Perrimon, Development (1993) 118: 401-415; and Phelps & Brand, Methods (April 1998) 14: 367-379. Transgenic nematodes such as *C. elegans* can be generated as described in Mello, 1991, Embo J 10, 3959-70 or Plasterk, 1995 Methods Cell Biol 48, 59-80.

Preferred plants to be used for making non-human transgenic organisms according to the present invention are plants which are capable of synthesizing fatty acids, such as all dicotyledonous or monocotyledonous plants, algae or mosses. Advantageous plants are selected from the group of the plant families Adelotheciaceae, Anacardiaceae, Asteraceae, Apiaceae, Betulaceae, Boraginaceae, Brassicaceae, Bromeliaceae, Caricaceae, Cannabaceae, Convolvulaceae, Chenopodiaceae, Crypthecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae, Prasinophyceae or vegetable plants or ornamentals such as *Tagetes*. Examples which may be mentioned are the following plants selected from the group consisting of: Adelotheciaceae such as the genera *Physcomitrella*, such as the genus and species *Physcomitrella patens*, Anacardiaceae such as the genera *Pistacia, Mangifera, Anacardium*, for example the genus and species *Pistacia vera* [pistachio], *Mangifer indica* [mango] or *Anacardium occidentale* [cashew], Asteraceae, such as the genera *Calendula, Carthamus, Centaurea, Cichorium, Cynara, Helianthus, Lactuca, Locusta, Tagetes, Valeriana*, for example the genus and species *Calendula officinalis* [common marigold], *Carthamus tinctorius* [safflower], *Centaurea cyanus* [cornflower], *Cichorium intybus* [chicory], *Cynara scolynnus* [artichoke], *Helianthus annus* [sunflower], *Lactuca sativa, Lactuca crispa, Lactuca esculenta, Lactuca scariola* L. ssp. *sativa, Lactuca scariola* L. var. *integrata, Lactuca scariola* L. var. *integrifolia, Lactuca sativa* subsp. *romana, Locusta communis, Valeriana locusta* [salad vegetables], *Tagetes lucida, Tagetes erecta* or *Tagetes tenuifolia* [african or french marigold], Apiaceae, such as the genus *Daucus*, for example the genus and species *Daucus carota* [carrot], Betulaceae, such as the genus *Corylus*, for example the genera and species *Corylus avellana* or *Corylus colurna* [hazelnut], Boraginaceae, such as the genus *Borago*, for example the genus and species *Borago officinalis* [borage], Brassicaceae, such as the genera *Brassica, Melanosinapis, Sinapis, Arabadopsis*, for example the genera and species *Brassica napus, Brassica rapa* ssp. [oilseed rape], *Sinapis arvensis Brassica juncea, Brassica juncea* var. *juncea, Brassica juncea* var. *crispifolia, Brassica juncea* var. *foliosa, Brassica nigra, Brassica sinapioides, Melanosinapis communis* [mustard], *Brassica oleracea* [fodder beet] or *Arabidopsis thaliana*, Bromeliaceae, such as the genera *Anana, Bromelia* (pineapple), for example the genera and species *Anana comosus, Ananas ananas* or *Bromelia comosa* [pineapple], Caricaceae, such as the genus *Carica*, such as the genus and species *Carica papaya* [pawpaw], Cannabaceae, such as the genus *Cannabis*, such as the genus and species *Cannabis sativa* [hemp], Convolvulaceae, such as the genera *Ipomea, Convolvulus*, for example the genera and species *Ipomoea batatus, Ipomoea pandurata, Convolvulus batatas, Convolvulus tiliaceus, Ipomoea fastigiata, Ipomoea tiliacea, Ipomoea triloba* or *Convolvulus panduratus* [sweet potato, batate], Chenopodiaceae, such as the genus *Beta*, such as the genera and species *Beta vulgaris, Beta vulgaris* var. *altissima, Beta vulgaris* var. *Vulgaris, Beta maritima, Beta vulgaris* var. *perennis, Beta vulgaris* var. *conditiva* or *Beta vulgaris* var. *esculenta* [sugarbeet], Crypthecodiniaceae, such as the genus *Crypthecodinium*, for example the genus and species *Cryptecodinium cohnii*, Cucurbitaceae, such as the genus *Cucurbita*, for example the genera and species *Cucurbita maxima, Cucurbita mixta, Cucurbita pepo* or *Cucurbita moschata* [pumpkin/squash], Cymbellaceae such as the genera *Amphora, Cymbella, Okedenia, Phaeodactylum, Reimeria*, for example the genus and species *Phaeodactylum tricomutum*, Ditrichaceae such as the genera Ditrichaceae, *Astomiopsis, Ceratodon, Chrysoblastella, Ditrichum, Distichium, Eccremidium, Lophidion, Philibertiella, Pleuridium, Saelania, Trichodon, Skottsbergia*, for example the genera and species *Ceratodon antarcticus, Ceratodon columbiae, Ceratodon heterophyllus, Ceratodon purpureus, Ceratodon purpureus, Ceratodon purpureus* ssp. *convolutus, Ceratodon, purpureus* spp. *stenocarpus, Ceratodon purpureus* var. *rotundifolius, Ceratodon ratodon, Ceratodon stenocarpus, Chrysoblastella chilensis, Ditrichum ambiguum, Ditrichum brevisetum, Ditrichum crispatissimum, Ditrichum difficile, Ditrichum falcifolium, Ditrichum flexicaule, Ditrichum giganteum, Ditrichum heteromallum, Ditrichum lineare, Ditrichum lineare, Ditrichum montanum, Ditrichum montanum, Ditrichum pallidum, Ditrichum punctulatum, Ditrichum pusillum, Ditrichum pusillum* var. *tortile, Ditrichum rhynchostegium, Ditrichum schimperi, Ditrichum tortile, Distichium capillaceum, Distichium hagenii, Distichium inclinatum, Distichium macounii, Eccremidium floridanum, Eccremidium whiteleggei, Lophidion strictus, Pleuridium acuminatum, Pleuridium altemifolium, Pleuridium holdridgei, Pleuridium mexicanum, Pleuridium ravenelii, Pleuridium subulatum, Saelania glaucescens, Trichodon borealis, Trichodon cylindricus* or *Trichodon cylindricus* var. *oblongus*, Elaeagnaceae such as the genus *Elaeagnus*, for example the genus and species *Olea europaea* [olive], Ericaceae such as the genus *Kalmia*, for example the genera and species *Kalmia latifolia, Kalmia angustifolia, Kalmia microphylla, Kalmia polifolia, Kalmia occidentalis, Cistus chamaerhodendros* or *Kalmia lucida* [mountain laurel], Euphorbiaceae such as the genera *Manihot, Janipha, Jatropha, Ricinus*, for example the genera and species *Manihot utilissima, Janipha manihot, Jatropha manihot, Manihot aipil, Manihot dulcis, Manihot manihot, Manihot melanobasis, Manihot esculenta* [manihot] or *Ricinus communis* [castor-oil plant], Fabaceae such as the genera *Pisum, Albizia, Cathormion, Feuillea, Inga, Pithecolobium, Acacia, Mimosa, Medicajo, Glycine, Dolichos, Phaseolus, Soja*, for example the genera and species *Pisum sativum, Pisum arvense, Pisum humile* [pea], *Albizia berteriana, Albizia julibrissin, Albizia lebbeck, Acacia berteriana, Acacia littoralis, Albizia berteriana, Albizzia berteriana, Cathormion berteriana, Feuillea berteriana, Inga fragrans, Pithecellobium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericanrda julibrissin, Acacia lebbeck, Acacia macrophylla, Albizia lebbek, Feuilleea lebbeck, Mimosa lebbeck, Mimosa speciosa* [silk tree], *Medicago sativa, Medicago falcats, Medicago varia* [alfalfa], *Glycine max Dolichos soja, Glycine gracilis, Glycine hispida, Phaseolus max, Soja hispida* or *Soja max* [soybean], Funariaceae such as the genera *Aphanorrhegma, Entosthodon, Funaria, Physcomitrella, Physcomitrium*, for example the genera and species *Aphanorrhegma serratum, Entosthodon attenuatus, Entosthodon bolanderi, Entosthodon bonplandii, Entosthodon califomicus, Entosthodon drummondii, Entosthodon jamesonii, Entosthodon leibergii, Entosthodon neoscoticus, Entosthodon rubrisetus, Entosthodon spathulifolius, Entosthodon tucsoni, Funaria americana, Funaria bolanderi, Funaria calcarea, Funaria califomica, Funaria calvescens, Funaria convoluta, Funaria flavicans, Funaria groutiana, Funaria hygrometrica, Funaria hygrometrica* var. *arctica, Funaria hygrometrica* var. *calvescens, Funaria hygrometrica* var. *convoluta, Funaria hygrometrica* var. *muralis, Funaria hygrometrica* var. *utahensis, Funaria microstoma, Funaria microstoma* var. *obtusifolia, Funaria muhlenbergii, Funaria orcuttii, Funaria plano-convexa, Funaria polaris, Funaria ravenelii, Funaria rubriseta, Funaria serrata, Funaria sonorae, Funaria sublimbatus, Funaria tucsoni, Physcomitrella califomica, Physcomitrella patens, Physcomitrella reader, Physcomitrium australe, Physcomitrium califomicum, Physcomitrium collenchymatum, Physcomitrium coloradense, Physcomitrium cupuliferum, Physcomitrium drummondii,*

*Physcomitrium eurystomum, Physcomitrium flexifolium, Physcomitrium hookeri, Physcomitrium hookeri* var. *serratum, Physcomitrium immersum, Physcomitrium kellermanii, Physcomitrium megalocarpum, Physcomitrium pyriforme, Physcomitrium pyriforme* var. *serratum, Physcomitrium rufipes, Physcomitrium sandbergii, Physcomitrium subsphaericum, Physcomitrium washingtoniense*, Geraniaceae, such as the genera *Pelargonium, Cocos, Oleum*, for example the genera and species *Cocos nucifera, Pelargonium grossularioides* or *Oleum cocoas* [coconut], Gramineae, such as the genus *Saccharum*, for example the genus and species *Saccharum officinarum*, Juglandaceae, such as the genera *Juglans, Wallia*, for example the genera and species *Juglans regia, Juglans ailanthifolia, Juglans sieboldiana, Juglans cinerea, Wallia cinerea, Juglans bixbyi, Juglans califomica, Juglans Juglans intermedia, Juglans jamaicensis, Juglans major, Juglans macrocarpa, Juglans nigra* or *Wallia nigra* [walnut], Lauraceae, such as the genera *Persea, Laurus*, for example the genera and species *Laurus nobilis* [bay], *Persea americana, Persea gratissima* or *Persea persea* [avocado], Leguminosae, such as the genus *Arachis*, for example the genus and species *Arachis hypogaea* [peanut], Linaceae, such as the genera *Linum, Adenolinum*, for example the genera and species *Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense* or *Linum trigynum* [linseed], Lythrarieae, such as the genus *Punica*, for example the genus and species *Punica granatum* [pomegranate], Malvaceae, such as the genus *Gossypium*, for example the genera and species *Gossypium hirsutum, Gossypium arboreum, Gossypium barbadense, Gossypium herbaceum* or *Gossypium thurberi* [cotton], Marchantiaceae, such as the genus *Marchantia*, for example the genera and species *Marchantia berteroana, Marchantia foliacea, Marchantia macropora*, Musaceae, such as the genus *Musa*, for example the genera and species *Musa nana, Musa acuminata, Musa paradisiaca, Musa* spp. [banana], Onagraceae, such as the genera *Camissonia, Oenothera*, for example the genera and species *Oenothera biennis* or *Camissonia brevipes* [evening primrose], Palmae, such as the genus *Elacis*, for example the genus and species *Elaeis guineensis* [oil palm], Papaveraceae, such as the genus *Papaver*, for example the genera and species *Papaver orientate, Papaver rhoeas, Papaver dubium* [poppy], Pedaliaceae, such as the genus *Sesamum*, for example the genus and species *Sesamum indicum* [sesame], Piperaceae, such as the genera *Piper, Artanthe, Peperomia, Steffensia*, for example the genera and species *Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata* [cayenne pepper], Poaceae, such as the genera *Hordeum, Secale, Avena, Sorghum, Andropogon, Holcus, Panicum, Oryza, Zea* (maize), *Triticum*, for example the genera and species *Hordeum vulgare, Hordeum jubatum, Hordeum murinum, Hordeum secalinum, Hordeum distichon, Hordeum aegiceras, Hordeum hexastichon, Hordeum hexastichum, Hordeum irregulare, Hordeum sativum, Hordeum secalinum* [barley], *Secale cereale* [rye], *Avena sativa, Avena fatua, Avena byzantina, Avena fatua* var. *sativa, Avena hybrida* [oats], *Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum, Panicum militaceum Oryza sativa, Oryza latifolia* [rice], *Zea mays* [maize], *Triticum aestivum, Triticum durum, Triticum turgidum, Triticum hybernum, Triticum macha, Triticum sativum* or *Triticum vulgare* [wheat], Porphyridiaceae, such as the genera *Chroothece, Flintiella, Petrovanella, Porphyridium, Rhodella, Rhodosorus, Vanhoeffenia*, for example the genus and species *Porphyridium cruentum*, Proteaceae, such as the genus *Macadamia*, for example the genus and species *Macadamia intergrifolia* [macadamia], Prasinophyceae such as the genera *Nephroselis, Prasinococcus, ScherffeHa, Tetraselmis, Mantoniella, Ostreococcus*, for example the genera and species *Nephroselmis olivacea, Prasinococcus capsulatus, Scherffelia dubia, Tetraselmis chui, Tetraselmis suecica, Mantoniella squamata, Ostreococcus tauri*, Rubiaceae such as the genus *Cofea*, for example the genera and species *Cofea* spp., *Coffea arabica, Coffea canephora* or *Coffea liberica* [coffee], Scrophulariaceae such as the genus *Verbascum*, for example the genera and species *Verbascum blattaria, Verbascum chaixii, Verbascum densiflorum, Verbascum lagurus, Verbascum Iongifolium, Verbascum lychnitis, Verbascum nigrum, Verbascum olympicum, Verbascum phlomoides, Verbascum phoenicum, Verbascum pulverulentum* or *Verbascum thapsus* [mullein], Solanaceae such as the genera *Capsicum, Nicotiana, Solanum, Lycopersicon*, for example the genera and species *Capsicum annuum, Capsicum annuum* var. *glabriusculum, Capsicum frutescens* [pepper], *Capsicum annuum* [paprika], *Nicotiana tabacum, Nicotiana alata, Nicotiana attenuata, Nicotiana glauca, Nicotiana langsdorffii, Nicotiana obtusifolia, Nicotiana quadrivalvis, Nicotiana repanda, Nicotiana rustica, Nicotiana sylvestris* [tobacco], *Solanum tuberosum* [potato], *Solanum melongena* [eggplant], *Lycopersicon esculentum, Lycopersicon lycopersicum, Lycopersicon pyriforme, Solanum integrifolium* or *Solanum lycopersicum* [tomato], Sterculiaceae, such as the genus *Theobroma*, for example the genus and species *Theobroma cacao* [cacao] or Theaceae, such as the genus *Camellia*, for example the genus and species *Camellia sinensis* [tea]. In particular preferred plants to be used as transgenic plants in accordance with the present invention are oil fruit crops which comprise large amounts of lipid compounds, such as peanut, oilseed rape, canola, sunflower, safflower, poppy, mustard, hemp, castor-oil plant, olive, sesame, *Calendula, Punica*, evening primrose, mullein, thistle, wild roses, hazelnut, almond, *macadamia*, avocado, bay, pumpkin/squash, linseed, soybean, pistachios, borage, trees (oil palm, coconut, walnut) or crops such as maize, wheat, rye, oats, triticale, rice, barley, cotton, cassava, pepper, *Tagetes*, Solanaceae plants such as potato, tobacco, eggplant and tomato, *Vicia* species, pea, alfalfa or bushy plants (coffee, cacao, tea), *Salix* species, and perennial grasses and fodder crops. Preferred plants according to the invention are oil crop plants such as peanut, oilseed rape, canola, sunflower, safflower, poppy, mustard, hemp, castor-oil plant, olive, *Calendula, Punica*, evening primrose, pumpkin/squash, linseed, soybean, borage, trees (oil palm, coconut). Especially preferred are plants which are high in C18:2- and/or C18:3-fatty acids, such as sunflower, safflower, tobacco, mullein, sesame, cotton, pumpkin/squash, poppy, evening primrose, walnut, linseed, hemp, thistle or safflower. Very especially preferred plants are plants such as safflower, sunflower, poppy, evening primrose, walnut, linseed, or hemp.

Preferred mosses are *Physcomitrella* or *Ceratodon*. Preferred algae are *Isochrysis, Mantoniella, Ostreococcus* or *Crypthecodinium*, and algae/diatoms such as *Phaeodactylum* or *Thraustochytrium*. More preferably, said algae or mosses are selected from the group consisting of: *Shewanella, Physcomitrella, Thraustochytrium, Fusarium, Phytophthora, Ceratodon, Isochrysis, Aleurita, Muscarioides, Mortierella, Phaeodactylum, Cryphthecodinium*, specifically from the genera and species *Thallasiosira pseudonona, Euglena gracilis, Physcomitrella patens, Phytophtora infestans, Fusarium graminaeum, Cryptocodinium cohnii, Ceratodon purpureus, Isochrysis galbana, Aleurita farinosa, Thraustochytrium sp., Muscarioides viallii, Mortierella alpina, Phaeodactylum tricornutum* or *Caenorhabditis elegans* or especially advantageously *Phytophtora infestans, Thallasiosira pseudonona* and *Cryptocodinium cohnii*.

Transgenic plants may be obtained by transformation techniques as published, and cited, in: Plant Molecular Biology and Biotechnology (CRC Press, Boca Raton, Fla.), chapter 6/7, pp. 71-119 (1993); F. F. White, Vectors for Gene Transfer in Higher Plants; in: Transgenic Plants, vol. 1, Engineering and Utilization, Ed.: Kung and R. Wu, Academic Press, 1993, 15-38; B. Jenes et al., Techniques for Gene Transfer, in: Transgenic Plants, vol. 1, Engineering and Utilization, Ed.: Kung and R. Wu, Academic Press (1993), 128-143; Potrykus, Annu. Rev. Plant Physiol. Plant Molec. Biol. 42 (1991), 205-225. Preferably, transgenic plants can be obtained by T-DNA-mediated transformation. Such vector systems are, as a rule, characterized in that they contain at least the vir genes, which are required for the *Agrobacterium*-mediated transformation, and the sequences which delimit the T-DNA (T-DNA border). Suitable vectors are described elsewhere in the specification in detail.

Preferably, a multicellular micro-organism as used herein refers to protists or diatoms. More preferably, it is selected from the group of the families Dinophyceae, Turaniellidae or Oxytrichidae, such as the genera and species: *Crypthecodinium cohnii, Phaeodactylum tricornutum, Stylonychia mytilus, Stylonychia pustulate, Stylonychia putrina, Stylonychia notophora, Stylonychia sp., Colpidium campylum* or *Colpidium sp.*

The present invention further encompasses a method for the manufacture of a compound having a structure as shown in the general formula I

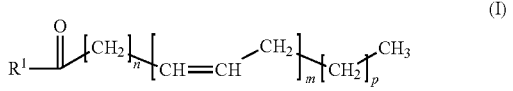

(I)

wherein the variables and substituents in formula I are
$R^1$=hydroxyl, coenzyme A (thioester), lysophosphatidylcholine, lysophosphatidyl-ethanolamine, lysophosphatidylglycerol, lysodiphosphatidylglycerol, lysophosphatidylserine, lysophosphatidylinositol, sphingo base or a radical of the formula

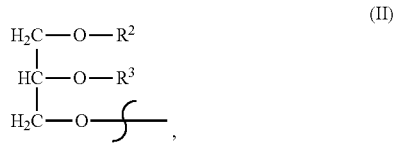

(II)

$R^2$=hydrogen, lysophosphatidylcholine, lysophosphatidylethanolamine, lysophosphatidylglycerol, lysodiphosphatidylglycerol, lysophosphatidylserine, lysophosphatidylinositol or saturated or unsaturated $C_2$-$C_{24}$-alkylcarbonyl,
$R^3$=hydrogen, saturated or unsaturated $C_2$-$C_{24}$-alkylcarbonyl, or $R^2$ and $R^3$ independently of each other are a radical of the formula Ia:

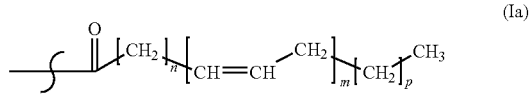

(Ia)

n=2, 3, 4, 5, 6, 7 or 9, m=2, 3,4, 5 or 6 and p=0 or 3;
and
wherein said method comprises cultivating (i) the host cell of any of claims 3 to 5, (ii) the transgenic non-human organism of claim 12 or 13 or (iii) a host cell or a transgenic non-human organism comprising a polynucleotide comprising a nucleic acid sequence as shown in any one of SEQ ID NO: 6, 7, 9, 11, 13, 30, 33 or 35 or which encodes a polypeptide having an amino acid sequence as shown in any one of SEQ ID NO: 8, 10, 12, 14, 31, 34 or 36 under conditions which allow biosynthesis of the said compound, preferably, with a content of at least 1% by weight of these compounds based on the total lipid content of the host cell or the transgenic non-human organism.

Preferably, $R^1$ in the general formula I is hydroxyl, coenzyme A (thioester), ysophosphatidylcholine, lysophosphatidylethanolannine, lysophosphatidylglycerol, lysodiphosphatidylglycerol, lysophosphatidylserine, lysophosphatidylinositol, sphingo base or a radical of the formula II

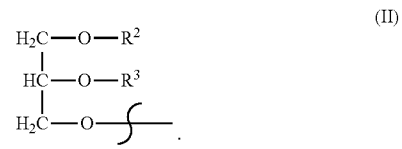

(II)

The abovementioned radicals of $R^1$ are always bonded to the compounds of the general formula I in the form of their thioesters.

Preferably, $R^2$ in the general formula II is hydrogen, lysophosphatidylcholine, lysophosphatidylethanolamine, lysophosphatidylglycerol, lysodiphosphatidylglycerol, lysophosphatidylserine, lysophosphatidylinositol or saturated or unsaturated $C_2$-$C_{24}$-alkylcarbonyl. Moreover, alkyl radicals which may be mentioned are substituted or unsubstituted, saturated or unsaturated $C_2$-$C_{24}$-alkylcarbonyl chains such as ethylcarbonyl, n-propylcarbonyl, n-butylcarbonyl, n-pentylcarbonyl, n-hexylcarbonyl, n-heptylcarbonyl, n-octylcarbonyl, n-nonylcarbonyl, n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl-, n-nonadecylcarbonyl, n-eicosylcarbonyl, n-docosanylcarbonyl- or n-tetracosanylcarbonyl, which comprise one or more double bonds. Saturated or unsaturated $C_{10}$-$C_{22}$-alkylcarbonyl radicals such as n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds, are preferred. Preferred are saturated and/or unsaturated $C_{10}$-$C_{22}$-alkylcarbonyl radicals such as $C_{10}$-alkylcarbonyl, $C_{11}$-alkylcarbonyl, $C_{12}$-alkylcarbonyl, $C_{13}$-alkylcarbonyl, $C_{14}$-alkylcarbonyl, $C_{16}$-alkylcarbonyl, $C_{18}$-alkylcarbonyl, $C_{20}$-alkylcarbonyl or $C_{22}$-alkylcarbonyl radicals which comprise one or more double bonds. Particularly preferred are saturated or unsaturated $C_{20}$-$C_{22}$-alkylcarbonyl radicals such as $C_{20}$-alkylcarbonyl or $C_{22}$-alkylcarbonyl radicals which comprise one or more double bonds. These preferred radicals can comprise two, three, four, five or six double bonds. The particularly preferred radicals with 20 or 22 carbon atoms in the fatty acid chain comprise up to six double bonds, advantageously two, three, four or five double bonds, especially preferably two, three or four double bonds. All the abovementioned radicals are derived from the corresponding fatty acids.

Preferably, $R^3$ in the formula II is hydrogen, saturated or unsaturated $C_2$-$C_{24}$-alkylcarbonyl. Alkyl radicals which may be mentioned are substituted or unsubstituted, saturated or unsaturated $C_2$-$C_{24}$-alkylcarbonyl chains such as ethylcarbonyl, n-propylcarbonyl, n-butylcarbonyl-, n-pentylcarbonyl, n-hexylcarbonyl, n-heptylcarbonyl, n-octylcarbonyl, n-nonylcarbonyl, n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl-, n-nonadecylcarbonyl, n-eicosylcarbonyl, n-docosanylcarbonyl- or n-tetracosanylcarbonyl, which comprise one or more double bonds. Saturated or unsaturated $C_{10}$-$C_{22}$-alkylcarbonyl radicals such as n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds, are preferred. Preferred are saturated and/or unsaturated $C_{10}$-$C_{22}$-alkylcarbonyl radicals such as $C_{10}$-alkylcarbonyl, $C_{11}$-alkylcarbonyl, $C_{12}$-alkylcarbonyl, $C_{13}$-alkylcarbonyl, $C_{14}$-alkylcarbonyl, $C_{16}$-alkylcarbonyl, $C_{18}$-alkylcarbonyl, $C_{20}$-alkylcarbonyl or $C_{22}$-alkylcarbonyl radicals which comprise one or more double bonds. Particularly preferred are saturated or unsaturated $C_{20}$-$C_{22}$-alkylcarbonyl radicals such as $C_{20}$-alkylcarbonyl or $C_{22}$-alkylcarbonyl radicals which comprise one or more double bonds. These preferred radicals can comprise two, three, four, five or six double bonds. The particularly preferred radicals with 20 or 22 carbon atoms in the fatty acid chain comprise up to six double bonds, advantageously two, three, four or five double bonds, especially preferably two, three or four double bonds. All the abovementioned radicals are derived from the corresponding fatty acids.

The abovementioned radicals of $R^1$, $R^2$ and $R^3$ can be substituted by hydroxyl and/or epoxy groups and/or can comprise triple bonds.

The polyunsaturated fatty acids produced in the process according to the invention advantageously comprise at least two, advantageously three, four, five or six, double bonds. The fatty acids especially advantageously comprise two, three, four or five double bonds. Fatty acids produced in the method of the present invention, preferably, comprise 20 or 22 carbon atoms in the fatty acid chain. Saturated fatty acids are advantageously reacted to a minor degree, or not at all, by the nucleic acids used in the process. To a minor degree is to be understood as meaning that the saturated fatty acids are reacted with less than 5% of the activity, advantageously less than 3%, especially advantageously with less than 2% of the activity in comparison with polyunsaturated fatty acids. These fatty acids which have been produced can be produced in the process as a single product or be present in a fatty acid mixture.

Advantageously, the substituents $R^2$ or $R^3$ in the general formulae I and II independently of one another are saturated or unsaturated $C_{20}$-$C_{22}$-alkylcarbonyl; especially advantageously, are independently of one another unsaturated $C_{20}$- or $C_{22}$-alkylcarbonyl with at least two double bonds.

The polyunsaturated fatty acids produced by the method of the present invention are, preferably, bound in membrane lipids and/or triacylglycerides, but may also occur in the organisms as free fatty acids or else bound in the form of other fatty acid esters. In this context, they may be present as "pure products" or else advantageously in the form of mixtures of various fatty acids or mixtures of different glycerides. The various fatty acids which are bound in the triacylglycerides can be derived from short-chain fatty acids with 4 to 6 C atoms, medium-chain fatty acids with 8 to 12 C atoms or long-chain fatty acids with 14 to 24 C atoms. In accordance with the method of the present invention, preferred are the long-chain fatty acids, especially the LCPUFAs of $C_{20}$- and/or $C_{22}$-fatty acids.

The method of the invention, advantageously, yields fatty acid esters with polyunsaturated $C_{20}$- and/or $C_{22}$-fatty acid molecules with at least two double bonds in the fatty acid ester, preferably, with at least two, three, four, five or six double bonds in the fatty acid ester, more preferably, of at least three, four, five or six double bonds in the fatty acid ester. These fatty acid esteres, preferably, lead to the synthesis of ETA, EPA and/or DHA.

The fatty acid esters with polyunsaturated $C_{20}$- and/or $C_{22}$-fatty acid molecules can be isolated in the form of an oil or lipid, for example, in the form of compounds such as sphingolipids, phosphoglycerides, lipids, glycolipids such as glycosphingolipids, phospholipids such as phosphatidylethanolamine, phosphatidylcholine, phosphatidylserine, phosphatidylglycerol, phosphatidylinositol or diphosphatidylglycerol, monoacylglycerides, diacylglycerides, triacylglycerides or other fatty acid esters such as the acetylcoenzyme A esters which comprise the polyunsaturated fatty acids with at least two, three, four, five or six, preferably five or six, double bonds, from the organisms which were used for the preparation of the fatty acid esters. Preferably, they are isolated in the form of their diacylglycerides, triacylglycerides and/or in the form of phosphatidylcholine, especially preferably in the form of the triacylglycerides. In addition to these esters, the polyunsaturated fatty acids are also present in the non-human transgenic organisms or host cells, preferably in the plants, as free fatty acids or bound in other compounds. As a rule, the various abovementioned compounds (fatty acid esters and free fatty acids) are present in the organisms with an approximate distribution of 80 to 90% by weight of triglycerides, 2 to 5% by weight of diglycerides, 5 to 10% by weight of monoglycerides, 1 to 5% by weight of free fatty acids, 2 to 8% by weight of phospholipids, the total of the various compounds amounting to 100% by weight.

In the method of the invention, the LCPUFAs which have been produced are produced in a content of at least 1% by weight, at least 2% by weight, at least 3% by weight, advantageously at least 5% by weight, preferably at least 8% by weight, especially preferably at least 10% by weight, very especially preferably at least 15% by weight, based on the total fatty acids in the non-human transgenic organisms or the host cell referred to above. The fatty acids are, preferably, produced in bound form. It is possible, with the aid of the polynucleotides and polypeptides of the present invention, for these unsaturated fatty acids to be positioned at the sn1, sn2 and/or sn3 position of the triglycerides which are, preferably, to be produced.

In the LCPUFA manufacturing method of the present invention the polynucleotides and polypeptides of the present invention may be used with at least one further polynucleotide encoding an enzyme of the fatty acid or lipid biosynthesis. Preferred enzymes are in this context the Δ4-desaturase, Δ5-desaturase, Δ6-desaturase, Δ8-desaturase, Δ5-elongase, Δ6-elongase and/or Δ9-elongase gene. These enzymes reflect the individual steps according to which the end products of the method of the present invention, for example, ETA, EPA or DHA are produced from the starting compounds linoleic acid (C18:2) or linolenic acid (C18:3). As a rule, these compounds are not generated as essentially pure products. Rather, small traces of the precursors may be also present in the end product. If, for example, both linoleic acid and linolenic acid are present in the starting organism, or the starting plant, the end products, such as ETA, EPA or DHA, are present as mixtures. The precursors should advantageously not amount to more than 20% by weight, preferably not to more than 15% by weight, more preferably, not to more than 10% by weight, most preferably not to more than 5% by weight, based on the amount of the end product in question. Advantageously, only STA, only EPA or only, more preferably, DHA, bound or as free acids, are produced as end products in the process of the invention in a transgenic plant. If the compounds ETA, EPA and DHA are produced simultaneously, they are, preferably, produced in a ratio of at least 1:10:20 (DHA:ETA:EPA), more preferably, the ratios are 1:5:10 or 1:2:5 and, most preferably, 1:0.1:3.

Fatty acid esters or fatty acid mixtures produced by the invention, preferably, comprise 6 to 15% of palmitic acid, 1 to 6% of stearic acid, 7-85% of oleic acid, 0.5 to 8% of vaccenic acid, 0.1 to 1% of arachic acid, 7 to 25% of saturated fatty acids, 8 to 85% of monounsaturated fatty acids and 60 to 85% of polyunsaturated fatty acids, in each case based on 100% and on the total fatty acid content of the organisms. DHA as a preferred long chain polyunsaturated fatty acid is present in the fatty acid esters or fatty acid mixtures in a concentration of, preferably, at least 0.1; 0.2; 0.3; 0.4; 0.5; 0.6; 0.7; 0.8; 0.9 or 1%, based on the total fatty acid content. Moreover, the fatty acid esters or fatty acid mixtures which have been produced by the method of the invention, preferably, comprise further fatty acids selected from the group of the fatty acids erucic acid (13-docosaenoic acid), sterculic acid (9,10-methyleneoctadec-9-enoic acid), malvalic acid (8,9-methyleneheptadec-8-enoic acid), chaulmoogric acid (cyclopentenedodecanoic acid), furan fatty acid (9,12-epoxyoctadeca-9,11-dienoic acid), vernolic acid (9,10-epoxyoctadec-12-enoic acid), tariric acid (6-octadecynoic acid), 6-nonadecynoic acid, santalbic acid (t11-octadecen-9-ynoic acid), 6,9-octadecenynoic acid, pyrulic acid (t10-heptadecen-8-ynoic acid), crepenyninic acid (9-octadecen-12-ynoic acid), 13,14-dihydroöropheic acid, octadecen-13-ene-9,11-diynoic acid, petroselenic acid (cis-6-octadecenoic acid), 9c,12t-octadecadienoic acid, calendulic acid (8t10t12c-octadecatrienoic acid), catalpic acid (9t11t13c-octadecatrienoic acid), eleostearic acid (9c11t-octadecatrienoic acid), jacaric acid (8c10t12c-octadecatrienoic acid), punicic acid (9c11t-c-octadecatrienoic acid), parinaric acid (9c11t13t15c-octadecatetraenoic acid), pinolenic acid (all-cis-5,9,12-octadecatrienoic acid), laballenic acid (5,6-octadecadienallenic acid), ricinoleic acid (12-hydroxyoleic acid) and/or coriolic acid (13-hydroxy-9c,11t-octadecadienoic acid). The fatty acid esters or fatty acid mixtures produced by the method of the present invention, preferably, comprise less than 0.1%, based on the total fatty acids, or no butyric acid, no cholesterol, no clupanodonic acid (=docosapentaenoic acid, $C22:5^{\Delta4,8,12,15,21}$) and no nisinic acid (tetracosahexaenoic acid, $C23:6^{\Delta3,8,12,15,18,21}$).

By using the polynucleotides or polypeptides of the present invention in the aforementioned methods, it is envisaged that the transgenic non-human organisms or host cells provide an increase in the yield of the LCPUFAs of at least 50%, at least 80%, at least 100% or at least 150% in comparison with a reference organism or cell (i.e. a non-transgenic or non-modified cell) when compared by means of gas chromatography (GC) analysis; see Examples.

Chemically pure LCPUFAs or fatty acid compositions can also be synthesized by the method described above. To this end, the fatty acids or the fatty acid compositions are isolated from the non-human transgenic organism, host cell or culture media of host cells, for example via extraction, distillation, crystallization, chromatography or a combination of these methods. These chemically pure fatty acids or fatty acid compositions are advantageous for applications in the food industry sector, the cosmetic sector and especially the pharmacological industry sector.

Genes encoding further enzymes or proteins involved in the fatty acid or lipid metabolism can be also applied for the method of the present invention. Suitable genes are, preferably, selected from the group consisting of acyl-CoA dehydrogenase(s), acyl-ACP[=acyl carrier protein] desaturase(s), acyl-ACP thioesterase(s), fatty acid acyl transferase(s), acyl-CoA:lysophospholipid acyltransferases, fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allenoxide synthases, hydroperoxide lyases or fatty acid elongase(s) are advantageously used in combination with the ω-3-desaturase. Genes selected from the group of the Δ4-desaturases, Δ5-desaturases, Δ6-desaturases, Δ8-desaturases, Δ9-desaturases, Δ12-desaturases, Δ5-elongases, Δ6-elongases or Δ9-elongases are, more preferably, used in combination with the above genes and the polynucleotide of the present invention.

The polypeptides of the invention preferentially desaturates $0_{20}$ and $C_{22}$-LCPUFAs. Within the non-human transgenic organism or the host cell, these fatty acids are converted to at least 10%, 15%, 20%, 25% or 30% from the existing fatty acid pool to give the corresponding ω-3-fatty acids. Preferred substrates of the ω-3-desaturase according to the invention are the ω-6-fatty acids bound in phospholipids. Table 1 shows the preferred substrates (i.e. DGLA, ARA and DPA) and the products (i.e. ETA, EPA and DHA).

Preferably, the LCPUFAs produced by the method of the present invention are synthesized, depending on the fatty acid present in the non-human transgenic organism or host cell, which act as starting substance for the synthesis. Since biosynthetic cascades are involved, the end products in question are not present in pure form in the organisms or host cells. Small amounts of the precursor compounds are always additionally present in the end product. These small amounts amount to less than 20% by weight, advantageously less than 15% by weight, especially advantageously less than 10% by weight, very especially advantageously less than 5, 4, 3, 2, or 1% by weight, based on the end products.

In addition to the synthesis based on endogenous precursors present in the non-human transgenic organism or host cell, the fatty acids can also be fed externally. Preferred substrates in this context are dihomo-γ-linolenic acid (C20:3$^{\Delta8,11,14}$), arachidonic acid (C20:4$^{\Delta5,8,11,14}$) and docosapentaenoic acid (C22:5$^{\Delta4,7,10,13,15}$).

To increase the yield in the above-described method for the production of oils and/or triglycerides with an advantageously elevated content of polyunsaturated fatty acids, it is preferred to increase the amount of starting product for the synthesis of fatty acids; this can be achieved, for example, by introducing, into the non-human transgenic organism or host cell, a nucleic acid which encodes a polypeptide with Δ12-desaturase activity. This is particularly preferred in oil-producing non-human organisms such as oilseed rape which are high in oleic acid. Since these organisms are only low in linoleic acid (Mikoklajczak et al., Journal of the American Oil Chemical Society, 38, 1961, 678-681), the use of the abovementioned Δ12-desaturases for producing the starting material linoleic acid is advantageous.

In a preferred embodiment of the method of the present invention, the said method, furthermore, comprises the step of obtaining the oils, lipids or free fatty acids from the organism or the host cell. It is to be understood that in case a host cell is exploited as a source, the LCPUFAs to be manufactured can be also obtained form the culture media.

In the case of plant cells, plant tissue or plant organs, "growing" is understood as meaning, for example, the cultivation on or in a nutrient medium, or of the intact plant on or in a substrate, for example in a hydroponic culture, potting compost or on arable land.

Transgenic plants which comprise the polyunsaturated fatty acids synthesized in the method according to the invention can advantageously be marketed directly without there being any need for the oils, lipids or fatty acids synthesized to be isolated. Plants for the method according to the invention are understood as meaning intact plants and all plant parts, plant organs or plant parts such as leaf, stem, seed, root, tubers, anthers, fibers, root hairs, stalks, embryos, calli, cotelydons, petioles, harvested material, plant tissue, reproductive tissue and cell cultures which are derived from the transgenic plant and/or can be used for bringing about the transgenic plant. In this context, the seed comprises all parts of the seed such as the seed coats, epidermal cells, seed cells, endosperm or embryonic tissue. However, the compounds produced in the method according to the invention can also be isolated from the organisms, advantageously the plants, in the form of their oils, fat, lipids and/or free fatty acids. LCPUFAs produced by this method can be harvested by harvesting the organisms either from the culture in which they grow, or from the field. This can be done via pressing or extraction of the plant parts, preferably the plant seeds. In this context, the oils, fats, lipids and/or free fatty acids can be obtained by what is known as cold-beating or cold-pressing without applying heat by pressing. To allow for greater ease of disruption of the plant parts, specifically the seeds, they are previously comminuted, steamed or roasted. The seeds which have been pretreated in this manner can subsequently be pressed or extracted with solvent such as warm hexane. The solvent is subsequently removed again. In the case of microorganisms, for example, these are harvested and then extracted directly without further processing steps, or else disrupted and then extracted via various methods with which the skilled worker is familiar. In this manner, more than 96% of the compounds produced in the process can be isolated. Thereafter, the resulting products are processed further, i.e. refined. In this process, substances such as the plant mucilages and suspended matter are first removed. What is known as desliming can be effected enzymatically or, for example, chemico-physically by addition of acid such as phosphoric acid. Thereafter, the free fatty acids are removed by treatment with a base, for example, sodium hydroxide solution. The resulting product is washed thoroughly with water to remove the alkali remaining in the product and then dried. To remove the pigment remaining in the product, the products are subjected to bleaching, for example using fuller's earth or active charcoal. At the end, the product is deodorized, for example using steam.

One embodiment of the invention are therefore oils, lipids or fatty acids or fractions thereof which have been prepared by the above-described process, especially preferably oil, lipid or a fatty acid composition which comprise LCPUFAs and originate from transgenic plants.

As described above, these oils, lipids or fatty acids, preferably, comprise 6 to 15% of palmitic acid, 1 to 6% of stearic acid, 7-85% of oleic acid, 0.5 to 8% of vaccenic acid, 0.1 to 1% of arachic acid, 7 to 25% of saturated fatty acids, 8 to 85% of monounsaturated fatty acids and 60 to 85% of polyunsaturated fatty acids, in each case based on 100% and on the total fatty acid content of the organisms. Preferred LCPUFAs present in the fatty acid esters or fatty acid mixtures is, preferably, at least 0.1, 0.2, 0.3, 0.4, 0.5, 0.6, 0.7, 0.8, 0.9 or 1% of DHA, EPA or ETA, based on the total fatty acid content. Moreover, the fatty acid esters or fatty acid mixtures which have been produced by the process of the invention, preferably, comprise further fatty acids selected from the group of the fatty acids erucic acid (13-docosaenoic acid), sterculic acid (9,10-methyleneoctadec-9-enoic acid), malvalic acid (8,9-methyleneheptadec-8-enoic acid), chaulmoogric acid (cyclopentenedodecanoic acid), furan fatty acid (9,12-epoxyoctadeca-9,11-dienoic acid), vernonic acid (9,10-epoxyoctadec-12-enoic acid), tariric acid (6-octadecynoic acid), 6-nonadecynoic acid, santalbic acid (t11-octadecen-9-ynoic acid), 6,9-octadecenynoic acid, pyrulic acid (t10-heptadecen-8-ynoic acid), crepenyninic acid (9-octadecen-12-ynoic acid), 13,14-dihydrooropheic acid, octadecen-13-ene-9,11-diynoic acid, petroselenic acid (cis-6-octadecenoic acid), 9c,12t-octadecadienoic acid, calendulic acid (8t10t12c-octadecatrienoic acid), catalpic acid (9t11t13c-octadecatrienoic acid), eleostearic acid (9c11t13t-octadecatrienoic acid), jacaric acid (8c10t12c-octadecatrienoic acid), punicic acid (9c11t13c-octadecatrienoic acid), parinaric acid (9c11t13t15c-octadecatetraenoic acid), pinolenic acid (all-cis-5,9,12-octadecatrienoic acid), laballenic acid (5,6-octadecadienallenic acid), ricinoleic acid (12-hydroxyoleic acid) and/or coriolic acid (13-hydroxy-9c,11t-octadecadienoic acid). The fatty acid esters or fatty acid mixtures produced by the process according to the invention advantageously comprise less than 0.1%, based on the total fatty acids, or no butter butyric acid, no cholesterol, no clupanodonic acid (=dpcpsapentaenoic acid, C22:5$^{\Delta4,8,12,15,21}$) and no nisinic acid (tetracosahexaenoic acid, C23:6$^{\Delta3,8,12,15,18,21}$).

The oils, lipids or fatty acids according to the invention, preferably, comprise at least 0.5%, 1%, 2%, 3%, 4% or 5%, more preferably, at least 6%, 7%, 8%, 9% or 10%, and most preferably at least 11%, 12%, 13%, 14% or 15% of ETA, EPA and/or of DHA, based on the total fatty acid content of the production organism, advantageously of a plant, especially of an oil crop such as soybean, oilseed rape, coconut, oil palm, safflower, flax, hemp, castor-oil plant, *Calendula*, peanut, cacao bean, sunflower or the abovementioned other monocotyledonous or dicotyledonous oil crops.

A further embodiment according to the invention is the use of the oil, lipid, fatty acids and/or the fatty acid composition in feedstuffs, foodstuffs, dietary supplies, cosmetics or pharmaceutical compositions as set forth in detail below. The oils, lipids, fatty acids or fatty acid mixtures according to the invention can be used in the manner with which the skilled worker is familiar for mixing with other oils, lipids, fatty acids or fatty acid mixtures of animal origin such as, for example, fish oils.

The terms "oil", "lipid" or "fat" are understood as meaning a fatty acid mixture comprising unsaturated or saturated, preferably esterified, fatty acid(s). The oil, lipid or fat is preferably high in polyunsaturated free or, advantageously, esterified fatty acid(s), in particular the preferred LCPUFAs referred to herein above. The amount of unsaturated esterified fatty acids preferably amounts to approximately 30%, a content of 50% is more preferred, a content of 60%, 70%, 80% or more is even more preferred. For the analysis, the fatty acid content can, for example, be determined by GC after converting the fatty acids into the methyl esters by transesterification. The oil, lipid or fat can comprise various other saturated or unsaturated fatty acids, for example calendulic acid, palmitic acid, palmitoleic acid, stearic acid, oleic acid and the like. The content of the various fatty acids in the oil or fat can vary, in particular depending on the starting organism.

The polyunsaturated fatty acids with at least two double bonds, which acids are produced by the method of the present invention are, as described in detail above.

They can be liberated, for example, via treatment with alkali, for example aqueous KOH or NaOH, or acid hydrolysis, preferably in the presence of an alcohol such as methanol or ethanol, or via enzymatic cleavage, and isolated via, for example, phase separation and subsequent acidification via, for example, $H_2SO_4$. The fatty acids can also be liberated directly without the above-described processing step.

If microorganisms are used as host cells or non-human transgenic organisms in the method of the present invention, they will be cultured, or grown, in the manner with which the skilled worker is familiar, depending on the microorganism to be used. As a rule, microorganisms will be grown in a liquid medium comprising a carbon source, mostly in the form of sugars, a nitrogen source, mostly in the form of organic nitrogen sources such as yeast extract or salts such as ammonium sulfate, trace elements such as iron, manganese and magnesium salts, and, if appropriate, vitamins, at temperatures between 0° C. and 100° C., preferably between 10° C. to 60° C., while gassing in oxygen. During this process, the pH of the liquid nutrient may be kept constant, i.e. regulated during the culture period, or not. The culture can be effected batchwise, semibatchwise or continuously. Nutrients can be introduced at the beginning of the fermentation or fed in semicontinuously or continuously. The polyunsaturated fatty acids produced can be isolated from the organisms by methods with which the skilled worker is familiar, as described above; for example via extraction, distillation, crystallization, if appropriate salt precipitation and/or chromatography. To do so, the organisms can advantageously be disrupted beforehand.

Culturing of the microorganism may be carried out at a temperature of between 0° C. to 95° C., preferably between 10° C. to 85° C., more preferably between 15° C. to 75° C., most preferably between 15° C. to 45° C.

The pH shall be maintained at between pH 4 and pH 12, preferably between pH 6 and pH 9, especially preferably between pH 7 and pH 8.

The process according to the invention can be carried out batchwise, semibatchwise or continuously. A summary of known cultivation methods is to be found in the textbook by Chmiel (Bioprozelltechnik 1. Einführung in die Bioverfahrenstechnik (Gustav Fischer Verlag, Stuttgart, 1991)) or in the textbook by Storhas (Bioreaktoren and periphere Einrichtungen (Vieweg Verlag, Braunschweig/Wiesbaden, 1994)).

The culture medium to be used must satisfy in a suitable manner the demands of the respective strains. There are descriptions of culture media for various microorganisms in the handbook "Manual of Methods for General Bacteriology" of the American Society for Bacteriology (Washington D.C., USA, 1981).

These media which can be employed according to the invention usually comprise one or more carbon sources, nitrogen sources, inorganic salts, vitamins and/or trace elements, as described above.

Preferred carbon sources are sugars such as mono-, di- or polysaccharides. Examples of very good carbon sources are glucose, fructose, mannose, galactose, ribose, sorbose, ribulose, lactose, maltose, sucrose, raffinose, starch or cellulose. Sugars can be put in the media also via complex compounds such as molasses, or other by-products of sugar refining. It may also be advantageous to add mixtures of various carbon sources. Other possible carbon sources are oils and fats such as, for example, soybean oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol and/or organic acids such as, for example, acetic acid and/or lactic acid.

Nitrogen sources are usually organic or inorganic nitrogen compounds or materials comprising these compounds. Examples of nitrogen sources include ammonia gas, ammonia liquid or ammonium salts such as ammonium sulfate, ammonium chloride, ammonium phosphate, ammonium carbonate or ammonium nitrate, nitrates, urea, amino acids or complex nitrogen sources such as corn steep liquor, soybean flour, soybean protein, yeast extract, meat extract and others. The nitrogen sources may be used singly or as mixtures.

Inorganic salt compounds which may be present in the media comprise the chloride, phosphoric or sulfate salts of calcium, magnesium, sodium, cobalt, molybdenum, potassium, manganese, zinc, copper and iron.

For producing sulfur-containing fine chemicals, especially methionine, it is possible to use as sulfur source inorganic sulfur-containing compounds such as, for example, sulfates, sulfites, dithionites, tetrathionates, thiosulfates, sulfides, but also organic sulfur compounds such as mercaptans and thiols.

It is possible to use as phosphorus source phosphoric acid, potassium dihydrogenphosphate or dipotassium hydrogenphosphate or the corresponding sodium-containing salts.

Chelating agents can be added to the medium in order to keep the metal ions in solution. Particularly suitable chelating agents comprise dihydroxyphenols such as catechol or protocatechuate, or organic acids such as citric acid.

The fermentation media employed according to the present invention for the culture of microorganisms normally also comprise other growth factors such as vitamins or growth promoters, which include for example biotin, riboflavin, thiamine, folic acid, nicotinic acid, pantothenate and pyridoxine. Growth factors and salts are frequently derived from complex components of the media, such as yeast extract, molasses, corn steep liquor and the like. Suitable precursors may also be added to the culture medium. The exact composition of the compounds in the media depends greatly on the particular experiment and will be decided individually for each specific case. Information on optimization of media is obtainable from the textbook "Applied Microbiol. Physiology, A Practical Approach" (editors P. M. Rhodes, P. F. Stanbury, IRL Press (1997) pp. 53-73, ISBN 0 19 963577 3). Growth media can also be purchased from commercial suppliers, such as Standard 1 (Merck) or BHI (Brain heart infusion, DIFCO) and the like.

All the components of the media are sterilized either by heat (20 min at 1.5 bar and 121° C.) or by filter sterilization. The components can be sterilized either together or, if necessary, separately. All the components of the media may be present at the start of culturing or optionally be added continuously or batchwise.

The temperature of the culture is normally between 15° C. and 45° C., preferably at 25° C. to 40° C., and can be kept constant or changed during the experiment. The pH of the medium should be in the range from 5 to 8.5, preferably around 7.0. The pH for the culturing can be controlled during the culturing by adding basic compounds such as sodium hydroxide, potassium hydroxide, ammonia or aqueous ammonia or acidic compounds such as phosphoric acid or sulfuric acid. The development of foam can be controlled by employing antifoams such as, for example, fatty acid polyglycol esters. The stability of plasmids can be maintained by adding to the medium suitable substances with a selective action, such as, for example, antibiotics. Aerobic conditions are maintained by introducing oxygen or oxygen-containing gas mixtures such as, for example, ambient air into the culture. The temperature of the culture is normally 20° C. to 45° C., and preferably 25° C. to 40° C. The culture is continued until formation of the desired product is at a maximum. This aim is normally reached within 10 hours to 160 hours.

The dry matter content of the fermentation broths obtained in this way and comprising in particular polyunsaturated fatty acids is normally from 7.5 to 25% by weight.

The fermentation broth can then be processed further. Depending on the requirement, the biomass can be removed wholly or partly from the fermentation broth by separation methods such as, for example, centrifugation, filtration, decantation or a combination of these methods, or left completely in it. The biomass is advantageously worked up after removal.

However, the fermentation broth can also be thickened or concentrated by known methods such as, for example, with the aid of a rotary evaporator, thin-film evaporator, falling-film evaporator, by reverse osmosis or by nanofiltration, without involving a cell removal step. This concentrated fermentation broth can then be worked up to obtain the fatty acids comprised therein.

The present invention, furthermore, relates to a method for the manufacture of an oil-, fatty acid- or lipid-containing composition comprising the steps of the method of the present invention and the further step or formulating the compound as an oil-, fatty acid- or lipid-containing composition.

The term "composition" refers to any composition formulated in solid, liquid or gaseous form. Said composition comprises the compound of the invention optionally together with suitable auxiliary compounds such as diluents or carriers or further ingredients. In this context, it is distinguished for the present invention between auxiliary compounds, i.e. compounds which do not contribute to the effects elicited by the compounds of the present invention upon application of the composition for its desired purpose, and further ingredients, i.e. compounds which contribute a further effect or modulate the effect of the compounds of the present invention. Suitable diluents and/or carriers depend on the purpose for which the composition is to be used and the other ingredients. The person skilled in the art can determine such suitable diluents and/or carriers without further ado. Examples of suitable carriers and/or diluents are well known in the art and include saline solutions such as buffers, water, emulsions, such as oil/water emulsions, various types of wetting agents, etc.

In a more preferred embodiment of the oil-, fatty acid or lipid-containing composition, the said composition is further formulated as a pharmaceutical composition, a cosmetic composition, a foodstuff, a feedstuff, preferably, fish feed or a dietary supply.

The term "pharmaceutical composition" as used herein comprises the compounds of the present invention and optionally one or more pharmaceutically acceptable carrier. The compounds of the present invention can be formulated as pharmaceutically acceptable salts. Acceptable salts comprise acetate, methylester, HCl, sulfate, chloride and the like. The pharmaceutical compositions are, preferably, administered topically or systemically. Suitable routes of administration conventionally used for drug administration are oral, intravenous, or parenteral administration as well as inhalation. However, depending on the nature and mode of action of a compound, the pharmaceutical compositions may be administered by other routes as well. For example, polynucleotide compounds may be administered in a gene therapy approach by using viral vectors or viruses or liposomes.

Moreover, the compounds can be administered in combination with other drugs either in a common pharmaceutical composition or as separated pharmaceutical compositions wherein said separated pharmaceutical compositions may be provided in form of a kit of parts.

The compounds are, preferably, administered in conventional dosage forms prepared by combining the drugs with standard pharmaceutical carriers according to conventional procedures. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables.

The carrier(s) must be acceptable in the sense of being compatible with the other ingredients of the formulation and being not deleterious to the recipient thereof. The pharmaceutical carrier employed may be, for example, either a solid, a gel or a liquid. Exemplary of solid carriers are lactose, terra alba, sucrose, talc, gelatin, agar, pectin, *acacia*, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl monostearate or glyceryl distearate alone or with a wax. Said suitable carriers comprise those mentioned above and others well known in the art, see, e.g., Remington's Pharmaceutical Sciences, Mack Publishing Company, Easton, Pa.

The diluent(s) is/are selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

A therapeutically effective dose refers to an amount of the compounds to be used in a pharmaceutical composition of the present invention which prevents, ameliorates or treats the symptoms accompanying a disease or condition referred to in this specification. Therapeutic efficacy and toxicity of such compounds can be determined by stand- and pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The dosage regimen will be determined by the attending physician and other clinical factors; preferably in accordance with any one of the above described methods. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment. A typical dose can be, for example, in the range of 1 to 1000 µg; however, doses below or above this exemplary range are envisioned, especially considering the aforementioned factors. Generally, the regimen as a regular administration of the pharmaceutical composition should be in the range of 1 µg to 10 mg units per day. If the regimen is a continuous infusion, it should also be in the range of 1 µg to 10 mg units per kilogram of body weight per minute, respectively. Progress can be monitored by periodic assessment. However, depending on the subject and the mode of administration, the quantity of substance administration may vary over a wide range.

The pharmaceutical compositions and formulations referred to herein are administered at least once in order to treat or ameliorate or prevent a disease or condition recited in this specification. However, the said pharmaceutical compositions may be administered more than one time, for example from one to four times daily up to a non-limited number of days.

Specific pharmaceutical compositions are prepared in a manner well known in the pharmaceutical art and comprise at least one active compound referred to herein above in admixture or otherwise associated with a pharmaceutically acceptable carrier or diluent. For making those specific pharmaceutical compositions, the active compound(s) will usually be mixed with a carrier or the diluent, or enclosed or encapsulated in a capsule, sachet, cachet, paper or other suitable containers or vehicles. The resulting formulations are to be adopted to the mode of administration, i.e. in the forms of tablets, capsules, suppositories, solutions, suspensions or the like. Dosage recommendations shall be indicated in the prescribers or users instructions in order to anticipate dose adjustments depending on the considered recipient.

The term "cosmetic composition" relates to a composition which can be formulated as described for a pharmaceutical composition above. For a cosmetic composition, likewise, it is envisaged that the compounds of the present invention are also, preferably, used in substantially pure form. Impurities, however, may be less critical than for a pharmaceutical composition. Cosmetic compositions are, preferably, to be applied topically. Preferred cosmetic compositions comprising the compounds of the present invention can be formulated as a hair tonic, a hair restorer composition, a shampoo, a powder, a jelly, a hair rinse, an ointment, a hair lotion, a paste, a hair cream, a hair spray and/or a hair aerosol.

Finally, as is evident from the above, the present invention, in principle, relates to the use of the polynucleotides, vectors, host cells or transgenic non-human organisms of the present invention for the manufacture of a oil-, fatty acid- or lipid-containing composition. Preferably, the said composition is to be used as a pharmaceutical composition, cosmetic composition, foodstuff, feedstuff, preferably, fish feed or dietary supply.

All references cited in this specification are herewith incorporated by reference with respect to their entire disclosure content and the disclosure content specifically mentioned in this specification.

The figures show:

FIG. 1: The figure shows a comparison of the DNA sequences for the two ω-3 desaturase polynucleotides from *Pythium irrgulare* (SEQ ID NO: 1 and 23).

FIG. 2: The figure shows an alignment of the deduced amino acids for the two ω-3 desaturase polynucleotides from *Pythium irrgulare* (SEQ ID NO: 2 and 24).

FIG. 3: A comparison of the deduced amino acids for the ω-3 desaturase polypeptides from *Pythium irrgulare* (SEQ ID NO: 2), *Phytophthora infestans* (SEQ ID NO: 12) and *Saprolegnia declina* (SEQ ID NO: 31) is shown.

FIG. 4: GC analysis of fatty acid methyl esters from the yeast transformant pYES2-O3 and the control pYES2 fed with GDLA.

Figure 5:
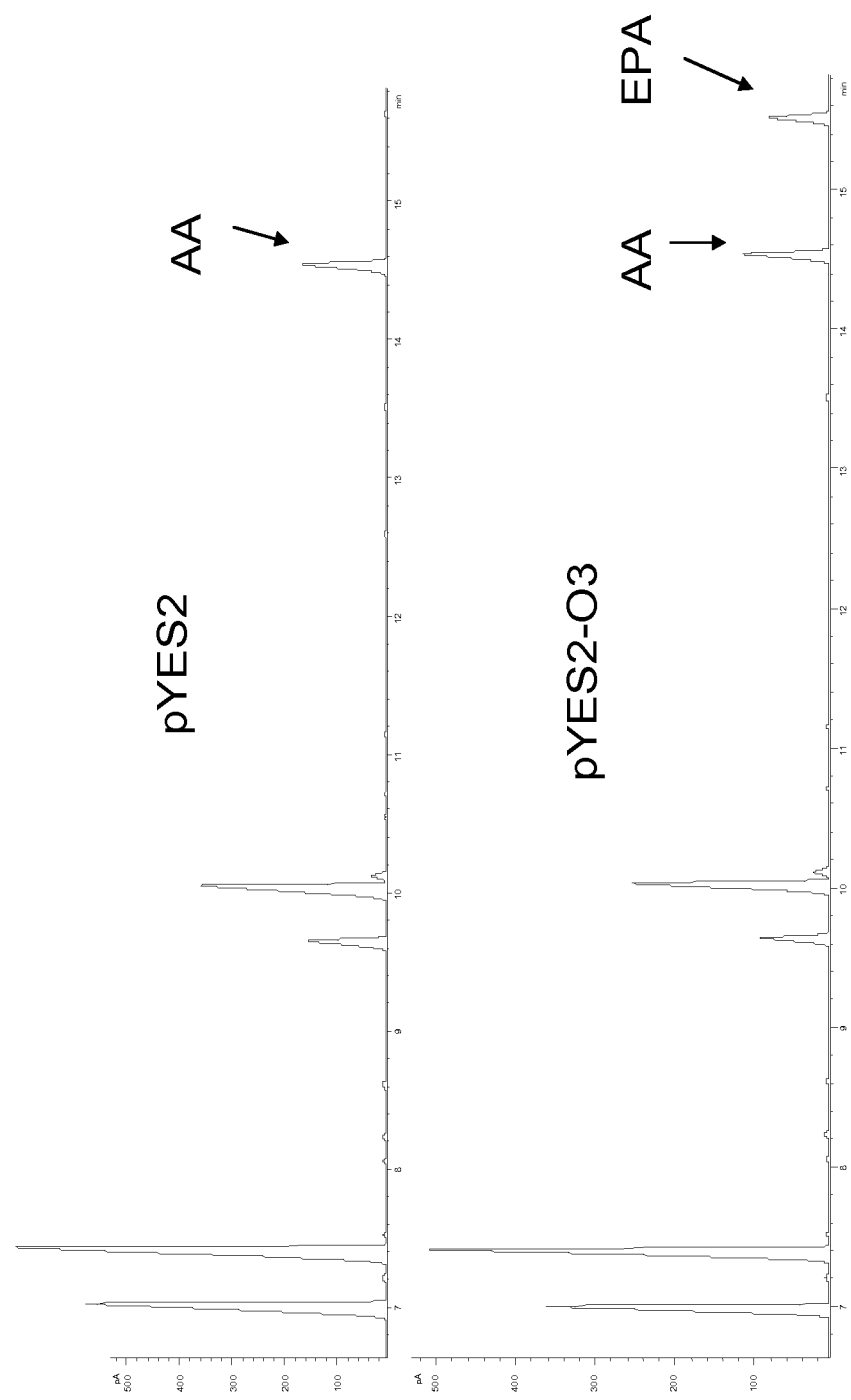

FIG. 5: GC analysis of fatty acid methyl esters from the yeast transformant pYES2-O3 and the control pYES2 fed with ARA.

Figure 6:
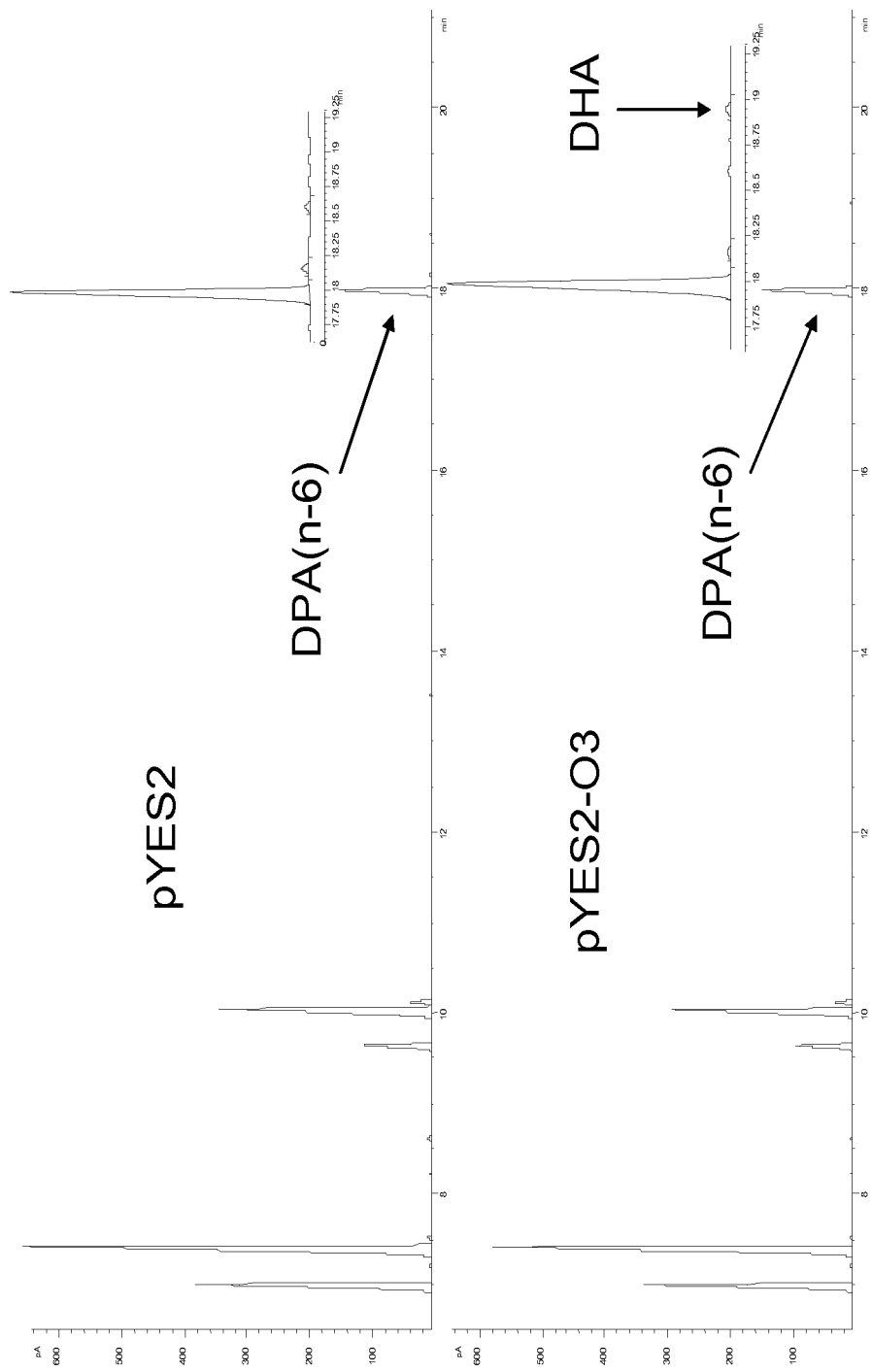

FIG. 6: GC analysis of fatty acid methyl esters from the yeast transformant pYES2-O3 and the control pYES2 fed with DPA (ω-6).

The following Examples shall merely illustrate the invention. They shall not be construed, whatsoever, to limit the scope of the invention.

Example 1: Isolation of Novel ω-3 Desaturase Polynucleotides from *Pythium irregulare*

ω-3 desaturases are the enzymes which are able to convert ω-6 fatty acids into their corresponding ω-3 PUFAs. In order to isolate polynucleotides encoding said enzymes, *Pythium irregulare* strain 10951 was ordered from ATCC. It was grown in liquid media YETG at room temperature for 5 days with constant agitation at 250 rpm. Total RNA was isolated from the harvested mycelia using TRIzol reagent (Invitrogen). The cDNA was synthesized using the Superscript III first strand kit (Invitrogen). Two pairs of degenerate primers were designed based on the conserved domains of omega-3 desaturase genes. RT-PCR was conducted to amplify the ω-3 fragments using the *Pythium* cDNA as the template by

```
                    (forward primer; SEQ ID NO: 46)
TTYTGGGGNTTYTTYACNGT
and
                    (reverse primer; SEQ ID NO: 47)
CCYTTNACYTANGTCCACT.
```

A 500 base-pair (bp) fragment was amplified and cloned into pCR4-TOPO vector (Invitrogen). A blast search from the sequence of the 500 bp fragment confirmed that it was an omega-3 desaturase gene from *Pythium irregulare*.

Based on the sequence of the ω-3 desaturase fragment from *Pythium* irregulare, two pairs of race primers and one pair of nested PCR primers were designed

```
(TCGCGCTCGCATGTGCTCAACTTCAG, RACE-F1,;   SEQ ID NO: 48

TGGTGAC-CACGAGCATCGTGGCGAAG, RACE-R1,;  SEQ ID NO: 49

TCCTCAC-GCCGTTCGAGTCCTGGAAG, RACE-F1,;  SEQ ID NO: 50

ATGGTCGTGAA-GCCCAAGACGAAGGTC, RACE-R2,. SEQ ID NO: 51)
```

A Marathon RACE cDNA library (BD Biosciences) was made using the messenger RNA isolated from total RNA from *Pythium irregulare*. PCR reactions for 3' and 5' races were applied to amplify a 800 bp and a 1000 bp fragments, respectively, from 3' and 5' RACE. These fragments were cloned into pCR4-TOPO vector (Invitrogen). Four positive clones from each race were sequenced and there are some variations among them. Therefore *Pythium irregulare* may have more than one ω-3 desaturase genes.

The assembled ω-3 desaturase gene contains a 1092 bp of open reading frame. Based the assembled ω-3 desaturase gene, one pair of primers

```
(TCCGCTCGCCATGGCGTCCAC, O3-Yes1,        SEQ ID NO: 52
and

TGACCGATCAC-TTAGCTGCAGCTTA, O3-Yes2,    SEQ ID NO: 53)
``` was designed to amplify the full length of O3 genes (ω-3 desaturase genes) from *Pythium*. The full length O3 from *Pythium* was cloned into yeast expression vector pYES2.1/V5-His-TOPO. Eight of full length clones were sequenced. Six of them are identical. This gene was designated as O3-Pythiym1. Two of other ones are identical, which was designated as O3-Pythgium2. Two genes are 99% identical (FIG. 1) and they only have one amino acid different (FIG. 2). The O3 desaturase protein from *Pythium* is 69% and 60% identical to ω-3 desaturase from *P. infestans* (WO 2005/083053) and ω-3 desaturase gene from *Saprolegnia diclina* (WO 2004/071467) (FIG. 3), respectively. It has low identities to delta-12 and delta-15 desaturase genes.

Example 2: Characterization of Novel ω-3 Desaturases from *Pythium irregulare*

The plasmids containing the full length O3 genes in the yeast expression vector pYES2.1/V5-His-TOPO were transformed into yeast *S. cerevisiae*. The positive transformants were selected for uracil auxotrophy on DOB-U agar plates. To characterize the ω-3 desaturase enzyme activity, positive clones and the control (yeast with pYES2.1 vector) were cultured overnight in DOB-U liquid medium at 28° C. and then grown in induction medium (DOB-U+Gal+Raf) containing 100 μM of various exogenously supplied fatty acid substrates at 16° C. for 4 days. The whole yeast cells expressing *Pythium* ω-3 genes were harvested by centrifugation and washed twice with distilled water. Then the yeast cells were directly transmethylated with methanolic HCl (3N) at 80° C. for 1 hour. The resultant methyl esters were extracted with hexane and analyzed by gas chromatography (GC). GC was carried out as described in WO 2005/083053.

The expression results showed that ω-3 desaturase from *Pythium* is not able to desaturase the 18-carbon ω-6 fatty acids, such as LA and GLA. It desaturates the ω-6 fatty acids longer than 18-carbon chains, such as DGLA (FIG. 4), ARA (FIG. 5) and DPA (FIG. 6). However, it is more specific to ARA with over 40% conversion rate (Table 1).

TABLE 1

Production of ω-3 fatty acids from exogenous ω-6 fatty acids in the yeast transformant (pYES2-O3) and the control yeast pYES2

| Substrate | Substrate (%) | Product | Product (%) | Conversion (%) |
|---|---|---|---|---|
| pYES2 | | | | |
| LA | 24.50 | ALA | 0 | |
| GLA | 21.97 | SDA | 0 | |
| DGLA | 15.79 | ETA | 0 | |
| ARA | 6.45 | EPA | 0 | |
| DPA | 8.26 | DHA | 0.03 | |
| pYES2-O3 | | | | |
| LA | 25.56 | ALA | 0 | 0 |
| GLA | 22.79 | SDA | 0 | 0 |
| DGLA | 17.78 | ETA | 1.90 | 9.65% |
| ARA | 7.19 | EPA | 4.95 | 40.77% |
| DPA | 9.52 | DHA | 0.20 | 2.01% |

In summary, two ω-3 desaturase isoforms were isolated from *Pythium irregulare* and both are able to introduce an ω-3 double bond into ω-6 fatty acids longer than 18 carbon chains supplied exogenously in yeast. Moreover, this is apparently the first ω-3 desaturase that is able to convert the ω-6 DPA into DHA.

We claim:

1. A method for the manufacture of a composition comprising a compound having a structure of the general formula I:

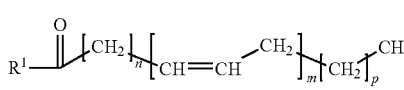

wherein

R¹=hydroxyl, coenzyme A (thioester), lysophosphatidylcholine, lysophosphatidylethanolamine, lysopho sphatidylglycerol, lysodipho sphatidylglycerol, lysopho sphatidylserine, lysophosphatidylinositol, sphingo base or a radical of the formula II:

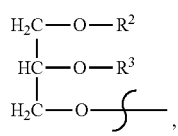

R²=hydrogen, lysophosphatidylcholine, lysophosphatidylethanolamine, lysopho sphatidylglycerol, lysodipho sphatidylglycerol, lysopho sphatidylserine, lysophosphatidylinositol or saturated or unsaturated $C_2$-$C_{24}$-alkylcarbonyl, R³=hydrogen, saturated or unsaturated $C_2$-$C_{24}$-alkylcarbonyl, or R² and R³ independently of each other are a radical of the formula Ia:

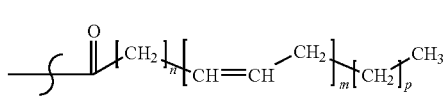

n=2, 3, 4, 5, 6, 7 or 9, m=2, 3, 4, 5 or 6 and p=0 or 3; and wherein said method comprises cultivating a host cell or a transgenic non-human organism comprising a polynucleotide comprising a heterologous nucleic acid sequence selected from the group consisting of:
(i) the nucleic acid sequence of SEQ ID NO: 1 or 23;
(ii) a nucleic acid sequence encoding a polypeptide comprising the amino acid sequence of SEQ ID NO: 2 or 24; and
(iii) a nucleic acid sequence encoding a polypeptide having omega-3 desaturase activity capable of converting omega-6 DPA into DHA, wherein said polypeptide has at least 95% sequence identity to the amino acid sequence of SEQ ID NO: 2 or 24, under conditions which allow biosynthesis of said compound.

2. The method of claim 1, further comprising formulating the composition into an oil-, fatty acid-, or lipid-containing composition.

3. The method of claim 1, wherein said host cell or transgenic non-human organism additionally comprises at least one further enzyme being involved in the biosynthesis of fatty acids or lipids.

4. The method of claim 1, wherein said host cell is an animal cell, a plant cell or a microorganism cell.

5. The method of claim 1, wherein said transgenic non-human organism is an animal, a microorganism, or a plant.

6. The method of claim 1, wherein said nucleic acid sequence encodes a polypeptide having at least one polypeptide pattern selected from the group consisting of SEQ ID NO: 15, 16, 17, 18, 19, 20, 21, 22, 37, 38, 39, 40, 41, 42, 43, 44, and 45.

7. The method of claim 2, wherein the oil-, fatty acid-, or lipid-containing composition comprises at least 0.5%, 1%, 2%, 3%, 4% or 5% of ω-3 eicostetraenic acid (ETA), eicosapentaenoic acid (EPA) and/or docosahexaenoic acid (DHA), based on the total fatty acid content of the host cell or transgenic non-human organism.

8. The method of claim 2, wherein said oil-, fatty acid-, or lipid-containing composition is further formulated as a pharmaceutical composition, a cosmetic composition, a foodstuff, a feedstuff, a fish feed or a dietary supply.

9. The method of claim 3, wherein said further enzyme is selected from the group consisting of: acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allenoxide synthase(s), hydroperoxide lyase(s) or fatty acid elongase(s), acyl-CoA:lysophospholipid acyltransferase, Δ4-desaturase, Δ5-desaturase, Δ6-desaturase, Δ8-desaturase, Δ9-desaturase, Δ12-desaturase, Δ5-elongase, Δ6-elongase and Δ9-elongase.

10. The method of claim 5, wherein the plant is an oil crop.

11. The method of claim 5, further comprising at least one of the following steps:
a) harvesting the plant or a plant part thereof from the field;
b) disrupting the plant or plant part by comminuting, steaming or roasting;
c) pressing or extracting the plant or plant part;
d) cold-beating or cold-pressing of the plant or plant part, without applying heat by pressing to obtain the oils, fats, lipids and/or free fatty acids;
e) pressing or extracting the plant or plant part with a solvent and subsequently removing the solvent;
f) removing substances such as plant mucilages and suspended matter;
g) desliming which is effected enzymatically or chemicophysically by addition of acid;
h) removing free fatty acids by treatment with a base solution;
i) washing resulting product thoroughly with water to remove alkali remaining in the product followed by drying;
j) removing pigment remaining in the product by bleaching;
k) deodorizing the product; or
l) a combination of one or more of steps a) to k).

12. The method of claim 5, wherein the plant is an intact plant or a plant part.

13. The method of claim 9, wherein the oil crop is selected from the group consisting of oilseed rape, evening primrose, hemp, thistle, peanut, canola, linseed, soybean, safflower, sunflower, borage, maize, wheat, rye, oats, triticale, rice, barley, cotton, cassava, pepper, *Tagetes*, Solanaceae plants, potato, tobacco, eggplant, tomato, *Vicia* species, pea, alfalfa, bushy plants, coffee, cacao, tea, Salix species, trees, oil palm, coconut, perennial grasses and fodder crops.

14. The method of claim 12, wherein the plant part is selected from the group consisting of leaf, stem, seed, root, tubers, anthers, fibers, root hairs, stalks, embryos, calli, cotelydons, petioles, harvested material and plant tissue.

15. A method for the manufacture of polyunsaturated fatty acids in a plant, plant part or plant cell, comprising:
   a) transforming a plant, plant part or plant cell with a polynucleotide comprising a heterologous nucleic acid sequence selected from the group consisting of:
      (i) the nucleic acid sequence of SEQ ID NO: 1 or 23;
      (ii) a nucleic acid sequence encoding a polypeptide comprising the amino acid sequence of SEQ ID NO: 2 or 24; and
      (iii) a nucleic acid sequence encoding a polypeptide having omega-3 desaturase activity capable of converting omega-6 DPA into DHA, wherein said polypeptide has at least 95% sequence identity to the amino acid sequence of SEQ ID NO: 2 or 24;
   b) cultivating the plant, plant part or plant cell under conditions which allow biosynthesis of polyunsaturated fatty acids and harvesting said plant, plant part or plant cell; and
   c) isolating the polyunsaturated fatty acids from the plant, plant part or plant cell in form of an oil, lipid or free fatty acids.

16. A method for the manufacture of triacylglycerides in a plant, plant part or plant cell, comprising:
   a) transforming a plant, plant part or plant cell with a polynucleotide comprising a heterologous nucleic acid sequence selected from the group consisting of:
      (i) the nucleic acid sequence of SEQ ID NO: 1 or 23;
      (ii) a nucleic acid sequence encoding a polypeptide comprising the amino acid sequence of SEQ ID NO: 2 or 24; and
      (iii) a nucleic acid sequence encoding a polypeptide having omega-3 desaturase activity capable of converting omega-6 DPA into DHA, wherein said polypeptide has at least 95% sequence identity to the amino acid sequence of SEQ ID NO: 2 or 24;
   b) cultivating the plant, plant part or plant cell under conditions which allow biosynthesis of triacylglycerides and harvesting said plant, plant part or plant cell; and
   c) isolating the triacylglycerides from the plant, plant part or plant cell, wherein the triacylglycerides comprise polyunsaturated fatty acids.

17. The method of claim 15, further comprising formulating the polyunsaturated fatty acids in form of free fatty acids into an oil-, fatty acid-, or lipid-containing composition.

18. The method of claim 16, further comprising formulating the triacylglycerides into an oil-, fatty acid-, or lipid-containing composition.

19. The method of claim 15, wherein said nucleic acid sequence encodes a polypeptide having at least one polypeptide pattern selected from the group consisting of SEQ ID NO: 15, 16, 17, 18, 19, 20, 21, 22, 37, 38, 39, 40, 41, 42, 43, 44, and 45.

20. The method of claim 16, wherein said nucleic acid sequence encodes a polypeptide having at least one polypeptide pattern selected from the group consisting of SEQ ID NO: 15, 16, 17, 18, 19, 20, 21, 22, 37, 38, 39, 40, 41, 42, 43, 44, and 45.

21. The method of claim 17, wherein said oil-, fatty acid-, or lipid-containing composition is further formulated as a pharmaceutical composition, a cosmetic composition, a foodstuff, a feedstuff, a fish feed or a dietary supply.

22. The method of claim 18, wherein said oil-, fatty acid-, or lipid-containing composition is further formulated as a pharmaceutical composition, a cosmetic composition, a foodstuff, a feedstuff, a fish feed or a dietary supply.

* * * * *